US011408004B2

(12) United States Patent
Collard et al.

(10) Patent No.: US 11,408,004 B2
(45) Date of Patent: Aug. 9, 2022

(54) TREATMENT OF SIRTUIN (SIRT) RELATED DISEASES BY INHIBITION OF NATURAL ANTISENSE TRANSCRIPT TO A SIRTUIN (SIRT)

(71) Applicant: CuRNA, Inc., Miami, FL (US)

(72) Inventors: Joseph Collard, Delray Beach, FL (US); Olga Khorkova Sherman, Tequesta, FL (US); Carlos Coito, West Palm Beach, FL (US); Belinda De Leon, San Francisco, CA (US)

(73) Assignee: CURNA, INC., Miami, FL (US)

( * ) Notice: Subject to any disclaimer, the term of this patent is extended or adjusted under 35 U.S.C. 154(b) by 0 days.

(21) Appl. No.: 14/741,164

(22) Filed: Jun. 16, 2015

(65) Prior Publication Data

US 2015/0284724 A1 Oct. 8, 2015

Related U.S. Application Data

(62) Division of application No. 13/695,801, filed as application No. PCT/US2011/021052 on Jan. 13, 2011, now Pat. No. 9,089,588.

(60) Provisional application No. 61/415,891, filed on Nov. 22, 2010, provisional application No. 61/412,066, filed on Nov. 10, 2010, provisional application No. 61/409,136, filed on Nov. 2, 2010, provisional application No. 61/330,427, filed on May 3, 2010.

(51) Int. Cl.
*C12N 15/11* (2006.01)
*C12N 15/113* (2010.01)
*A61K 31/7088* (2006.01)

(52) U.S. Cl.
CPC ...... *C12N 15/1137* (2013.01); *A61K 31/7088* (2013.01); *C12N 15/113* (2013.01); *C12N 2310/11* (2013.01); *C12N 2310/111* (2013.01); *C12N 2310/113* (2013.01)

(58) Field of Classification Search
CPC .............. C12N 15/1137; C12N 15/113; C12N 2310/11
See application file for complete search history.

(56) References Cited

U.S. PATENT DOCUMENTS

| 4,683,195 A | 7/1987 | Mullis et al. |
|---|---|---|
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,716,756 A | 2/1998 | Pawlowski et al. |
| 5,728,506 A | 3/1998 | Kometani |
| 5,739,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |
| 5,965,721 A | 10/1999 | Cook et al. |
| 5,985,663 A | 11/1999 | Bennett et al. |
| 6,005,095 A | 12/1999 | Capaccioli et al. |
| 6,013,639 A | 1/2000 | Peyman et al. |
| 6,013,786 A | 1/2000 | Chen et al. |
| 6,034,233 A | 3/2000 | Ecker et al. |

(Continued)

FOREIGN PATENT DOCUMENTS

| CA | 2686933 | 4/2008 |
|---|---|---|
| CN | 101247793 A | 8/2008 |

(Continued)

OTHER PUBLICATIONS

English machine translation of WO 2004/056993, Apr. 2006, 28 pages (Year: 2006).*
Ausubel, Current Protocols in Molecular Biology vol. 1, 1994, 6.0.1-6.4.10.
Barak, et al., "A βArrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).

(Continued)

*Primary Examiner* — Ekaterina Poliakova-Georgantas
(74) *Attorney, Agent, or Firm* — Goodwin Procter LLP

(57) ABSTRACT

The present invention relates to antisense oligonucleotide that modulate the expression of and/or function of a Sirtuin (SIRT), in particular, by targeting natural antisense polynucleotides of a Sirtuin (SIRT). The invention also relates to the identification of these antisense oligonucleotides and their use in treating diseases and disorders associated with the expression of Sirtuins (SIRT)s.

17 Claims, 14 Drawing Sheets

Specification includes a Sequence Listing.

(56) References Cited

U.S. PATENT DOCUMENTS

| | | | |
|---|---|---|---|
| 6,100,090 A | 8/2000 | Monia et al. | |
| 6,140,492 A | 10/2000 | Morelli et al. | |
| 6,147,200 A | 11/2000 | Manoharan et al. | |
| 6,165,712 A | 12/2000 | Foulkes et al. | |
| 6,165,990 A | 12/2000 | Singh et al. | |
| 6,175,409 B1 | 1/2001 | Nielsen et al. | |
| 6,221,587 B1 | 4/2001 | Ecker et al. | |
| 6,239,265 B1 | 5/2001 | Cook | |
| 6,242,589 B1 | 6/2001 | Cook et al. | |
| 6,268,490 B1 | 7/2001 | Imanishi et al. | |
| 6,303,374 B1 | 10/2001 | Zhang et al. | |
| 6,307,040 B1 | 10/2001 | Cook et al. | |
| 6,316,198 B1 | 11/2001 | Skouv et al. | |
| 6,335,434 B1 | 1/2002 | Guzaev et al. | |
| 6,376,541 B1 | 4/2002 | Nixon et al. | |
| 6,403,566 B1 | 6/2002 | Wang | |
| 6,444,464 B1 | 9/2002 | Wyatt | |
| 6,451,991 B1 | 9/2002 | Martin et al. | |
| 6,525,191 B1 | 2/2003 | Ramassamy | |
| 6,528,262 B1 | 3/2003 | Gilad et al. | |
| 6,528,631 B1 | 3/2003 | Cook et al. | |
| 6,617,122 B1 | 9/2003 | Hayden et al. | |
| 6,617,442 B1 | 9/2003 | Crooke et al. | |
| 6,630,315 B1 | 10/2003 | Miwa et al. | |
| 6,639,059 B1 | 10/2003 | Kochkine et al. | |
| 6,656,730 B1 | 12/2003 | Manoharan | |
| 6,667,337 B2 | 12/2003 | Wilson | |
| 6,670,461 B1 | 12/2003 | Wengel et al. | |
| 6,710,174 B2 | 3/2004 | Bennett et al. | |
| 6,734,291 B2 | 5/2004 | Kochkine et al. | |
| 6,762,169 B1 | 7/2004 | Manoharan | |
| 6,794,499 B2 | 9/2004 | Wengel et al. | |
| 6,833,361 B2 | 12/2004 | Hong et al. | |
| 6,861,514 B2 | 3/2005 | Cook et al. | |
| 6,867,294 B1 | 3/2005 | Sanghvi et al. | |
| 6,936,467 B2 | 8/2005 | Kmiec et al. | |
| 6,936,593 B1 | 8/2005 | Agrawal et al. | |
| 6,977,295 B2 | 12/2005 | Belotserkovskii et al. | |
| 6,986,988 B2 | 1/2006 | Gilad et al. | |
| 7,034,133 B2 | 4/2006 | Wengel et al. | |
| 7,034,145 B2 | 4/2006 | Shen et al. | |
| 7,053,195 B1 | 5/2006 | Goff | |
| 7,053,199 B2 | 5/2006 | Imanishi et al. | |
| 7,053,207 B2 | 5/2006 | Wengel | |
| 7,060,809 B2 | 6/2006 | Wengel et al. | |
| 7,084,125 B2 | 8/2006 | Wengel | |
| 7,087,589 B2 | 8/2006 | Jacobson et al. | |
| 7,125,982 B1 | 10/2006 | Frayne | |
| 7,144,995 B2 | 12/2006 | Wise et al. | |
| 7,144,999 B2 | 12/2006 | Ward et al. | |
| 7,148,204 B2 | 12/2006 | Bennett et al. | |
| 7,153,954 B2 | 12/2006 | Koch et al. | |
| 7,169,916 B2 | 1/2007 | Krotz et al. | |
| 7,199,107 B2 | 4/2007 | Dobie et al. | |
| 7,202,357 B2 | 4/2007 | Crooke et al. | |
| 7,217,572 B2 | 5/2007 | Ward et al. | |
| 7,220,549 B2 | 5/2007 | Buzby | |
| 7,226,785 B2 | 6/2007 | Kmiec et al. | |
| 7,229,974 B2 | 6/2007 | Peyman et al. | |
| 7,229,976 B2 | 6/2007 | Dobie et al. | |
| 7,235,534 B2 | 6/2007 | Tauguay et al. | |
| 7,235,653 B2 | 6/2007 | Bennett et al. | |
| 7,238,858 B2 | 7/2007 | Marraccini et al. | |
| 7,276,599 B2 | 10/2007 | Moore et al. | |
| 7,285,288 B1 | 10/2007 | Tormo et al. | |
| 7,297,786 B2 | 11/2007 | McCray et al. | |
| 7,314,923 B2 | 1/2008 | Kaneko et al. | |
| 7,320,965 B2 | 1/2008 | Sah et al. | |
| 7,321,828 B2 | 1/2008 | Cowsert et al. | |
| 7,335,764 B2 | 2/2008 | Crooke et al. | |
| 7,335,765 B2 | 2/2008 | Kaneko et al. | |
| 7,339,051 B2 | 3/2008 | Crooke et al. | |
| 7,371,833 B1 | 5/2008 | Weiss | |
| 7,374,927 B2 * | 5/2008 | Palma | C12Q 1/6883 435/287.2 |
| 7,399,845 B2 | 7/2008 | Seth et al. | |
| 7,402,434 B2 | 7/2008 | Newman et al. | |
| 7,402,574 B2 | 7/2008 | Iversen et al. | |
| 7,420,050 B2 | 9/2008 | Park et al. | |
| 7,423,142 B2 | 9/2008 | Vornlocher | |
| 7,425,545 B2 | 9/2008 | Crooke et al. | |
| 7,427,675 B2 | 9/2008 | Capaldi et al. | |
| 7,456,154 B2 | 11/2008 | Soreq et al. | |
| 7,462,642 B2 | 12/2008 | Wang et al. | |
| 7,468,431 B2 | 12/2008 | Bhanot et al. | |
| 7,510,830 B2 | 3/2009 | Baguley et al. | |
| 7,541,344 B2 | 6/2009 | Bhat et al. | |
| 7,547,684 B2 | 6/2009 | Seth et al. | |
| 7,569,575 B2 | 8/2009 | Sorensen et al. | |
| 7,569,686 B1 | 8/2009 | Bhat et al. | |
| 7,572,582 B2 | 8/2009 | Wengel et al. | |
| 7,582,745 B2 | 9/2009 | Sah et al. | |
| 7,585,893 B2 | 9/2009 | Baguley et al. | |
| 7,589,190 B2 | 9/2009 | Westergaard et al. | |
| 7,598,227 B2 | 10/2009 | Crooke et al. | |
| 7,605,251 B2 | 10/2009 | Tan et al. | |
| 7,622,453 B2 | 11/2009 | Frieden et al. | |
| 7,662,948 B2 | 2/2010 | Kurreck et al. | |
| 7,666,854 B2 | 2/2010 | Seth et al. | |
| 7,674,895 B2 | 3/2010 | Reich et al. | |
| 7,687,617 B2 | 3/2010 | Thrue et al. | |
| 7,691,995 B2 | 4/2010 | Zamore et al. | |
| 7,695,902 B2 | 4/2010 | Crooke | |
| 7,696,345 B2 | 4/2010 | Allerson et al. | |
| 7,709,456 B2 | 5/2010 | Corey et al. | |
| 7,709,630 B2 | 5/2010 | Gaarde et al. | |
| 7,713,738 B2 | 5/2010 | Hansen et al. | |
| 7,718,629 B2 | 5/2010 | Bamcrot et al. | |
| 7,723,508 B2 | 5/2010 | Crooke et al. | |
| 7,732,422 B2 | 6/2010 | Gleave et al. | |
| 7,732,590 B2 | 6/2010 | Bhanot et al. | |
| 7,737,264 B2 | 6/2010 | Thrue et al. | |
| 7,737,265 B2 | 6/2010 | Akinc et al. | |
| 7,741,305 B2 | 6/2010 | Crooke et al. | |
| 7,741,309 B2 | 6/2010 | Hansen et al. | |
| 7,741,457 B2 | 6/2010 | Seth et al. | |
| 7,745,609 B2 | 6/2010 | Bennett et al. | |
| 7,749,978 B2 | 7/2010 | Sah et al. | |
| 9,089,588 B2 | 7/2015 | Collard et al. | |
| 10,000,752 B2 | 6/2018 | Collard et al. | |
| 10,563,202 B2 | 2/2020 | Collard et al. | |
| 10,934,546 B2 | 3/2021 | Collard et al. | |
| 2003/0139359 A1 | 7/2003 | Dobie | |
| 2003/0165831 A1 * | 9/2003 | Lee | A61P 15/08 435/6.11 |
| 2003/0186920 A1 | 10/2003 | Sirois | |
| 2003/0191075 A1 | 10/2003 | Cook et al. | |
| 2003/0228618 A1 | 12/2003 | Levanon et al. | |
| 2003/0233670 A1 | 12/2003 | Edgerton et al. | |
| 2004/0006031 A1 | 1/2004 | Dean et al. | |
| 2004/0014051 A1 * | 1/2004 | Brown-Driver | C12N 15/1135 435/6.14 |
| 2004/0033480 A1 | 2/2004 | Wong | |
| 2004/0101858 A1 | 5/2004 | Ward et al. | |
| 2004/0137423 A1 | 7/2004 | Hayden et al. | |
| 2004/0138155 A1 | 7/2004 | Baird et al. | |
| 2004/0175803 A1 | 9/2004 | Meritet et al. | |
| 2004/0180336 A1 | 9/2004 | Gilad et al. | |
| 2004/0254137 A1 | 12/2004 | Ackermann et al. | |
| 2005/0009771 A1 | 1/2005 | Levanon et al. | |
| 2005/0026160 A1 | 2/2005 | Allerson et al. | |
| 2005/0100885 A1 * | 5/2005 | Crooke | C07K 16/10 435/5 |
| 2005/0113326 A1 | 5/2005 | Siwkowski et al. | |
| 2005/0118625 A1 * | 6/2005 | Mounts | B82Y 30/00 435/6.14 |
| 2005/0143357 A1 | 6/2005 | Pousette et al. | |
| 2005/0153286 A1 | 7/2005 | Clements | |
| 2005/0215504 A1 | 9/2005 | Bennett et al. | |
| 2005/0221354 A1 * | 10/2005 | Mounts | C12Q 1/6876 435/6.11 |
| 2005/0222029 A1 | 10/2005 | Bartel et al. | |
| 2005/0246794 A1 * | 11/2005 | Khvorova | A61K 31/713 800/286 |

(56) References Cited

U.S. PATENT DOCUMENTS

| | | |
|---|---|---|
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0082848 A1 | 4/2007 | Alitalo et al. |
| 2007/0099830 A1 | 5/2007 | Guarente et al. |
| 2007/0134655 A1 | 6/2007 | Bentwich |
| 2007/0197459 A1 | 8/2007 | Milner |
| 2007/0213274 A1 | 9/2007 | Salonen |
| 2007/0213292 A1 | 9/2007 | Stoffel et al. |
| 2007/0231816 A1 | 10/2007 | Chaussabel et al. |
| 2007/0248590 A1 | 10/2007 | Milne et al. |
| 2008/0146788 A1 | 6/2008 | Bhat et al. |
| 2008/0221051 A1 | 9/2008 | Becker et al. |
| 2008/0293142 A1 | 11/2008 | Liu et al. |
| 2009/0117543 A1 | 5/2009 | Sinclair |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0215178 A1 | 8/2009 | Tang |
| 2009/0258925 A1 | 10/2009 | Wahlestedt |
| 2009/0270332 A1* | 10/2009 | Bare .......... A61K 31/4365 514/9.1 |
| 2009/0318536 A1 | 12/2009 | Freier et al. |
| 2009/0326041 A1 | 12/2009 | Bhanot et al. |
| 2010/0105760 A1 | 4/2010 | Collard et al. |

FOREIGN PATENT DOCUMENTS

| | | |
|---|---|---|
| CN | 101437933 A | 5/2009 |
| EP | 335451 A3 | 3/1988 |
| EP | 335451 A2 | 10/1989 |
| JP | 2009-521934 A | 6/2009 |
| JP | 2013-500017 A | 1/2013 |
| JP | 2015-221044 A | 12/2015 |
| WO | WO-1984/03564 | 9/1984 |
| WO | WO-1991/19735 | 12/1991 |
| WO | WO-1992/00091 | 1/1992 |
| WO | WO-1992/08796 | 5/1992 |
| WO | WO-1993/20242 | 10/1993 |
| WO | 9422864 A1 | 10/1994 |
| WO | WO-1994-026887 A1 | 11/1994 |
| WO | WO-1994/28143 | 12/1994 |
| WO | WO-1995-015373 A2 | 6/1995 |
| WO | WO-1995/22618 | 8/1995 |
| WO | WO-1995/25116 | 10/1995 |
| WO | WO-1995/35505 | 12/1995 |
| WO | WO-1996-027663 A2 | 9/1996 |
| WO | WO-1997-039120 A1 | 10/1997 |
| WO | WO-1999-014226 A1 | 3/1999 |
| WO | WO-1999-039352 A1 | 8/1999 |
| WO | WO-2000-057837 A1 | 10/2000 |
| WO | WO-2000-061770 A2 | 10/2000 |
| WO | WO-2001-000669 A2 | 1/2001 |
| WO | WO-2001-21631 A2 | 3/2001 |
| WO | WO-2001-025488 A2 | 4/2001 |
| WO | WO-2001-051630 A1 | 7/2001 |
| WO | WO-0152865 A1 * | 7/2001 ......... A61K 31/7115 |
| WO | 2001079230 A2 | 10/2001 |
| WO | WO-0179230 A2 * | 10/2001 ......... C12Q 1/6883 |
| WO | 200192524 A2 | 12/2001 |
| WO | WO-2002-062840 A1 | 8/2002 |
| WO | WO-2002-068688 A1 | 9/2002 |
| WO | 2002085308 A2 | 10/2002 |
| WO | WO-02085308 A2 * | 10/2002 ......... A61K 31/122 |
| WO | 2003016500 A2 | 2/2003 |
| WO | 2003/037909 A1 | 5/2003 |
| WO | WO-2004-016255 A1 | 2/2004 |
| WO | WO-2004-024079 A2 | 3/2004 |
| WO | WO-2004-030750 A1 | 4/2004 |
| WO | WO-2004-041838 A1 | 5/2004 |
| WO | WO-2004056993 A1 * | 7/2004 ......... C07K 14/415 |
| WO | WO-2004- 104161 A2 | 12/2004 |
| WO | 2005004814 A1 | 1/2005 |
| WO | WO-2005-045034 A2 | 5/2005 |
| WO | 2005/065997 A1 | 7/2005 |
| WO | 2005/078091 A1 | 8/2005 |
| WO | WO-2005-070136 A2 | 8/2005 |
| WO | WO-2005-079862 A1 | 9/2005 |
| WO | WO-2005108949 A2 * | 11/2005 ......... G01N 33/74 |
| WO | 2006/006171 A2 | 1/2006 |
| WO | 2006/068668 A2 | 6/2006 |
| WO | WO-2007-028065 A2 | 3/2007 |
| WO | WO-2007-071182 A1 | 6/2007 |
| WO | WO-2007-087113 A2 | 8/2007 |
| WO | 2007134014 A2 | 11/2007 |
| WO | WO-2007134014 A2 * | 11/2007 ......... C12N 15/1137 |
| WO | WO-2007-138023 A1 | 12/2007 |
| WO | 2008021290 A2 | 2/2008 |
| WO | WO-2008021290 A2 * | 2/2008 ......... G01N 33/68 |
| WO | WO-2008-042510 A2 * | 4/2008 ......... C12Q 1/6883 |
| WO | WO-2008-057556 A2 | 5/2008 |
| WO | WO-2008-066672 A2 | 6/2008 |
| WO | WO-2008-087561 A2 | 7/2008 |
| WO | 2008/156866 A1 | 12/2008 |
| WO | 2008155390 A2 | 12/2008 |
| WO | 2008158886 A1 | 12/2008 |
| WO | WO-2009099991 A2 * | 8/2009 ......... C12N 15/111 |
| WO | WO-2010-002984 A1 | 1/2010 |
| WO | WO-2010-040571 A2 | 4/2010 |
| WO | WO-2010-054364 A1 | 5/2010 |
| WO | WO-2010-058227 A2 | 5/2010 |
| WO | 2010065862 A2 | 6/2010 |
| WO | 2010102058 A2 | 9/2010 |
| WO | 2011011700 A2 | 1/2011 |
| WO | 2011139387 A1 | 11/2011 |
| WO | 2012087983 A1 | 6/2012 |

OTHER PUBLICATIONS

Baum, "Solid-phase synthesis of benzodiazepines," C&EN News, Jan. 18, p. 33-34 (1993).

Bernstein, E., et al., "Role for a Bidentate Ribonuclease in the Initiation Step of RNA Interference," Nature 409:363-366 (2001).

Boutla, A., et al., "Short 5'-phosphorylated double-stranded RNAs induce RNA interference in *Drosophila*," Curr. Biol. 11:1776-1780 (2001).

Boyd-Kimball, et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).

Brazma & Vilo, "Gene expression data analysis," FEBS Lett., 480:17-24 (2000).

Bright, et al., "Chapter 6. Fluorescence Ratio Imaging Microscopy," Methods in Cell Biology vol. 30, Taylor and Wang (eds) p. 157-192 (1989).

Bright, et al., "Delivery of Macromolecules Into Adherent Cells via Electroporation for Use in Fluorescence Spectroscopic Imaging and Metabolic Studies," Cytometry 24:226-233 (1996).

Bright, et al., "Fluorescence Ratio Imaging Microscopy: Temporal and Spatial Measurements of Cytoplasmic pH," J. Cell Biology 104:1019-1033 (1987).

Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).

Carninci, et al., "The transcriptional landscape of the mammalian genome," Science 309:1559-1563 (2005).

Carulli, et al., "High Throughput Analysis of Differential Gene Expression," J. Cell Biochem. Suppl., 3:286-296 (1998).

Celis, et al., "Gene expression profiling: monitoring transcription and translation products using DNA microarrays and proteomics," FEBS Lett., 480:2-16 (2000).

Chabala, J.C., "Solid-phase combinatorial chemistry and novel tagging methods for identifying leads," Curr Opin Biotechnol. 6:632-639 (1995).

Cech, J., "Ribozymes and Their Medical Implications," American. Med Assoc. 260:3030-3035 (1988).

(56) References Cited

OTHER PUBLICATIONS

Chen, et al., "Expression of ssDNA in Mammalian Cells," BioTechniques 34:167-171 (2003).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Cheng, J. et al., "Transcriptional maps of 10 human chromosomes at 5-nucleotide resolution," Science 308:5725:1149-1154 (2005).
Cho, et al., "An Unnatural Biopolymer," Science 261:1303-1305 (1993).
Christiensen, N.K. et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," J. Am. Chem. Soc., 120:5458-5463 (1998).
Cubitt, et al., "Understanding, improving and using green fluorescent proteins," Trends in Biochemical Science 20:448-455 (1995).
Curiel, D. T. et al., "Adenovirus enhancement of transferrin-polylysine-mediated gene delivery," PNAS 88:8850-8854 (1991).
Dai et al., "SIRT1 Interacts With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet 3:219-223 (1993).
Davis, et al., "Direct Gene Transfer into Skeletal Muscle In Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al., "Anthrax," New England J. Med. 341:815-826 (1999).
Dolle, "Discovery of Enzyme inhibitors through combinatorial chemistry," Mol Divers. 2:223-236 (1997).
Dykxhoorn, D., et al., "Determinants of Specific RNA Interference-Mediated Silencing of Human β-Globin Alleles Differing by a Single Nucleotide Polymorphism," PNAS, vol. 103, No. 15, pp. 5953-5958, (2006).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels, Mol. Cell Neurosci. 33: 227-235 (2006).
Faghihi, M. & Wahlestedt, C., "RNA interference is not involved in natural antisense mediated regulation of gene expression in mammals," Genome Biol (2005), 7: R38.1-R38.9.
Fauchere, et al., "Peptide and nonpeptide lead discovery using robotically synthesized soluble libraries," Can J. Physiol Pharmacol 75:683-689 (1997).
Felgner and Holm, "Cationic Liposome-Mediated Transfection," Bethesda Res. Lab Focus, 11:2:21 (1989).
Fields, et al., "How many genes in the human genome?" Nature Genetics 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).
Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).

Geller, A.I. et al., "An HSV-1 Vector Expressing Tyrosine Hydroxylase Causes Production and Release of L-DOPA from Cultured Rat Striatal Cells," J. Neurochem 64:487-496 (1995).
Geller, A.I. et al., "Long-term increases in neurotransmitter release from neuronal cells expressing a constitutively active adenylate cyclase from a herpes simplex virus type 1 vector," PNAS U.S.A.:90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
GenBank Accession No. NM_000559, Homo Sapiens Hemoglobin, Gamma A (HBG1), mRNA, (2008).
Giuliano, et al., "FLuorescent Protein Biosensors: Measurement of Molecular Dynamics in Living Cells," Ann. Rev. of Biophysics and Biomolecular Structure 24:405-434 (1995).
Giuliano, et al., "Light-Optical-Based Reagents for the Measurement and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Haussecker, D., et al., "Dicer-Dependent Turnover of Intergenic from the Human β-Globin Gene Cluster," Molecular and Cellular Biology, vol. 25, No. 21, pp. 9724-9733, (2005).
Heller, et al., "Discovery and Analysis of Inflammatory Disease-Related Genes Using cDNA Microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomeric chemical diversity," Proc. Nat. Acad. Sci. USA 90;6909-6913 (1993).
Houghton AN, Gold JS, Blachere NE, Immunity against cancer: lessons learned from melanoma,. Curr Opin Immunol 13:134-140 (2001).
International Human Genome Sequencing Consortium "Finishing the euchromatic sequence of the human genome." Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett. 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptome," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).

(56) References Cited

OTHER PUBLICATIONS

Kenan, et al., "Exploring molecular diversity with combinatorial shape libraries," Trends Biochem Sci 19:57-64 (1994).
Kornberg, A., DNA Replication, W.H. Freeman & Co., San Francisco, pp. 75-77, (1980).
Larson, et al., "Rapid DNA Fingerprinting of Pathogens by Flow Cytometry," Cytometry, 2000, 41:203-208 (2000).
Larsson, et al., "High-Throughput Protein Expression of cDNA Products as a Tool in Functional Genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, Properties, and Activity as Inhibitors of Replication of Human Immunodeficiency Virus in Cell Culture," PNAS 86:6553-6556 (1989).
Li et al., "Control of APP processing and Aβ generation level by BACE1 enzymatic activity and transcription," Faseb J 20; 285-292 (2006).
Li, et al., J. Neurochem 89 1308-1312 (2004).
Liang, et al., "Parallel Synthesis and Screening of a Solid Phase Carbohydrate Library," Science 274:1520-1522 (1996).
Luther, "Role of endogenous antisense RNA in cardiac gene regulation," J. Mol. Med. 83:26-32 (2005).
Madden, et al., "Serial analysis of gene expression: from gene discovery to target identification," Drug Discov. Today 5:415-425 (2000).
Makalowska I, Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3651-3654 (1995).
Manoharan, et al., "Chemical Modifications to Improve Uptake and Bioavailability of Antisense Oligonucleotides," Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet 5:4:316-323 (2004).
Maurer, R.A., "Cationic Liposome-Mediated Transfection of Primary Cultures of Rat Pituitary Cells," Bethesda Res. Lab. Focus 11:2:25 (1989).
Mcneil in Methods in Cell Biology vol. 29, Taylor and Wang (eds.) p. 153-173 (1989).
Morelli et al., "The antisense bcl-2-IgH transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser, et al., "Effective incorporation of 2'-O-methyl-oligoribonucleotides into liposomes and enhanced cell association through modification with thiocholesterol," Nucl. Acids Res. 20:533-538 (1992).
Petit et al., "Wild-type PINK1 Prevents Basal and Induced Neuronal Apoptosis, a Protective Effect Abrogated by Parkinson Disease-Related Mutations", Journ. Biol. Chem., vol. 280, No. 40, pp. 34025-334032 (2005).

Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis of Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., in Crooke, S.T. and Lebleu, B., eds., Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shen, T., et al., "Modification of Globin Gene Expression by RNA Targeting Strategies," Experimental Hematology, vol. 35, No. 8, pp. 1209-1218, (2007).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun, et al., "Downregulation of Sirt1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al., "Inhibition of HIV proliferation in MT-4 cells by antisense oligonucleotide conjugated to lipophilic groups," Biochimie 75:49-54 (1993).
Tamango, et al., "The various aggregation states of β-amyloid 1-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).

(56) References Cited

OTHER PUBLICATIONS

Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46 (1994).
Walsh, et al., The role of cell-derived oligomers of Aβ in Alzheimer's disease and avenues for therapeutic intervention, Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer, et al., "Glial cell line-derived neurotrophic factor (GDNP) is a proliferation factor for rat C6 glioma cells: evidence from antisense experiments," Antisense & Nucleic Acid Drug Development 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada, et al., "Endothelial Nitric-Oxide Synthase Antisense (NOS3AS) Gene Encodes an Autophagy-Related Protein (APG9-like2) Highly Expressed in Trophoblast" (2005).
Yang, et al., "Cellular and Humoral Immune Responses to Viral Antigens Create Barriers to Lung-Directed Gene Therapy with Recombinant Adenoviruses," J. Virol 69:2004-2015 (1995).
Yoshigai, et al., "Characterization of Natural Antisense Transcripts Expressed from Interleukin 1β-inducible Genes in Rat Hepatocytes," HOAJ Biology; 1-10 (2012).
EP Application No. 06850393.7 Examination Report dated Oct. 18, 2011.
International Search Report and Written Opinion for PCT Application No. PCT/US2010/033078 dated Jun. 29, 2011.
PCT/US2010/026119 Search Report and Written Opinion dated Feb. 7, 2011.
PCT/US2010/024079 Search Report and Written Opinion dated Jan. 31, 2011.
PCT/US2010/027394 Search Report and Written Opinion dated Nov. 5, 2010.
PCT/US96/10287 (WO97/000271) The Regents of the University of California Jan. 3, 1997.
Carafa, V., et al., "Sirtuins and Disease: The Road Ahead", Frontiers In Pharmacology, vol. 3, No. 4, pp. 1-6, (2012).
Collard, J., et al., "Treatment of Sirtuin (Sirt) Related Diseases by Inhibition of Natural Antisense Transcript to Sirtuin (Sirt)", JP2015-221044 (A), Espacenet, (2015). Abstract.
Collard, J., et al., "Treatment of Sirtuin (Sirt) Related Diseases by Inhibition of Natural Antisense Transcript to a Sirtuin (Sirt)", JP2013-500017 (A), Espacenet, (2013). Abstract.
Database Accession No. PREV200900197869, Kuebacher, A., et al., "MicroRNA 92a Controls Vessel Growth and Functional Recovery After Ischemia", Database Biosis, Biosciences Information Service, (2008), Abstract.
Dias, N., GenBank Accession No. BE164357, "RC4-HT0469-130200-013-g09 HT0469 *Homo sapiens* cDNA, mRNA Sequence", (2000).
Erion, D., et al., "Sirt 1 Knockdown in Liver Decreases Basal Hepatic Glucose Production and Increases Hepatic Insulin Responsiveness in Diabetic Rats", Proceedings of the National Academy of Sciences, vol. 106, No. 27, pp. 11288-1193, (2009).
Ford, E., et al., "Mammalian Sir2 Homolog SIRT7 is an Activator of RNA Polymerase I Transcription", Genes & Development, vol. 20, No. 9, pp. 1075-1080, (2006).
Frye, R., "Phylogenetic Classification of Prokaryotic and Eukaryotic Sir2-like Proteins", Biochemical and Biophysical Research Communications vol. 273, No. 2, pp. 793-798, (2000). Abstract.
GenBank Accession No. AK031466.1, "Mus Musculus 13 Days Embryo Male Testis cDNA, RIKEN Full-Length Enriched Library, Clone:6030437B01 Product: Synembryn, Full Insert Sequence", (2008).
GenBank Accession No. AL136935.1, "*Homo sapiens* mRNA; cDNA DKFZp586O0222 (from clone DKFZp586O0222)", (2001).
GenBank Accession No. 8Q028712.1, "UI-1-EE0-ayz-I-10-0-UI.s1 NCI_CGAP_PI7 *Homo sapiens* cDNA Clone UI-1-EE0-ayz-I-10-0-UI 3-, mRNA Sequence", (2002).
GenBank Accession No. BQ024738, "UI-1-BB1p-atr-e-09-0-UI.s1 NCI_CGAP_PI6 *Homo sapiens* cDNA Clone UI-1-BB1p-atr-e-09-0-UI 3-, mRNA Sequence", (2002).
GenBank Accession No. DA645474.1, "DA645474 LYMPB2 *Homo sapiens* cDNA Clone LYMPB2002688 5-, mRNA Sequence", (2005).
Guan, D., et al., "Deacetylation of the Tumor Suppressor Protein PML Regulates Hydrogen Peroxide-Induced Cell Death", Cell Death and Disease, vol. 5, pp. 1-13, (2014).
Haigis, M., et al., "SIRT4 Inhibits Glutamate Dehydrogenase and Opposes the Effects of Calorie Restriction in Pancreatic B Cells", Cell, vol. 126, No. 5, pp. 941-954, (2006).
Nasrin, N., et al., "SIRT4 Regulates Fatty Acid Oxidation and Mitochondrial Gene Expression in Liver and Muscle Cells", The Journal of Biological Chemistry, vol. 285, No. 42, pp. 31995-32002, (2010).
Paredes, S., et al., "Molecular Pathways: Emerging Roles of Mammalian Sirtuin SIRT7 in Cancer", Clinical Cancer Research, vol. 20, No. 7, pp. 1741-1746, (2014).
Parikh, S., et al., "A Modern Approach to the Treatment of Mitochondrial Disease", Current Treatment Options Neurology, vol. 11, No. 6, pp. 414-430, (2009).
Pillai, V., et al., "Mitochondrial SIRT3 and Heart Disease", Cardiovascular Research, vol. 88, pp. 250-256, (2010).
Potente, M., et al., "SIRT1 Controls Endothelial Angiogenic Functions During Vascular Growth", Gene & Development, vol. 21, pp. 2644-2658, (2007).
Sadhukhan, S., et al., "Metabolomics-Assisted Proteomics Identifies Succinylation and SIRT5 as Important Regulators of Cardiac Function", Proceedings of the National Academy of Sciences, vol. 113, No. 16, pp. 4320-4325, (2016).
Sinclair, D., et al., CN1012477793 A, "Compositions for Treating or Preventing Obesity and Insulin Resistance Disorders", (2008). Abstract.
Smalheiser, N., et al., "Natural Antisense Transcripts are Co-Expressed with Sense mRNAs in Synaptoneurosomes of Adult Mouse Forebrain" Neuroscience Research, vol. 62, pp. 236-239, (2008).
Sun, Y., et al., "Downregulation of Sirt1 by Antisense Oligonucleotides Induces Apoptosis and Enhances Radiation Sensitization in A549 Lung Cancer Cells", Lung Cancer, vol. 58, No. 1, pp. 21-29, (2007). Abstract.
Tang, X., et al., "SIRT7 antagonizes TGF-β Signaling and Inhibits Breast Cancer Metastasis", Nature Communications, vol. 8, No. 318, pp. 1-14, (2017).

(56) References Cited

OTHER PUBLICATIONS

Thimmappa, S., et al., "Neuronal Protection by Sirtuins in Alzeheimer's Disease", Journal of Neurochemistry, vol. 96, No. 2, pp. 305-313, (2006).
Tillman, L., et al., "Oral Delivery of Antisense Oligonucleotides in Man", Journal of Pharmaceuticals Sciences, vol. 97, No. 1, pp. 225-236, (2008).
Wahlestedt, C., "Natural Antisense and Non-Coding RNA Transcripts as Drug Targets", JP2009521934 (A), Espacenet, (2009). Abstract.
Weir, H., et al., "SIRT3: A Central Regulator of Mitochondrial Adaptation in Health and Disease", Genes and Cancer, vol. 4, No. 3-4, pp. 118-124, (2013).
Westphal, C., et al., A Therapeutic Role for Sirtuins in Diseases of Aging?, Science Direct, vol. 32, No. 12, pp. 555-550, (2007).
Yamamoto, H., et al., "Sirtuin Functions in Health and Disease" Molecular Endocrinology, vol. 21, No. 8, pp. 1745-1755, (2007).
Bonauer, A., et al., "MicroRNA-92a Controls Angiogenesis And Functional Recovery of Ischemic Tissue In Mice", Science, vol. 324, No. 5935, pp. 1710-1713, (2009).
GenBank Accession No. NM_002359.2, "*Homo sapiens* V-Maf Masculoaponeurotic Fibrosarcoma Oncogene Homolog G (Avian) (MAFG), Transcript Variant 1, mRNA Sequence", (2010).
Huang, J., et al., "Mitochondrial Sirtuins", Biochimica At Biophysica Acta, vol. 1804, No. 8, pp. 1645-1651, (2010).
Lavu, S., et al., "Sirtuins, Novel Therapeutic Targets to Treat Age-Associated Diseases", Nature Review, Drug Discover, vol. 7, No. 10, pp. 841-853, (2008).
Schumacker, P., "A Tumor Suppressor SIRTainty", Cancer Cell, vol. 17, No. 1, pp. 5-6, (2010).
Swindell, W., "Genes and Gene Expression Modules Associated With Caloric with Restriction and Aging in the Laboratory Mouse", BMC Genomics, vol. 10, No. 1, pp. 1-28, (2009).
Yoo, H., et al., "Glutamine Reliance in Cell Metabolism" Experimental & Molecular Medicine, vol. 52, pp. 1496-1516, (2020).
PCT/US2011/021052—International Search Report, dated Jan. 13, 2011.
Kuehbacher, A., et al., "MicroRNA 92a Controls Vessel Growth and Functional Recovery After Ischemia," American Heart Association, Inc., Circulation, vol. 118:S.sub.-550, (2008). Abstract.
Bonauer, A., et al., "Supporting Online Material for MicroRNA-92a Controls Angiogenesis and Functional Recovery of Ischemic Tissues in Mice," Science, Retrived from http://www.sciencemag.org/contents/suppl/2009/05/21/1174381.DC1/Bonauer.s-ub.-SOM.pdf, pp. 1-35, (2009).
Anekonda, T., at al., "Neuronal Protection by Sirtuins in Alzheimer's Disease," Journal of Neurochemistry, vol. 96, No. 2, pp. 305-313, (2006).
Dai, Y., et al., "SIRT 1 is Required for Antagonist-Induced Transcriptional Repression of Androgen-Responsive Genes by the Androgen Receptor," Mol Endocrinol., vol. 21, No. 6, pp. 1-23, (2007).
Outeiro, T., et al., "Sirtuin 2 Inhibitors Rescue a-Synuclein-Mediated Toxicity in Models of Parkinson's Disease," Science, vol. 317, No. 5837, pp. 516-519, (2007).
Yamakuchi, M., et al., "mlR-34a Repression of SIRT1 Regulates Apoptosis," PNAS, vol. 105, No. 36, pp. 13421-13426, (2008).
GenBank Accession No. DQ278604, *Homo sapiens* Sirtuin (Silent Mating Type Information Regulation 2 Homolog, SIRT1, (2005).
Berg et al., "*Homo sapiens* v-maf musculoaponeurotic fibrosarcoma oncogene homolog G (avian) (MAFG), transcript variant 1, mRNA," GenBank NCBI Reference Sequence: NM_002359.2, accessed May 18, 2021, 3 pages.
Ahuja et al., "Regulation of insulin secretion by SIRT4, a mitochondrial ADP-ribosyltransferase." Journal of Biological Chemistry 282, No. 46 (2007): 33583-33592.
Braasch et al., "Novel antisense and peptide nucleic acid strategies for controlling gene expression." Biochemistry 41, No. 14 (2002): 4503-4510.
Ford et al., "Mammalian Sir2 homolog SIRT7 is an activator of RNA polymerase I transcription." Genes & development 20, No. 9 (2006): 1075-1080.
Gertz et al., "Function and regulation of the mitochondrial Sirtuin isoform Sirt5 in Mammalia." Biochimica et Biophysica Acta (BBA)—Proteins and Proteomics 1804, No. 8 (2010): 1658-1665.
"Sirtuins", Moi Compass, 4, Nov. 1, 2001, found in the Internet on Jun. 6, 2016, http://moikimpas.ru/compas/sirtuin.
Sergeev, ed., "A Short Course in Molecular Pharmacology," Ministry of Pyublic Health of the RSFSR and N.I Pirogov Moscow Medical Institute, Moscow, 1975, pp. 10-11. ("A reference in Russian").
Kholodov et al., "Clinical pharmacokinetics." Chapter 3, Drug Absorption, Meditsina, Moscow (1985): 83-89. ("A reference in Russian").
Treschalina et al., "Guidelinse fo rhte Study of the Antitumor Activity of Pharmacological Substances," 2000, pp. 319-320. ("A reference in Russian").
Rane et al., "Downregulation of miR-199a derepresses hypoxia-inducible factor-1a and Sirtuin 1 and recapitulates hypoxia preconditioning in cardiac myocytes." Circulation research 104, No. 7 (2009): 879-886.
Vakhrusheva et al., "Sirt7 increases stress resistance of cardiomyocytes and prevents apoptosis and inflammatory cardiomyopathy in mice." Circulation research 102, No. 6 (2008): 703-710.
PCT/US2011/021052—International Preliminary Report on Patentability, dated Nov. 6, 2012, 9 pages.
PCT/US2011/021052—International Search Report, dated Oct. 19, 2011, 7 pages.

\* cited by examiner

Fold difference in SIRT mRNA copy number after treatment with oligo against SIRTas compared to control Fold difference in mRNA copy number compared to control Fold difference in mRNA copy # compared to control Fold difference in mRNA copy # compared to controls Fold difference in mRNA copy # compared to control Fold difference in mRNA copy # compared to controls

SEQUENCE LISTING

```
<160> NUMBER OF SEQ ID NOS: 145

<210> SEQ ID NO 1
<211> LENGTH: 4110
<212> TYPE: DNA
<213> ORGANISM: Homo sapiens
<300> PUBLICATION INFORMATION:
<308> DATABASE ACCESSION NUMBER: NM_012238.4
<309> DATABASE ENTRY DATE: 2011-01-03
<313> RELEVANT RESIDUES IN SEQ ID NO: (1)..(4110)

<400> SEQUENCE: 1
gtcgagcggg agcagaggag gcgagggagg agggccagag aggcagttgg aagatggcgg        60
acgaggcggc cctcgccctt cagcccggcg gctcccctc ggcggcgggg gccgacaggg        120
aggccgcgtc gtcccccgcc ggggagccgc tccgcaagag gccgcggaga gatggtcccg        180
```

```
gcctcgagcg gagcccgggc gagcccggtg gggcggcccc agagcgtgag gtgccggcgg    240
cggccagggg ctgcccgggt gcggcggcgg cggcgctgtg gcgggaggcg gaggcagagg    300
cggcggcggc aggcggggag caagaggccc aggcgactgc ggcggctggg gaaggagaca    360
atgggccggg cctgcaggge ccatctcggg agccaccgct ggccgacaac ttgtacgacg    420
aagacgacga cgacgagggc gaggaggagg aagaggcggc ggcggcggcg attgggtacc    480
gagataacct tctgttcggt gatgaaatta tcactaatgg ttttcattcc tgtgaaagtg    540
atgaggagga tagagcctca catgcaagct ctagtgactg gactccaagg ccacggatag    600
gtccatatac ttttgttcag caacatctta tgattggcac agatcctcga caattcttaa   660
aagatttatt gccggaaaca atacctccac ctgagttgga tgatatgaca ctgtggcaga    720
ttgttattaa tatcctttca gaaccaccaa aaaggaaaaa agaaaaagat attaatacaa    780
ttgaagatgc tgtgaaatta ctgcaagagt gcaaaaaaat tatagttcta actggagctg    840
gggtgtctgt ttcatgtgga atacctgact tcaggtcaag ggatggtatt tatgctcgcc    900
ttgctgtaga cttcccagat cttccagatc tcaagcgat gtttgatatt gaatatttca    960
gaaaagatcc aagaccattc ttcaagtttg caaggaaat atatcctgga caattccagc   1020
catctctctg tcacaaattc atagccttgt cagataagga aggaaaacta cttcgcaact   1080
atacccagaa catagacacg ctggaacagg ttgcgggaat ccaaaggata attcagtgtc   1140
atggttcctt tgcaacagca tcttgcctga tttgtaaata caagttgac tgtgaagctg    1200 tacgaggaga tattttttaat caggtagttc ctcgatgtcc taggtgccca gctgatgaac   1260
cgcttgctat catgaaacca gagattgtgt ttttggtga aaatttacca gaacagtttc    1320
atagagccat gaagtatgac aaagatgaag ttgacctcct cattgttatt gggtcttccc    1380
tcaaagtaag accagtagca ctaattccaa gttccatacc ccatgaagtg cctcagatat   1440
taattaatag agaacctttg cctcatctgc attttgatgt agagcttctt ggagactgtg   1500
atgtcataat taatgaattg tgtcataggt taggtggtga atatgccaaa ctttgctgta    1560
accctgtaaa gctttcagaa attactgaaa aacctccacg aacacaaaaa gaattggctt   1620
atttgtcaga gttgccaccc acacctcttc atgtttcaga agactcaagt tcaccagaaa   1680
gaacttcacc accagattct tcagtgattg tcacactttt agaccaagca gctaagagta   1740
atgatgattt agatgtgtct gaatcaaaag gttgtatgag agaaaaacca caggaagtac   1800
aaacttctag gaatgttgaa agtattgctg aacagatgga aaatccggat ttgaagaatg    1860
ttggttctag tactggggag aaaaatgaaa gaacttcagt ggctgaaaca gtgagaaaat   1920
gctggcctaa tagagtggca aaggagcaga ttagtaggcg gcttgatggt aatcagtatc    1980 tgttttgcc accaaatcgt tacatttttcc atggcgctga ggtatattca gactctgaag    2040
atgacgtctt atcctctagt tcttgtggca gtaacagtga tagtgggaca tgccagagtc   2100
caagtttaga agaacccatg gaggatgaaa gtgaaattga agaattctac aatggcttag   2160
aagatgagcc tgatgttcca gagagagctg gaggagctgg atttgggact gatggagatg    2220
atcaagaggc aattaatgaa gctatatctg tgaaacagga agtaacagac atgaactatc   2280
catcaaacaa atcatagtgt aataattgtg caggtacagg aattgttcca ccagcattag    2340
gaactttagc atgtcaaaat gaatgtttac ttgtgaactc gatagagcaa ggaaaccaga   2400
aaggtgtaat atttataggt tggtaaaata gattgttttt catggataat ttttaacttc    2460
attatttctg tacttgtaca aactcaacac taactttttt ttttttaaaa aaaaaaggt    2520
```

| | |
|---|---|
| actaagtatc ttcaatcagc tgttggtcaa gactaacttt cttttaaagg ttcatttgta | 2580 |
| tgataaattc atatgtgtat atataatttt ttttgttttg tctagtgagt ttcaacattt | 2640 |
| ttaaagtttt caaaaagcca tcggaatgtt aaattaatgt aaagggaaca gctaatctag | 2700 |
| accaaagaat ggtattttca cttttctttg taacattgaa tggtttgaag tactcaaaat | 2760 |
| ctgttacgct aaacttttga ttctttaaca caattatttt taaacactgg cattttccaa | 2820 |
| aactgtggca gctaactttt taaaatctca aatgacatgc agtgtgagta aaggaagtc | 2880 |
| aacaatatgt ggggagagca ctcggttgtc tttacttta aaagtaatac ttggtgctaa | 2940 |
| gaatttcagg attattgtat ttacgttcaa atgaagatgg cttttgtact tcctgtggac | 3000 |
| atgtagtaat gtctatattg gctcataaaa ctaacctgaa aaacaaataa atgctttgga | 3060 |
| aatgtttcag ttgctttaga aacattagtg cctgcctgga tcccttagt tttgaaatat | 3120 |
| ttgccattgt tgtttaaata cctatcactg tggtagagct tgcattgatc ttttccacaa | 3180 |
| gtattaaact gccaaaatgt gaatatgcaa agcctttctg aatctataat aatggtactt | 3240 |
| ctactgggga gagtgtaata ttttggactg ctgttttcca ttaatgagga gagcaacagg | 3300 |
| cccctgatta tacagttcca aagtaataag atgttaattg taattcagcc agaaagtaca | 3360 |
| tgtctcccat tgggaggatt tggtgttaaa taccaaactg ctagccctag tattatggag | 3420 |
| atgaacatga tgatgtaact tgtaatagca gaatagttaa tgaatgaaac tagttcttat | 3480 |
| aatttatctt tatttaaaag cttagcctgc cttaaaacta gagatcaact ttctcagctg | 3540 |
| caaaagcttc tagtctttca agaagttcat actttatgaa attgcacagt aagcatttat | 3600 |
| ttttcagacc atttttgaac atcactccta aattaataaa gtattcctct gttgctttag | 3660 |
| tatttattac aataaaaagg gtttgaaata tagctgttct ttatgcataa acacccagc | 3720 |
| taggaccatt actgccagag aaaaaaatcg tattgaatgg ccatttccct acttataaga | 3780 |
| tgtctcaatc tgaatttatt tggctacact aaagaatgca gtatatttag ttttccattt | 3840 |
| gcatgatgtt tgtgtgctat agatgatatt ttaaattgaa aagtttgttt taaattattt | 3900 |
| ttacagtgaa gactgttttc agctctttt atattgtaca tagtcttta tgtaatttac | 3960 |
| tggcatatgt tttgtagact gtttaatgac tggatatctt ccttcaactt ttgaaataca | 4020 |
| aaaccagtgt tttttacttg tacactgttt taaagtctat taaaattgtc atttgacttt | 4080 |
| tttctgttaa cttaaaaaaa aaaaaaaaaa | 4110 |

<210> SEQ ID NO 2
<211> LENGTH: 3806
<212> TYPE: DNA
<213> ORGANISM: Mus musculus
<300> PUBLICATION INFORMATION:
<308> DATABASE ACCESSION NUMBER: NM_001159589.1
<309> DATABASE ENTRY DATE: 2010-07-18
<313> RELEVANT RESIDUES IN SEQ ID NO: (1)..(3806)

<400> SEQUENCE: 2

| | |
|---|---|
| gccagtgccg cgcgtcgagc ggagcagagg aggcgagggc ggagggccag agaggcagtt | 60 |
| ggaagatggc ggacgaggtg gcgctcgccc ttcaggccgc cggctcccct tccgcggcgg | 120 |
| ccgccatgga ggccgcgtcg cagcggcgg acgagccgct ccgcaagagg ccccgccgag | 180 |
| acgggcctgg cctcgggcgc agcccgggcg agccgagcgc agcagtggcg ccggcggccg | 240 |
| cggggtgtga ggcggcgagc gccgcggccc cggcggcgct gtggcgggag gcggcagggg | 300 |
| cggcggcgag cgcggagcgg gaggcccccg cgacggccgt ggccggggac ggagacaatg | 360 |
| ggtccggcct gcggcgggag ccgagggcgg ctgacgactt cgacgacgac gagggcgagg | 420 |

```
aggaggacga ggcggcggcg gcagcggcgg cggcagcgat cggctaccga ggtccatata    480
cttttgttca gcaacatctc atgattggca ccgatcctcg aacaattctt aaagatttat    540
taccagaaac aattcctcca cctgagctgg atgatatgac gctgtggcag attgttatta    600
atatcctttc agaaccacca aagcggaaaa aagaaaaga tatcaataca attgaagatg     660
ctgtgaagtt actgcaggag tgtaaaaaga taatagttct gactggagct ggggtttctg    720
tctcctgtgg gattcctgac ttcagatcaa gagacggtat ctatgctcgc cttgcggtgg    780
acttcccaga cctcccagac cctcaagcca tgtttgatat tgagtatttt agaaaagacc    840
caagaccatt cttcaagttt gcaaaggaaa tatatcccgg acagttccag ccgtctctgt    900
gtcacaaatt catagctttg tcagataagg aaggaaaact acttcgaaat tatactcaaa    960
atatagatac cttggagcag gttgcaggaa tccaaaggat ccttcagtgt catggttcct   1020
ttgcaacagc atcttgcctg atttgtaaat acaagttga ttgtgaagct gttcgtggag    1080
acatttttaa tcaggtagtt cctcggtgcc ctaggtgccc agctgatgag ccacttgcca   1140
tcatgaagcc agagattgtc ttctttggtg aaaacttacc agaacagttt catagagcca   1200
tgaagtatga caaagatgaa gttgacctcc tcattgttat tggatcttct ctgaaagtga   1260
gaccagtagc actaattcca agttctatac cccatgaagt gcctcaaata ttaataaata   1320 gggaacctt gcctcatcta cattttgatg tagagctcct tggagactgc gatgttataa    1380
ttaatgagtt gtgtcatagg ctaggtggtg aatatgccaa actttgttgt aaccctgtaa   1440
agctttcaga aattactgaa aaacctccac gcccacaaaa ggaattggtt catttatcag   1500
agttgccacc aacacctctt catatttcgg aagactcaag ttcacctgaa agaactgtac   1560
cacaagactc ttctgtgatt gctacacttg tagaccaagc aacaaacaac aatgttaatg   1620
atttagaagt atctgaatca agttgtgtgg aagaaaaacc acaagaagta cagactagta   1680
ggaatgttga gaacattaat gtggaaaatc cagattttaa ggctgttggt tccagtactg   1740
cagacaaaaa tgaaagaact tcagttgcag aaacagtgag aaaatgctgg cctaatagac   1800
ttgcaaagga gcagattagt aagcggcttg agggtaatca atcctgtttt gtaccaccaa   1860
atcgttacat attccacggt gctgaggtat actcagactc tgaagatgac gtcttgtcct   1920
ctagttcctg tggcagtaac agtgacagtg gcacatgcca gagtccaagt ttagaagaac   1980
ccttggaaga tgaaagtgaa attgaagaat tctacaatgg cttggaagat gatacggaga   2040
ggcccgaatg tgctggagga tctggatttg gagctgatgg aggggatcaa gaggttgtta   2100
atgaagctat agctacaaga caggaattga cagatgtaaa ctatccatca gacaaatcat   2160
aacactattg aagctgtccg gattcaggaa ttgctccacc agcatgggga actttagcat   2220 gtcaaaaat gaatgtttac ttgtgaactt gaacaaggaa atctgaaaga tgtattattt    2280
atagactgga aaatagattg tcttcttgga taatttctaa agttccatca tttctgtttg   2340
tacttgtaca ttcaacactg ttggttgact tcatcttcct ttcaaggttc atttgtatga   2400
tacattcgta tgtatgtata attttgtttt ttgcctaatg agtttcaacc ttttaaagtt   2460
ttcaaaagcc attggaatgt taatgtaaag ggaacagctt atctagacca agaatggta    2520 tttcacactt ttttgtttgt aacattgaat agtttaaagc cctcaattc tgttctgctg    2580 aacttttatt tttaggacag ttaactttt aaacactggc attttccaaa acttgtggca    2640
gctaactttt taaaatcaca gatgacttgt aatgtgagga gtcagcaccg tgtctggagc   2700
actcaaaact tggtgctcag tgtgtgaagc gtacttactg catcgttttt gtacttgctg   2760
```

| | |
|---|---|
| cagacgtggt aatgtccaaa caggccnctg agactaatct gataaatgat ttggaaatgt | 2820 |
| gtttcagttg ttctagaaac aatagtgcct gtctatatag gtccccttag tttgaatatt | 2880 |
| tgccattgtt taattaaata cctatcactg tggtagagcc tgcatagatc ttcaccacaa | 2940 |
| atactgccaa gatgtgaata tgcaaagcct ttctgaatct aataatggta cttctactgg | 3000 |
| ggagagtgta atattttgga ctgctgtttt tccattaatg aggaaagcaa taggcctctt | 3060 |
| aattaaagtc ccaaagtcat aagataaatt gtagctcaac cagaaagtac actgttgcct | 3120 |
| gttgaggatt tggtgtaatg tatcccaagg tgttagcctt gtattatgga gatgaataca | 3180 |
| gatccaatag tcaaatgaaa ctagttctta gttatttaaa agcttagctt gccttaaaac | 3240 |
| tagggatcaa ttttctcaac tgcagaaact tttagccttt caaacagttc acacctcaga | 3300 |
| aagtcagtat ttattttaca gacttctttg gaacattgcc cccaaattta aatattcatg | 3360 |
| tgggtttagt atttattaca aaaaaatgat ttgaaatata gctgttcttt atgcataaaa | 3420 |
| tacccagtta ggaccattac tgccagagga gaaaagtatt aagtagctca tttccctacc | 3480 |
| taaaagataa ctgaatttat ttggctacac taaagaatgc agtatattta gttttccatt | 3540 |
| tgcatgatgt gtttgtgcta tagacaatat tttaaattga aaaatttgtt ttaaattatt | 3600 |
| tttacagtga agactgtttt cagctctttt tatattgtac atagacttttt atgtaatctg | 3660 |
| gcatatgttt tgtagaccgt ttaatgactg gattatcttc ctccaacttt tgaaatacaa | 3720 |
| aaacagtgtt ttatacttgt atcttgtttt aaagtcttat attaaaattg tcatttgact | 3780 |
| tttttcccgt taaaaaaaaa aaaaaa | 3806 |

<210> SEQ ID NO 3
<211> LENGTH: 2086
<212> TYPE: DNA
<213> ORGANISM: Homo sapiens
<300> PUBLICATION INFORMATION:
<308> DATABASE ACCESSION NUMBER: NM_012237.3
<309> DATABASE ENTRY DATE: 2010-12-25
<313> RELEVANT RESIDUES IN SEQ ID NO: (1)..(2086)

<400> SEQUENCE: 3

| | |
|---|---|
| cattttccgg gcgccctta ccaacatggc tgctgacgcc acgccttctg ggactcgtag | 60 |
| tccggtcctc gcgcgctttc ttacctaact ggggcgctct gggtgttgta cgaaagcgcg | 120 |
| tctgcggccg caatgtctgc tgagagttgt agttctgtgc cctatcacgg ccactcccat | 180 |
| ttctggtgcc gtcacgggac agagcagtcg gtgacaggac agagcagtcg gtgacgggac | 240 |
| acagtggttg gtgacgggac agagcggtcg gtgacagcct caagggcttc agcaccgcgc | 300 |
| ccatggcaga gccagacccc tctcaccctc tggagaccca ggcagggaag gtgcaggagg | 360 |
| ctcaggactc agattcagac tctgagggag gagccgctgg tggagaagca gacatggact | 420 |
| tcctgcggaa cttattctcc cagacgctca gcctgggcag ccagaaggag cgtctgctgg | 480 |
| acgagctgac cttggaaggg gtggcccggt acatgcagag cgaacgctgt cgcagagtca | 540 |
| tctgtttggt gggagctgga atctccacat ccgcaggcat cccgactttt cgctctccat | 600 |
| ccaccggcct ctatgacaac ctagagaagt accatcttcc ctacccagag gccatctttg | 660 |
| agatcagcta tttcaagaaa catccggaac ccttcttcgc cctcgccaag gaactctatc | 720 |
| ctgggcagtt caagccaacc atctgtcact acttcatgcg cctgctgaag acaagggggc | 780 |
| tactcctgcg ctgctacacg cagaacatag atacccggga gcgaatagcc gggctggaac | 840 |
| aggaggactt ggtggaggcg cacggcacct tctacacatc acactgcgtc agcgccagct | 900 |
| gccggcacga ataccccgcta agctggatga agagaagat cttctctgag gtgacgccca | 960 |

```
agtgtgaaga ctgtcagagc ctggtgaagc ctgatatcgt cttttttggt gagagcctcc      1020
cagcgcgttt cttctcctgt atgcagtcag acttcctgaa ggtggacctc ctcctggtca      1080
tgggtacctc cttgcaggtg cagcccttg cctccctcat cagcaaggca ccctctcca       1140 cccctcgcct gctcatcaac aaggagaaag ctggccagtc ggacccttc ctggggatga       1200 ttatgggcct cggaggaggc atggactttg actccaagaa ggcctacagg acgtggcct       1260 ggctgggtga atgcgaccag ggctgcctgg cccttgctga gctccttgga tggaagaagg      1320
agctggagga ccttgtccgg agggagcacg ccagcataga tgcccagtcg ggggcggggg      1380
tccccaaccc cagcacttca gcttcccca agaagtcccc gccacctgcc aaggacgagg       1440
ccaggacaac agagagggag aaaccccagt gacagctgca tctcccaggc gggatgccga      1500
gctcctcagg gacagctgag ccccaaccgg gcctggcccc ctcttaacca gcagttcttg      1560
tctggggagc tcagaacatc ccccaatctc ttacagctcc ctccccaaaa ctggggtccc      1620
agcaaccctg gccccaacc ccagcaaatc tctaacacct cctagaggcc aaggcttaaa       1680
caggcatctc taccagcccc actgtctcta accactcctg ggctaaggag taacctccct      1740
catctctaac tgcccccacg gggccagggc tacccccagaa cttttaactc ttccaggaca     1800
gggagcttcg ggccccact ctgtctcctg ccccgggg cctgtggcta agtaaaccat         1860
acctaaccta ccccagtgtg ggtgtgggcc tctgaatata acccacaccc agcgtagggg      1920
gagtctgagc cgggagggct cccgagtctc tgccttcagc tcccaaagtg ggtggtgggc      1980
ccccttcacg tgggacccac ttcccatgct ggatgggcag aagacattgc ttattggaga     2040
caaattaaaa acaaaaacaa ctaacaatcc ggaaaaaaaa aaaaaa                     2086

<210> SEQ ID NO 4
<211> LENGTH: 2919
<212> TYPE: DNA
<213> ORGANISM: Homo sapiens
<300> PUBLICATION INFORMATION:
<308> DATABASE ACCESSION NUMBER: NM_012239
<309> DATABASE ENTRY DATE: 2010-07-04
<313> RELEVANT RESIDUES IN SEQ ID NO: (1)..(2919)
<300> PUBLICATION INFORMATION:
<308> DATABASE ACCESSION NUMBER: NM_012239.5
<309> DATABASE ENTRY DATE: 2010-07-04
<313> RELEVANT RESIDUES IN SEQ ID NO: (1)..(2919)

<400> SEQUENCE: 4
gcgagtccgg aggactcctt ggactgcgcg gaacatggcg ttctggggtt ggcgcgccgc       60
ggcagccctc cggctgtggg gccgggtagt tgaacgggtc gaggccgggg gaggcgtggg      120 gccgttcag gcctgcggct gtcggctggt gcttggcggc agggacgatg tgagtgcggg       180
gctgagaggc agccatgggg cccgcggtga gcccttggac ccggcgcgcc ccttgcagag      240
gcctcccaga cccgaggtgc ccagggcatt ccggaggcag ccgagggcag cagctcccag      300
tttcttcttt tcgagtatta aaggtggaag aaggtccata tcttttttctg tgggtgcttc     360 aagtgttgtt ggaagtggag gcagcagtga caaggggaag ctttccctgc aggatgtagc      420
tgagctgatt cgggccagag cctgccagag ggtggtggtc atggtgggg ccggcatcag       480 cacacccagt ggcattccag acttcagatc gccgggagag ggcctgtaca gcaacctcca     540
gcagtacgat ctcccgtacc ccgaggccat ttttgaactc ccattcttct ttcacaaccc      600
caagcccttt tcactttgg ccaaggagct gtaccctgga aactacaagc ccaacgtcac       660
tcactacttt ctccggctgc ttcatgacaa ggggctgctt ctgcggctct acacgcagaa      720
```

```
catcgatggg cttgagagag tgtcgggcat ccctgcctca aagctggttg aagctcatgg      780
aacctttgcc tctgccacct gcacagtctg ccaaagaccc ttcccagggg aggacattcg      840
ggctgacgtg atggcagaca gggttccccg ctgcccggtc tgcaccggcg ttgtgaagcc      900
cgacattgtg ttctttgggg agccgctgcc ccagaggttc ttgctgcatg tggttgattt      960
ccccatggca gatctgctgc tcatccttgg gacctccctg gaggtggagc cttttgccag     1020
cttgaccgag gccgtgcgga gctcagttcc ccgactgctc atcaaccggg acttggtggg     1080
gcccttggct tggcatcctc gcagcaggga cgtggcccag ctggggacg tggttcacgg      1140 cgtggaaagc ctagtggagc ttctgggctg acagaagag atgcgggacc ttgtgcagcg      1200
ggaaactggg aagcttgatg gaccagacaa ataggatgat ggctgccccc acacaataaa     1260
tggtaacata ggagacatcc acatcccaat tctgacaaga cctcatgcct gaagacagct     1320
tgggcaggtg aaaccagaat atgtgaactg agtggacacc cgaggctgcc actggaatgt     1380
cttctcaggc catgagctgc agtgactggt agggctgtgt ttacagtcag gccaccccg      1440 tcacatatac aaaggagctg cctgcctgtt tgctgtgttg aactcttcac tctgctgaag     1500
ctcctaatgg aaaaagcttt cttctgactg tgaccctctt gaactgaatc agaccaactg     1560
gaatcccaga ccgagtctgc tttctgtgcc tagttaacg gcaagctcgg catctgttgg      1620
ttacaagatc cagacttggg ccgagcggtc cccagccctc ttcatgttcc gaagtgtagt     1680
cttgaggccc tggtgccgca cttctagcat gttggtctcc tttagtgggg ctattttaa      1740 tgagagaaaa tctgttcttt ccagcatgaa atacatttag tctcctcaaa gggactgcag     1800
gtgttgacat gagttggaaa gggaaccctg ggatacgtgg cgtcccctct attggaacag     1860
tctgaggact gaaggcattt gtccctggat ttattggaga cggcccagct cctccctctg     1920
aaggtggtca cattctgttg actctccata ctcagcctct cctccagaaa cagatctgtt     1980
ccagaacatt ccagcacttt ctatctggcc tccttgtccc cacactacgc cccccaccc      2040 tcgccagggc ttcctctagt gacactgtta gagctaatct ctgagacagg gaaggcatta    2100
ctcacttaaa acccaggctg agtcctggcc acctgctgga ttgtgacata ggaggtggaa    2160
tccactgaac tgctacttct gcacaggctc cttctcctgg ggctgtaccc aggcccagcc    2220
ctgatggctc accctgtcag gcaccagctg ctccctcctg ggctctcacc cacctgcaca    2280
tcctccttcc tagcatcaca ttacctgcgt gtttccccag acaaaagcac ttcccattct    2340
tgaaccttgc ctaccctggg ctgagctgac ggcaatagat ttaatgacag tgactcccag    2400 gaaggggggtc ctgtgacttt gcgccttaat aagaacaaaa ggtggaattg gtgacctagg   2460
aaaactgttg aattctaaaa agaatgaagt tagtttctaa ccctagttaa tgttcctttt    2520 ttatttttg agtcttgccc tgtcactcag ggtggagtgc ggtgttatga tctcagctca    2580
ctgcaacttc cgcctcccgg gtttaagcga ttctcctggg tagctgggat tacaggtgtg    2640
tcccaccaca cctagcacat gggcatattt gtaatagaga caaggttttg ctatgttggc    2700
caggctggtc tcgaactcct ggcttcaagt gatccaccca cctcggcctc ccaaagtgct    2760
gggattacag gcatgagcca ctgtgcctgg ccccttttatt tgataattta cacatacatt    2820
tttgtccaaa actcttcttt atttcaagat gatgtttctg tggctatgtg tggtatgtgg    2880
tataaatctc aatctatggt caaaaaaaaa aaaaaaaaa                             2919
```

<210> SEQ ID NO 5
<211> LENGTH: 1213
<212> TYPE: DNA
<213> ORGANISM: Homo sapiens <300> PUBLICATION INFORMATION:
<308> DATABASE ACCESSION NUMBER: NM_012240
<309> DATABASE ENTRY DATE: 2010-12-26
<313> RELEVANT RESIDUES IN SEQ ID NO: (1)..(1213)

<400> SEQUENCE: 5

| | | | | | |
|---|---|---|---|---|---|
| gcaaatgcaa | tcagacggtc | ccactgtggg | gtgtgaagtg | tccgtagagc | tgtgagagaa | 60 |
| tgaagatgag | ctttgcgttg | actttcaggt | cagcaaaagg | ccgttggatc | gcaaacccca | 120 |
| gccagccgtg | ctcgaaagcc | tccattgggt | tatttgtgcc | agcaagtcct | cctctggacc | 180 |
| ctgagaaggt | caagagttca | gcgcttca | tcacccttc | caagagactc | cttgtgatga | 240 |
| ctggggcagg | aatctccacc | gaatcgggga | taccagacta | caggtcagaa | aaagtggggc | 300 |
| tttatgcccg | cactgaccgc | aggcccatcc | agcatggtga | ttttgtccgg | agtgccccaa | 360 |
| tccgccagcg | gtactgggcg | agaaacttcg | taggctggcc | tcaattctcc | tcccaccagc | 420 |
| ctaaccctgc | acactgggct | tgagcacct | gggagaaact | cggaaagctg | tactggttgg | 480 |
| tgacccaaaa | tgtggatgct | ttgcacacca | aggcggggag | tcggcgcctg | acagagctcc | 540 |
| acggatgcat | ggacagggtc | ctgtgcttgg | attgtgggga | acagactccc | cgggggtgc | 600 |
| tgcaagagcg | tttccaagtc | ctgaacccca | cctggagtgc | tgaggcccat | ggcctggctc | 660 |
| ctgatggtga | cgtctttctc | tcagaggagc | aagtccggag | ctttcaggtc | ccaacctgcg | 720 |
| ttcaatgtgg | aggccatctg | aaaccagatg | tcgtttct | cggggacaca | gtgaaccctg | 780 |
| acaaggttga | ttttgtgcac | aagcgtgtaa | agaagccga | ctccctcttg | gtggtgggat | 840 |
| catccttgca | ggtatactct | ggttacaggt | ttatcctcac | tgcctgggag | aagaagctcc | 900 |
| cgattgcaat | actgaacatt | gggcccacac | ggtcggatga | cttggcgtgt | ctgaaactga | 960 |
| attctcgttg | tggagagttg | ctgcctttga | tagacccatg | ctgaccacag | cctgatattc | 1020 |
| cagaacctgg | aacagggact | ttcacttgaa | tcttgctgct | aaatgtaaat | gccttctcaa | 1080 |
| atgacagatt | ccagttccca | ttcaacagag | tagggtgcac | tgacaaagta | tagaaggttc | 1140 |
| taggtatctt | aatgtgtgga | tattcttaat | taaaactcat | ttttttaa | taaaaaattg | 1200 |
| ttcagcttta | aaa | | | | | 1213 |

<210> SEQ ID NO 6
<211> LENGTH: 3927
<212> TYPE: DNA
<213> ORGANISM: Homo sapiens
<300> PUBLICATION INFORMATION:
<308> DATABASE ACCESSION NUMBER: NM_012241
<309> DATABASE ENTRY DATE: 2010-12-20
<313> RELEVANT RESIDUES IN SEQ ID NO: (1)..(3927)

<400> SEQUENCE: 6

| | | | | | |
|---|---|---|---|---|---|
| ccggagcgcg | gtcgggacac | agcgcctcta | ggagaaagcc | tggaaggcgc | tccgggggta | 60 |
| cccagagctc | ttagcgggcc | ggcagcatgt | gcggggccca | agtaaatgga | aatgttttct | 120 |
| aacatataaa | aacctacaga | agaagaaaat | aattttctgg | atcaaattag | aagtctgtat | 180 |
| tatattgatg | tctccagatt | caaatatatt | agaaagcagc | cgtggagaca | accatcttca | 240 |
| ttttgggaga | aataactaaa | gcccgcctca | agcattagaa | ctacagacaa | accctgatgc | 300 |
| gacctctcca | gattgtccca | gtcgattga | tttcccagct | atattgtggc | ctgaagcctc | 360 |
| cagcgtccac | acgaaaccag | atttgcctga | aaatggctcg | gccaagttca | gtatggcag | 420 |
| attttcgaaa | gtttttgca | aaagcaaagc | acatagtcat | catctcagga | gctggtgtta | 480 |
| gtgcagaaag | tggtgttccg | accttcagag | gagctggagg | ttattggaga | aaatggcaag | 540 |

```
cccaggacct ggcgactccc ctggcctttg cccacaaccc gtcccgggtg tgggagttct    600
accactaccg gcgggaggtc atggggagca aggagcccaa cgccgggcac cgcgccatag    660
ccgagtgtga gacccggctg ggcaagcagg gccggcgagt cgtggtcatc acccagaaca    720
tcgatgagct gcaccgcaag gctggcacca agaaccttct ggagatccat ggtagcttat    780
ttaaaactcg atgtacctct tgtggagttg tggctgagaa ttacaagagt ccaatttgtc    840
cagctttatc aggaaaaggt gctccagaac ctggaactca agatgccagc atcccagttg    900
agaaacttcc ccggtgtgaa gaggcaggct gcggggcctt gctgcgacct cacgtcgtgt    960
ggtttggaga aaacctggat cctgccattc tggaggaggt tgacagagag ctcgcccact   1020
gtgatttatg tctagtggtg ggcacttcct ctgtggtgta cccagcagcc atgtttgccc   1080
cccaggtggc tgccagggc gtgccagtgg ctgaatttaa cacggagacc accccagcta   1140
cgaacagatt caggtttcat ttccagggac cctgtggaac gactcttcct gaagcccttg   1200
cctgtcatga aaatgaaact gtttcttaag tgtcctgggg aagaaagaaa ttacagtata   1260
tctaagaact aggccacacg cagaggagaa atggtcttat gggtggtgag ctgagtactg   1320
aacaatctaa aaatagcctc tgattccctc gctggaatcc aacctgttga taagtgatgg   1380
gggtttagaa gtagcaaaga gcacccacat tcaaaagtca cagaactgga aagttaattc   1440
atattatttg gtttgaactg aaacgtgagg tatctttgat gtgtatggtt ggttattggg   1500
agggaaaaat tttgtaaatt agattgtcta aaaaaaatag ttattctgat tatattttg    1560
ttatctgggc aaagtagaag tcaaggggta aaaaccctac tattctgatt tttgcacaag   1620
ttttagtgga aaataaaatc acactctaca gtaggtaatt tattgtataa agacattacc   1680
ccacgatatg gctttattag ggactttttt ttttttttt tgagacagag tttcactctt   1740
gttgcccagc tggagtgca gtggtgcgat ctcagctcac agcaacctcc gcctcccggg   1800
ttcaagagat tctcctgcct cagcctcatg agtagctggg attacaggta tgtaccacca   1860
cacccagcta attttgtatt tttagtagag acggggtttc tccatgttgg tcaggctggt   1920
cttaaactct cgacctcagg tgatctgccc gcctcggcct cccaaagtgc tgagattacg   1980
ggcatgagcc accgcacccg gcttactggg ggcttttaa ccttgtttgg ctacattacc   2040
tcagtgaaca aggggaagct cacaacagga actcacacaa agaaggaaga gaacagtacc   2100
aacaaggtag aacatcacga tgagaagaaa gaatgatgca aatatgtgga ccccccaggat   2160
aaacacagct gcccaaaatt tagctctggc ccccttagat gggggaagtc aacagtgaag   2220
tgtttctcag catcataaag gcagaagctg tggttcctgt ggggcctgcc aaccgttccc   2280
agatgctgaa ctctgctggg agttttttcc atgggacttt aaaaaatgat gcccttaggt   2340
tgggccagac ctctgttaac ttcagtaggg atggcaccag gttcaagagg ccaaagaaga   2400
gacctggagc tagtgaagga aacatagggt ttatttgggg aaccttacag ggtggtccag   2460
tggccgcggg ctggacagaa ctgcaaccac ttataaaaag catgcagttt acatagcact   2520
ttcactcagc accctcccct cagcagcctc cacgtggcaa ccctcacttc ttaagttatt   2580
gctgtcagat gcatctgcca tacagggtca ttctcagggg atgcttaagt tatttctgtc   2640
aggtacatct tccatacact ttactacctt ggagtaaagt agtaagaata cagctttttc   2700
cttaaccttt accagctaac tcagtgctta ggggccttgg aatgcctgct gtccagcagg   2760
tgtcacaggc ctgactggga ggcatggcca ttatcaacag tgtatgaagg tcacatatgg   2820
ctccctgaag tgattacata cttggaccac atcacctcag ccccttgcaa aattgcattt   2880
aatgttacac ccttggcttt tgtagaaaca ggcaacaaga cactatcata taaaactttg   2940
```

| | | |
|---|---|---|
| tactgcattg caaggcataa ccttttaataa atcccagtgg tcctttgtgt agggaacggg | 3000 |
| gatgctcata gcctatgggg cggctggaga accagtcagg gaccctgagg gctcgatgta | 3060 |
| cactttacat gggtgggcca aggagtttac actgagggca ctggtaatac ctgtaatagt | 3120 |
| cttatagtac ttataaagca gttttgcaca taaaatacca tcatgcactt ataagtttgt | 3180 |
| tcttgggctg ctccaagtta actttattca ttttcctagt gttagtgtct cagggagtct | 3240 |
| gattatattt ttgatttgta atttctatct gactaaggcc tagagatttc aaaactgttc | 3300 |
| tttgcaattc ctctcatact gaacctctgg ttcagcagct ttttttgttg ttgttgtttt | 3360 |
| caagttttat cattttgtt cctatttggt tttgtcgttt ttaaattgag aattgcttct | 3420 |
| aaaacagaag acatgaaaag agaattaaaa atacaatata tgtgtaagat agaattattc | 3480 |
| aacttagcat ttattaaaca tctaccagat gatagacatt agaaataaaa tgactagcaa | 3540 |
| gacctggccc ttcccctcag gggttcacag aatggctgga gcaactgtca tataagctgt | 3600 |
| tatgaagtgc agaaactaca cagacatttg tgcgggttca gaccagcgca attagagatg | 3660 |
| ggcagagtgg gatggggtag gggtaaggtg cttgaaattt gcctgggtgg gaattttga | 3720 |
| agtataaaaa ggacttctac ctgggggggct gcggcagtag agggaagagc acggtcggta | 3780 |
| caaatgcatg gcaggtgtga aacagtttga tttgttcaaa gaatgatgaa tcacttagtg | 3840 |
| ttgtataatg gatgggagga gagaaacaca gcgatcacaa agggccatgt ttgccaagaa | 3900 |
| ataaaatata cttggaaaaa aaaaaaa | 3927 |

<210> SEQ ID NO 7
<211> LENGTH: 1657
<212> TYPE: DNA
<213> ORGANISM: Homo sapiens
<300> PUBLICATION INFORMATION:
<308> DATABASE ACCESSION NUMBER: NM_016539
<309> DATABASE ENTRY DATE: 2010-07-17
<313> RELEVANT RESIDUES IN SEQ ID NO: (1)..(1657)

<400> SEQUENCE: 7

| | | |
|---|---|---|
| gcttccggcg gaagcggcct caacaaggga aactttattg ttcccgtggg gcagtcgagg | 60 |
| atgtcggtga attacgcggc ggggctgtcg ccgtacgcgg acaagggcaa gtgcggcctc | 120 |
| ccggagatct tcgacccccc ggaggagctg gagcggaagg tgtgggaact ggcgaggctg | 180 |
| gtctggcagt cttccagtgt ggtgttccac acgggtgccg gcatcagcac tgcctctggc | 240 |
| atccccgact tcaggggtcc ccacggagtc tggaccatgg aggagcgagg tctggccccc | 300 |
| aagttcgaca ccacctttga gagcgcgcgg cccacgcaga cccacatggc gctggtgcag | 360 |
| ctggagcgcg tgggcctcct ccgcttcctg gtcagccaga acgtggacgg gctccatgtg | 420 |
| cgctcaggct tccccaggga caaactgcca gagctccacg ggaacatgtt tgtggaagaa | 480 |
| tgtgccaagt gtaagacgca gtacgtccga gacacagtcg tgggcaccat gggcctgaag | 540 |
| gccacgggcc ggctctgcac cgtggctaag gcaagggggc tgcgagcctg caggggagag | 600 |
| ctgagggaca ccatcctaga ctgggaggac tccctgcccg accgggacct ggcactcgcc | 660 |
| gatgaggcca gcaggaacgc cgacctgtcc atcacgctgg gtacatcgct gcagatccgg | 720 |
| cccagcggga acctgccgct ggctaccaag cgccggggag gccgcctggt catcgtcaac | 780 |
| ctgcagccca ccaagcacga ccgccatgct gacctccgca tccatggcta cgttgacgag | 840 |
| gtcatgaccc ggctcatgaa gcacctgggg ctggagatcc ccgcctggga cggccccgt | 900 |
| gtgctggaga gggcgctgcc acccctgccc cgcccgccca ccccaagct ggagcccaag | 960 |

| | |
|---|---:|
| gaggaatctc ccacccggat caacggctct atccccgccg gccccaagca ggagccctgc | 1020 |
| gcccagcaca acggctcaga gcccgccagc cccaaacggg agcggcccac cagccctgcc | 1080 |
| ccccacagac ccccaaaag ggtgaaggcc aaggcggtcc ccagctgacc agggtgcttg | 1140 |
| gggagggtgg ggcttttgt agaaactgtg gattcttttt ctctcgtggt ctcactttgt | 1200 |
| tacttgtttc tgtccccggg agcctcaggg ctctgagagc tgtgctccag gccaggggtt | 1260 |
| acacctgccc tccgtggtcc ctccctgggc tccaggggcc tctggtgcgg ttccgggaag | 1320 |
| aagccacacc ccagaggtga caggtgagcc cctgccacac cccagcctct gacttgctgt | 1380 |
| gttgtccaga ggtgaggctg ggccctccct ggtctccagc ttaaacagga gtgaactccc | 1440 |
| tctgtcccca gggcctccct tctgggcccc ctacagccca ccctacccct cctccatggg | 1500 |
| ccctgcagga ggggagaccc accttgaagt gggggatcag tagaggcttg cactgccttt | 1560 |
| ggggctggag ggagacgtgg gtccaccagg cttctggaaa agtcctcaat gcaataaaaa | 1620 |
| caatttcttt cttgcaaaaa aaaaaaaaaa aaaaaa | 1657 |

<210> SEQ ID NO 8
<211> LENGTH: 1749
<212> TYPE: DNA
<213> ORGANISM: Homo sapiens
<300> PUBLICATION INFORMATION:
<308> DATABASE ACCESSION NUMBER: NM_016538
<309> DATABASE ENTRY DATE: 2010-07-18
<313> RELEVANT RESIDUES IN SEQ ID NO: (1)..(1749)

<400> SEQUENCE: 8

| | |
|---|---:|
| cgcggcctgc cgtgtgaggc ggaagcggaa gagcaggtct ccaggggagc gatggcagcc | 60 |
| gggggtctga gccgctccga gcgcaaagcg gcggagcggg tccggaggtt gcgggaggag | 120 |
| cagcagaggg agcgcctccg ccaggtgtcg cgcatcctga ggaaggcggc ggcggagcgc | 180 |
| agcgccgagg agggccggct gctggccgag agcgcggacc tggtaacgga gctgcagggc | 240 |
| cggagccggc ggcgcgaggg cctgaagcgg cggcaggagg aggtgtgcga cgacccggag | 300 |
| gagctgcggg ggaaggtccg ggagctggcc agcgccgtcc ggaacgccaa atacttggtc | 360 |
| gtctacacag gcgcgggaat cagcacggca gcgtctatcc cagactaccg gggccctaat | 420 |
| ggagtgtgga cactgcttca gaaagggaga agcgttagtg ctgccgacct gagcgaggcc | 480 |
| gagccaaccc tcacccacat gagcatcacc cgtctgcatg agcagaagct ggtgcagcat | 540 |
| gtggtgtctc agaactgtga cgggctccac ctgaggagtg ggctgccgcg cacggccatc | 600 |
| tccgagctcc acgggaacat gtacattgaa gtctgtacct cctgcgttcc caacagggag | 660 |
| tacgtgcggg tgttcgatgt gacggagcgc actgccctcc acagacacca gacaggccgg | 720 |
| acctgccaca gtgtgggac ccagctgcgg gacaccattg tgcactttgg ggagaggggg | 780 |
| acgttggggc agcctttgaa ctgggaagcg gcgaccgagg ctgccagcag agcagacacc | 840 |
| atcctgtgtc tagggtccag cctgaaggtt ctaaagaagt acccacgcct ctggtgcatg | 900 |
| accaagcccc ctagccggcg gccgaagctt tacatcgtga acctgcagtg gaccccgaag | 960 |
| gatgactggg ctgccctgaa gctacatggg aagtgtgatg acgtcatgcg gctcctcatg | 1020 |
| gccgagctgg gcttggagat ccccgcctat agcaggtggc aggatcccat tttctcactg | 1080 |
| gcgactcccc tgcgtgctgg tgaagaaggc agccacagtc ggaagtcgct gtgcagaagc | 1140 |
| agagaggagg ccccgcctgg ggaccggggt gcaccgctta gctcggcccc catcctaggg | 1200 |
| ggctggtttg gcaggggctg cacaaaacgc acaaaaagga agaaagtgac gtaatcacgt | 1260 |
| gctcgatgaa gaacagttgg cactttgcag atggccagtg tcacggtgaa ggctgggttg | 1320 |

```
cccccacggg tctagggaga acgaactctt tggggatgac attttcaccg tgacattttt    1380
agccatttgt ccttgaggaa gccccttgca ctgctgcggt tgtaccctga tacggcctgg    1440
ccatcgagga cacctgccca tccggcctct gtgtcaagag gtggcagccg cacctttctg    1500
tgagaacgga actcgggtta tttcagcccc ggcctgcaga gtggaagcgc ccagcggcct    1560
ttcctcgctc accaggccag tctcagggcc tcaccgtatt tctactacta cttaatgaaa    1620
aagtgtgaac tttatagaat cctctctgta ctggatgtgc ggcagagggg tggctccgag    1680
cctcggctct atgcagacct ttttatttct attaaacgtt tctgcactgg caaaaaaaaa    1740
aaaaaaaaa                                                            1749

<210> SEQ ID NO 9
<211> LENGTH: 1028
<212> TYPE: DNA
<213> ORGANISM: Homo sapiens

<400> SEQUENCE: 9
cttttcactt gtgaatacca attaggtttc cagtttctca taaagatcta acaaataccc      60
aatttctcca tcagactgac atcccttaac aaaagcagag tttcaattcc ctgcatctcc    120
tttaggagct atgatataat gtaggtagaa atcttgcctt aactccattt acccactgtg    180
ctataaataa gcagaagcaa atattttttt aaggctggag aggttttaaa aatctgaact    240
aatttagcaa ctgctgctgc actcagtttt tggcagttcc caaacatcca ttatcatgta    300
aggataaatc cttctaaacc agaaaaatgt ttcctacttg gaaaaggcat aagaaaatac    360
atatacgacc tccccatgta ctagtcttac ataccccagc tccagttaga actataattt    420
ttttgcactc ttgcagtaat ttcacagcat cttcaattgt attaatatct tttctttttt    480
tccttttggg tggttctgaa aggatattaa taacaatctg ccacagtgtc atatcatcca    540
actcaggtgg aggtattgtt tccggcaata aatctttaag aattgttcga ggatctgtgc    600
caatcataag atgttgctga acaaaagtat atggacctac aataagggggg aaaaggctta    660 aagtcaactt atcaagtaat tcaaaatctc atttattttc tgaagtaatg agttagcatt    720
ctgtgagggt ttttgcaaa gtaagaaaat gcaatttaat ggtatttcat tctcggtaca    780
ctcagaatta atgctatatc ccaatgagat taggaagatc taatgaagag ttgggaagac    840 cccctttcagc tgtaagtata tatttcaaga gtctaattaa ttaacaacca gaattaagtt    900
cttatggtta atatctagaa acacacacca taataccaaa agtatttaca aaagggttct    960
acgacataga aaaatcgtac cagtcctaaa agcctgtact acttatcatt aaaaccacac   1020
aggaaaaa                                                            1028

<210> SEQ ID NO 10
<211> LENGTH: 429
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
```

```
<400> SEQUENCE: 10
cgacganaac ataagcactt ttaatttcct ctctattatg ctacagacaa ggccgaagac    60 tgggttttt  aggttgttta aggctgtaaa gaaaacaaag aacatatgac agagaccta    120 tgcagtctgc aaagcatact acatatttac taccaggccc taccttacta cagaaagttt   180
gctgatccag ctgtgaacat atacccgat gcagatgaaa acaaatacaa aacaaaccta    240
acttgccatt ttggtcacaa gagcaagtaa gtagcagagc cctgttttga tatgaaaatc   300
cagcactgga ctgggcaaca tggcgagacc ccatctctac caaaaatact aaaaaaatag   360
ccgggcatgg tgnggcacat ctgtagtact agctacttgn gaggctgaga caggagaatc   420
atttgagcc                                                          429

<210> SEQ ID NO 11
<211> LENGTH: 508
<212> TYPE: DNA
<213> ORGANISM: Homo sapiens

<400> SEQUENCE: 11
gaagaagaag cagccatgat gataggtgat agatccgaaa taatggccac atttgttaac    60 attttttccat ttctaaacca tccttaaaga aaatcatagt atggggtcac accatcctca   120
cggtagtcca atagagcaac catgccatct ggattcatgt tttcaccaat aaagaactgg   180 tagttttga  aattagcaag gatgtgcttg atttgttctg cagcccctgt cataaaaggt    240
tatactcttt ctggtctctg ttcttcaagt ttcccttga  ttgatttcat gtaatctttg    300
atgtacttct tgtaggcttc ttttcatatt tccgaaagct tagtgttggg aagagtaaca   360
gattcctacc ttccctccat attaattaag atgatgtgat tgtggcgact tgacattttc   420
tatttgatct accttagggt tgcagctaat tagttaccta agactattgc atagtgtgtg   480
tatatacagg cttctttca tatttccg                                      508

<210> SEQ ID NO 12
<211> LENGTH: 593
<212> TYPE: DNA
<213> ORGANISM: Homo sapiens
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t

<400> SEQUENCE: 12
tctcactgtc tcccaggctg gagcgcaatg gtgcaatctt ggctcgctgc aacctccaac    60
tcccaggttc aagtgattct cgtgcctcag cctcctgagt agctgggatt acaggcgcct   120
gccaccatgc ccggctaatt ttagtatttc tagtagagtt gggatttcac catgttggcc   180
aagctgttct cgaactcttg gcttcatggg atctgcccgc tcggcttcc  caaagtgcta   240 ggattacagg cgtgagccac tgcactcagc cagaaaagat tatttaaaat aattgaatgc   300
atgcaactgc agcatctttt gaaatcaaaa gcaaattaat atctgaggtt ttctataatt   360
aactgtcaag gccaatactt ctggttttat tattttggt  ttctacttt  ctgaggttat   420 cgataaatgg agaaacatga ttaaataaat gctttatctn cacttctcga tggcagtcag   480
ctttaatgga aaatatttc  ctataaacct aaattaattt ccggaaaccc cttttgaggt   540
taactaccat tgcactggaa taatctttgg natcccggaa ccctgttcaa ggg          593
```

<210> SEQ ID NO 13
<211> LENGTH: 373
<212> TYPE: DNA
<213> ORGANISM: Homo sapiens

<400> SEQUENCE: 13

```
ggcacttcat ggggtatgga acctaaaata gggtgaaaaa taagagttag aaaaagggag      60
gaggaagtaa gctaataaaa ccacaacaga tacattatgc aaaaatccaa caagggcttg     120
agctccaaat tcccaaaaaa gacccatgca ctaaatactt aaccaagcca ttacatttca     180
tcaagcaagc agatgggcag ttaagtgtct tttataaaac gctcaagttc tgctcctatc     240
acctggttac ccctgagcaa tcttcccaga cttttcccact ctgaacctca aatttccttg    300
tctgcagaat ggggatgata atagtacttc tccacaagac tgtggtgagg attaaatgag     360
ttagtcaagt gca                                                        373
```

<210> SEQ ID NO 14
<211> LENGTH: 1713
<212> TYPE: DNA
<213> ORGANISM: Mus musculus

<400> SEQUENCE: 14

```
gggctcccct cagcggcctc tggcgcctcc cgcccgcccg accgttcgc tcgctcgctc       60
gctcgctcgc ttgctcgtcc gggatcgccg cggtggttca agtttgcgat ggcgccgcca    120
cttcccacct gggcctcacg cgtgcacctt gcctgcctgc gcctcttcgc tcaagtcgg     180
cttttacctc aggggctctg gagagcccaa cctggccgac gccggccttc ctgaggagaa    240
ctcctccacc tgccttgccc ttgctctgtg acagctcttc ctcaggttac ccctgtggtc    300
tctcctcagg aagtttgcgc tctctcccaa tctcccttct caagtgcaat ggaatgccca    360
agccagccct cggggcctgt tgccctcctg gaaagatctg gcgattgagg acccgcccta    420
tctgctctct ggacccacca ggtcctctgt acctcgcttt agtctttggt aaaattcatc    480
tcttggggca gcaagagaga ggacagaagg gagagtggtt ggttctccac aaacttctgt    540
gttaagagtc agattgggcc tgggctcttg tgacttgggc gattgactga accttttcta    600
agcccagttt ttaatcatct ctaaaatgac agggccagga ccgaaagaga ctgtagctca    660
gttgtaaagt cacgcttgcc agacaacccc gaagccctag agagagggag gaaggagggt    720
aagttgaagg taatctccaa ctacttagga agttcaaaaa aggcctggaa tacataagac    780
ctcgtctcaa aaacgaaatt taaaacgata gaccatgaga aatcagctag tcaggtttaa    840
agtaaatgac attagtttta aaatcctagg cagttgatgg tggcacaggc ctttaatccc    900
agcaagctgg aggagacagg aggaggttca ctaggacagc caaggctaca caagaaaacc    960
ctgtctcgaa aaaataatct tacttctaga attgtagaaa tggctctgta gttaacagca   1020
cttgttgctc ctgcagaggc cctaggtttg actcccatca tccacatgac agctcatacc   1080
ttcagatctg acacctgctt ttggtaaaca cagacatgta tggagccaaa gacccaaac    1140
acataaaaat cctctttgtt gttgttttat gagttagggt ttctctgtgt agccctggct   1200
gtccaggaac tctgtagatc aggctgtcct tgaactcaga ggccacctgc ctctgcttct   1260
tgaactgctg ggattaaaga tgtacaccag caagcccagc ataaaaatac atatttaaat   1320
aatttttttaa ataatcctta gttccttcac aactctaagc cccttcactt tctagttacc   1380
atgaaattct gagcacctgt atccatttgg atcattaggg ctcaattgca catggttcaa   1440
```

```
ttacagtggg gtttccccag attttagagt tagaggcagc aggatcagaa aattaaatcc    1500
atttgcacta ggtaataaat ttgatcccac cctatctcaa aaacaaaaca ctagccacac    1560
gtggcagcac acaccttta caacaggact caggagcctg gcatgatggg acagaccttt    1620
actccctgca cttgaggcag atgcaggcaa atctaggcat cctggtgtac atatgaagtt    1680
caggcaagcc agggccacgt aggctcaaag acg                                 1713
```

<210> SEQ ID NO 15
<211> LENGTH: 660
<212> TYPE: DNA
<213> ORGANISM: Homo sapiens
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t

<400> SEQUENCE: 15

```
tttttttttt ttttttcccc acaggtagat aagagtcttg ctctgtcacc caggctggag     60
tgcagtggct caatcatagc tcactgcagc cttgaactcc tggactcaag ggatcctctt    120
gccttagtct caggagtaac tgggacaaca ggcttgcgcc accatgcccg gctaattttt    180 aaattttttgg tagagatggg ggtctcgtta tgttgcccag gctgctcttg aactcctggc   240
ctcgagcgat ccccgtctca gcctccgaaa gtgctggtat tacaagtgtg agctaccact    300
tcgagactca cttttcacca acatttcag cagttgtgtc agacagcaag tcaatgtgcc    360
attatttact taaatattca tccattatag ggcatctgat acctaacaac catggacctt    420 aagattttt cctatgtagc ctcagttctt agatgcaatt actatggaga cgggtacgat    480
cacatgccag tgggagtatt aaccgcacaa catttatgag ggatcattaa agcgttaaat    540
gcatatactt ttggacctag caatcccagt actaggaatt tatgcanaca gtgaggtgcc    600
aacaaggtta ttcaccacag catgatgnca caatactaaa ggttagaacg tatttcaatg    660
```

<210> SEQ ID NO 16
<211> LENGTH: 589
<212> TYPE: DNA
<213> ORGANISM: Homo sapiens

<400> SEQUENCE: 16

```
agtctggtgt ctcatctctc gccccggagg tcaaacctgg agccagcatt tctgtaccct     60
gcgctcacac cttttcaac ccggatggcg gtgatagtta atactttctg agcgctttta     120
ctatggtcag gcattatatt tacacctaat cctcgcaaaa cactactggg aagatcctca    180
tttgacagga gcaattccgg gtcacaaagg ctgacaccac aaagctagtc cgtagcgggt    240
tcgaccacag gcgcccacac tctttgacgc ctcaatggca cagccaagtg cgcgggaagt    300
gggctgcaaa cgccggagag ttttgtccgg agcgcagaga cgcgctgtaa ccgagcaacc    360
agcggggccc gccccggcc tgctacggcg ctcccagcct gccccgcgcc gctcggcgcc     420
ggaagtgagt gagcatttcc ggcagccatc ccgcgcgtgc tgacatcccg gttgttcttc    480
tgtgccgggg gtcttcctgc tgtcatgaag gacgtaccgg gcttcctaca gcagagccag    540
aactccgggc ccgggcagcc cgctgtgtgg caccgtctgg aggagctct                589
```

<210> SEQ ID NO 17
<211> LENGTH: 726

```
<212> TYPE: DNA
<213> ORGANISM: Homo sapiens
<220> FEATURE:
<221> NAME/KEY: misc_feature
<222> LOCATION: (630)..(630)
<223> OTHER INFORMATION: n is a, c, g, or t

<400> SEQUENCE: 17
tttttttttt ttttttttga ccatagattg agatttatac cacataccac acatagccac      60
agaaacatca tcttgaaata aagaagagtt ttggacaaaa atgtatgtgt aaattatcaa     120
ataaaggggc caggcacagt ggctcatgcc tgtaatccca gcactttggg aggccgaggt     180
gggtggatca cttgaagcca ggagttcgag accagcctgg ccaacatagc aaaaccttgt     240
ctctattaca aatatgccca tgtgctaggt gtggtgggac acacctgtaa tcccagctac     300
ccaggagaat cgcttaaacc cgggaggcgg aagttgcagt gagctgagat cgtaacaccg     360
cactccaccc tgagtgacag ggcaagactc aaaaaataaa aaaggaacat taactagggt     420
tagaaactaa cttcattctt tttagaattc aacagttttc ctaggtcacc aattccacct     480
tttgttctta ttaaggcgca aagtcacagg accccttcc tgggagtcac tgtcattaaa      540
tctattgccg tcagctcagc ccagggtagg caaggttcaa gaatgggaag tgcttttgtc     600
tggggaaaca cgcaggtaat gtgatgctan gaaggaggat gtgcaggtgg gtgagagccc     660
aggagggagc agctggtgcc tgacagggtg agccatcagg gctgggccct gggtacagcc     720
caggag                                                                726

<210> SEQ ID NO 18
<211> LENGTH: 320
<212> TYPE: DNA
<213> ORGANISM: Homo sapiens

<400> SEQUENCE: 18
tagaggatcc cagaggttgt ggcaggtggg actgtgggca ttacctgaag tctggaatgc      60
cactgggtgt gctgatgccg gccccaccat gaccaccacc ctctggcagg ctctggcccg     120
aatcagctca gctacatcct gcagggaaag cttcccttg tcactgctgc ctccacttcc      180
aacaacactt gaagcaccca cagaaaaaga tatggacctt cttccacctt taatactgac     240
agaaaaaaac acagcagcaa aggaaacaga tagcaaccaa tctcaggata gcaagaacga     300
gcatggccct gccacaacct                                                 320

<210> SEQ ID NO 19
<211> LENGTH: 616
<212> TYPE: DNA
<213> ORGANISM: Homo sapiens
<220> FEATURE:
<221> NAME/KEY: misc_feature
<222> LOCATION: (602)..(602)
<223> OTHER INFORMATION: n is a, c, g, or t

<400> SEQUENCE: 19 tttttatt aaaaaaaatg agttttaatt aagaatatcc acacattaag atacctagaa       60
ccttctatac tttgtcagtg caccctactc tgttgaatgg gaactggaat ctgtcatttg     120
agaaggcatt tacatttagc agcaagattc aagtgaaagt ccctgttcca ggttctggaa     180
tatcaggctg tggtcagcat gggtctatca aaggcagcaa ctctccacaa cgagaattca     240
gtttcagaca cgccaagtca tccgaccgtg tgggcccaat gttcagtatt gcaatcggga     300
gcttcttctc ccaggcagtg aggataaacc tgtaaccaga gtatacctgc aaggatgatc     360
```

```
ccaccaccaa gagggagtcg gcttcttta cacgcttgtg cacaaaatca accttgtcag    420
ggttcactgt gtccccgaag aaaacgacat ctggtttcag atggcctcca cattgaacac    480
aggttgggac cgaaagctcc ggacttgctc ctctgagaga aagacgtcac catcaggagc    540
caggccatgg gctcagcact ccagttgggt tcaggacttg aacgctctt gcagcacccc    600 cnggagtctg ttccca                                                    616

<210> SEQ ID NO 20
<211> LENGTH: 492
<212> TYPE: DNA
<213> ORGANISM: Homo sapiens

<400> SEQUENCE: 20
tttttttttt tgagttccaa taaaacttta tttccaaaaa caggtagcag gcccaatgtg     60
gcccaaaggc tgctgtttgc tcactcctgg gtctaaaaaa aaacatacta aactgctaac    120
ggtaactatt tctggatagc aaaactatgg gcgatttcta atttcctctt tataatgtga    180 taattttgc atgttctcaa ttaaatttaa tcataagcat gtattattta aaaaaccaat    240
agcatgttct tttctttgtt tttggtgggg ctgggggagg aggctttgaa atgcccaaaa    300
catgcatggt ttcctatttt aatacaaatt cttattcatt gtttctcagt ttttctatag    360
gataccacaa agacctctca acatacattt gaaggaaagg aagaaatgga gggaggagag    420
aaggcgggaa ggaaagaagc aagggaggga ggaaggaaaa gaggataggg ggaaggaaaa    480
aataacaaac tc                                                        492

<210> SEQ ID NO 21
<211> LENGTH: 428
<212> TYPE: DNA
<213> ORGANISM: Homo sapiens

<400> SEQUENCE: 21
agggtgagtt gcaagacagg aagagggga tagaacaaga cacagacaga gagataaaga     60
gttaaagaca aagcaagtca gagacagaat tggagagaga cagagagagg gagaggcaga    120
gagagagaga tgaattcaca cgaaggcaaa aatgacttat tctattcaac caacactgct    180
gctgcaatga gcccgacgat gctcacatgg gcccaagccc tgccctccag aagcccttga    240
tcttggggga gacaggtgga cacagatcct ctggccccaa gagtcaagcc tggatcagag    300
gaggtacctg ggcctgggga agcccgtgg aggtgggggc cctggggcac gtggaagggc    360
ttcctggagg aggctaagca gtttcttgaa gggtgagagg aagatcaga cagaagggat    420 cctctaga                                                             428

<210> SEQ ID NO 22
<211> LENGTH: 4041
<212> TYPE: DNA
<213> ORGANISM: Homo sapiens

<400> SEQUENCE: 22
gtggcctgga ggactcattt aagaatcatg tgttgagtac ctactttgta ctgggcacac     60
tggagagcaa aggtggtacc atctatgccc tggtggctgc gggtggacac aaacatgtga    120
ccaggggcca ggactggtca ggaaggagga agcggtcctt ttgaggaggg cgaggcaacg    180
gaccctgccg cccaccagga ctggtgtccc tcaccttacc cccacccttg ccctcctcag    240
gtggcctgtg gagaggagaa acacagggca ccaactatga agactctcag ggcgcgattt    300
aagaagacag agctgcggct cagccccact gaccttggct cctgcccgcc ctgcggcccc    360
```

```
tgccccatcc cgaagccggc agccagaggc aggcgccaga gtcaagactg gggcaagagt    420
gacgagaggc tgctacaagc cgtggaaaac aacgatgcac ctcgggtggc cgccctcatc    480
gcccgcaagg ggctggtgcc cacgaagcta gaccccgagg gcaagtccgc gttccacctg    540
gcggccatgc ggggtgcggc cagctgtctg gaggtgatga tagctcatgg cagcaatgtc    600
atgagcgcgg acgggcagg ttacaatgcc ctccacctgg ccgccaaata cgggcaccca    660
cagtgcttga agcaactact gcaggcttcc tgcgtggtgg acgtcgtgga cagcagcggg    720
tggactgccc tacaccatgc agcggctggt ggctgtctct cctgctcaga ggtgctctgc    780
tcctttaagg cacatctaaa ccccaagat cggtcaggcg caacacccct cattatagca     840
gctcagatgt gtcacacaga cctgtgccgt ctcctactgc agcaaggggc tgccgcgaac    900
gatcaggacc tgcaaggcag gacggccctg atgctggcct gtgaggggc cagccccgaa     960
acagtggagg tcctgctgca gggcggagcc cagccgggca tcaccgatgc gctggggcag   1020
gacgcggctc actatggcgc cctggcgggg gacaaactca tcctgcacct tctgcaagag   1080
gcggcccagc gcccctcccc acccagcgcc ctcacagagg atgattcagg cgaggcgtca   1140
tctcagaact ctatgtccag ccatggaaag caggggccc caagaagcg gaaggcgcct    1200
ccacctcccg ccagcattcc catgccggat gatcgagatg cctatgagga gatcgtgagg   1260
ctgcggcagg agaggggccg cctcctgcag aagatccggg gcctggaaca gcacaaggaa   1320
cggaggcagc aggagtcccc ggaggccagc tccctgcaca tcctggagag acaggtgcaa   1380
gagctacagc agttgctggt ggagagacaa gaggagaagg agagcctggg acggaggtg    1440
gagagtttgc agagccggct gtccctgctg agaacgagc gggagaatac tagctatgac    1500
gtaaccaccc tgcaggatga ggaggtgag ctgcctgacc ttccaggggc cgaggtgctg     1560
ctgtccagac aactcagtcc gtcggcccag gaacacctgg cctcgctgca ggaacaggtg   1620
gctgtgctca ccagacagaa ccaggaactg atggagaagg tccagatcct ggagaacttt   1680
gagaaggacg agacacagat ggaagtggaa gctttggcag aggtcatccc tcttgccctc   1740
tatgactctc tccgggccga gtttgaccag ctacgcaggc agcacgctga ggccctgcag   1800
gccctgaggc agcaggagac acgagaggtc cccagagaag aggggcagc ctgtggggag    1860
agtgaggttg ctggagccac ggccaccaaa acgggccaa cccacatgga gctaaatggc    1920
tcagtggctc cagaaaccaa agttaacgga gccgagacca tagatgagga ggctgcagga   1980
gatgaaacca tggaagccag gactatggaa gctgaggcca cgggagccga ggccacggga   2040
gctgaggcca caggagccaa ggtcacagaa acaaaaccca cagggctga ggtcagagaa    2100
atggagacca cagaagaaga agcaaacatg gaactaagc ccacaggagc tcaggccaca    2160
gacacagaga ccacgggagt ggaggccatg ggggtgagg ccacaaaaac aaaagcagag    2220
gaagcagaaa tgcaggccta cggagtgggt gctgggcaag cagagccccc agtcacaggg   2280
accacaaaca tggaggccac gggctctagg ccacagggga tggaatccac aggagtcagt   2340
gccacaggtg tggagaaccc aggggtagag gccacggtcc cggggatctc tgctggcccc   2400
atcctacatc ctggtgccgc agaggcctcg gaaaagcttc aagtagagct ggagaccagg   2460
atccgtggct tggaggaggc tctccggcag cgggagcggg aggcagctgc ggagctggag   2520
gcggccctgg ggaagtgcga ggccgcggag gccgaggcag gccggctgcg agagcgtgtc   2580
cgcgaggccg agggcagcgg ggccagcggg gcggtggcg gtgacaccac acagctgcgg   2640
gcggcccgg agcaggcccg ggaggacctc cgagaccggg actccgcct gcgggagctg   2700
```

| | |
|---|---|
| gaggcggcct cggcctgcct ggatgaggct cgggccagcc ggctgctggc ggaggaggag | 2760 |
| gcgcggggcc tgcgggccga gctggcccag cgggaggagg cgcggctgga gcagagccgg | 2820 |
| gagctggagg ttctgcggga gcagctggcc acggccaggg ccacggggga gcagcagcgc | 2880 |
| acggcggccg cggaactggg ccgggcacgg gacgccgctg aggcccgagt ggctgagctg | 2940 |
| cctgcggcct gcgaggaggc gcggcagggc ctggccgagc tgcgggaggc ctccgaggcc | 3000 |
| ctccgccagt ccgtggtgcc ggcctctgag caccgccggc tgcaggagga ggccctggag | 3060 |
| ctgcggggcc gggcagccag tctggagcag gaggtggtgg ccacgggcaa ggaggccgcc | 3120 |
| cggctgcgcg cggagctgga gcgggagcgt gtgtgcagcg tggcgctctc ggagcacgaa | 3180 |
| cgcatcgtgg gcaccctgca ggccaacgtg gcccagctgg aggggcagct ggaggagctg | 3240 |
| ggacggcggc atgagaagac cagcgcagag gtcttccagg tgcagcgtga ggccctgttc | 3300 |
| atgaagagtg agcgacacgc agccgaggca cagctggcca cagcagagca gcagctacgg | 3360 |
| gggctacgga ccgaggcgga aagggctcgc caggcccaga gccgggccca ggaggctctg | 3420 |
| gacaaggcca aggagaagga caagaagatc acagaactct ccaaagaagt cttcaatctt | 3480 |
| aaggaagcct tgaaggagca gccggccgcc ctcgccaccc ctgaggtgga ggctctccgt | 3540 |
| gaccaggtga aggatttaca gcagcagctg caggaagctg ccaggaccca ctccagcgtg | 3600 |
| gtggctttgt acagaagcca cctcctatat gccattcagg gccagatgga tgaagatgtg | 3660 |
| cagcggattc tcagccagat tctgcagatg cagagactcc aggctcaggg ccgctgagaa | 3720 |
| aggccaggcc cagtggctac actgaccaca cccacgcagg gacctcaccc ccctgcaggc | 3780 |
| cccttgcaga ccggcttcac ttggcttcac ttggccctat ccaggcccat gcacttggag | 3840 |
| accagcctgg ttccctgccc gaccacccc agctggctcc atcaccccac ctggtctctg | 3900 |
| cacgcacaca ctggtcagtc tggacccggg ccgtgactgc ccctccccca ccaccggaga | 3960 |
| ctgtgattcc ctgtgtcctc cacatccaga cgccagccca ggaataaagg cattctgtgc | 4020 |
| acagggaaaa aaaaaaaaa a | 4041 |

<210> SEQ ID NO 23
<211> LENGTH: 705
<212> TYPE: DNA
<213> ORGANISM: Homo sapiens
<220> FEATURE:
<221> NAME/KEY: misc_feature
<222> LOCATION: (648)..(648)
<223> OTHER INFORMATION: n is a, c, g, or t

<400> SEQUENCE: 23

| | |
|---|---|
| tttttttttt tttttctct ttaaaaggtt tattgatcat atacaaaata agaaaacct | 60 |
| tatatatcac aaacatacac tatgtacagc aataaatacc cgggggggcca ggcccagtgc | 120 |
| tgcccctcct ggacaataat ttagcaataa atactgcgca gggcaggggt agggcaccaa | 180 |
| ggccactgcc ctgcaagagg tcaggcccct gccgcccta cacgaagtgt gagcgctcgg | 240 |
| gcctcacccc gcatccaaac cccagcccct cctcacttag atctttaata acctccatcc | 300 |
| caccccagca gatcccgggg tcttctccca cacacacaac ctcccctggc tagacctagg | 360 |
| cagggcagga agggactgat caactctgct tggacccacc tctcagcgcc aggagagcaa | 420 |
| cagggctgga cacgcgggca gcccttgtcc tgttgccagg agaaggcttt ctgtgcccac | 480 |
| tcccgtttgg ttaaaggctt cagggactag cagattgagg gggtgggaag aagggcaggg | 540 |
| ctgggacaca aggttgctgg aggggccaaa gcccaactgg ggtcaccaag aacagggagg | 600 |
| tctcacagtt tatcggggac acactctagc tcagactcaa gggacacnca tggtatcaaa | 660 | gctgctgctc caggggcagg gtggaaatgt gtgggactgg ccagc          705

<210> SEQ ID NO 24
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 24
ttggtattca caag          14

<210> SEQ ID NO 25
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 25
aaactggaaa ccta          14

<210> SEQ ID NO 26
<211> LENGTH: 14
<212> TYPE: DNA
<213> ORGANISM: Artificial Sequence
<220> FEATURE:
<223> OTHER INFORMATION: Antisense Oligonucleotide

<400> SEQUENCE: 26
gatctttatg agaa          14

<210> SEQ ID NO 27
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 27
gatggagaaa ttgg          14

<210> SEQ ID NO 28
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 28
agtctgatgg agaa          14

<210> SEQ ID NO 29
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 29
tgttaaggga tgtc          14

<210> SEQ ID NO 30
<211> LENGTH: 14
<212> TYPE: DNA

```
<213> ORGANISM: Artificial Sequence
<220> FEATURE:
<223> OTHER INFORMATION: Antisense oligonucleotide

<400> SEQUENCE: 30
aatctgcttt tgtt                                                    14

<210> SEQ ID NO 31
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 31
agggaattga aatc                                                    14

<210> SEQ ID NO 32
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 32
taaggcaaga tttc                                                    14

<210> SEQ ID NO 33
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 33
taaatggagt taag                                                    14

<210> SEQ ID NO 34
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 34
ttatttatag caca                                                    14

<210> SEQ ID NO 35
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 35
ttgcttctgc ttat                                                    14

<210> SEQ ID NO 36
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 36
aaaaaaatat ttgc                                                    14
```

```
<210> SEQ ID NO 37
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 37
cagccttaaa aaaa                                                          14

<210> SEQ ID NO 38
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 38
ttttaaaacc tctc                                                          14

<210> SEQ ID NO 39
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 39
tagttcagat tttt                                                          14

<210> SEQ ID NO 40
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 40
agcagttgct aaat                                                          14

<210> SEQ ID NO 41
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 41
ctgagtgcag cagc                                                          14

<210> SEQ ID NO 42
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 42
gtctgatgga ga                                                            12

<210> SEQ ID NO 43
<211> LENGTH: 12
<212> TYPE: DNA
<213> ORGANISM: Artificial Sequence
<220> FEATURE:
```

<223> OTHER INFORMATION: Antisense oligonucleotide

<400> SEQUENCE: 43
gtctgatgga ga                                                    12

<210> SEQ ID NO 44
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 44
gtctgatgga ga                                                    12

<210> SEQ ID NO 45
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 45
guctgatgga ga                                                    12

<210> SEQ ID NO 46
<211> LENGTH: 12
<212> TYPE: DNA
<213> ORGANISM: Artificial Sequence
<220> FEATURE:
<223> OTHER INFORMATION: Antisense oligonucleotide

<400> SEQUENCE: 46
gucugaugga ga                                                    12

<210> SEQ ID NO 47
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 47
actgacacct aattgtattc acatgaa                                    27

<210> SEQ ID NO 48
<211> LENGTH: 26
<212> TYPE: DNA
<213> ORGANISM: Artificial Sequence
<220> FEATURE:
<223> OTHER INFORMATION: Antisense oligonucleotide

<400> SEQUENCE: 48
tgagcagcag ttgctaaatt agttca                                     26

<210> SEQ ID NO 49
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 49
tctacctaca ttatatcata gctccta                                    27

```
<210> SEQ ID NO 50
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 50
ttggtattca caagtgaaa                                                    19

<210> SEQ ID NO 51
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 51
ttgctaaatt agttcagat                                                    19

<210> SEQ ID NO 52
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 52
gcagcagcag ttgctaaat                                                    19

<210> SEQ ID NO 53
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 53
gcagttgcta aattagttc                                                    19

<210> SEQ ID NO 54
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 54
gccatgttgc ccagtccagt                                                   20

<210> SEQ ID NO 55
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 55
gggctctgct acttacttgc                                                   20

<210> SEQ ID NO 56
<211> LENGTH: 20
<212> TYPE: DNA
<213> ORGANISM: Artificial Sequence
<220> FEATURE:
<223> OTHER INFORMATION: Antisense oligonucleotide
```

```
<400> SEQUENCE: 56
cccagtcttc agccttgtct                                               20

<210> SEQ ID NO 57
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 57
gggtctctgt catatgttct t                                             21

<210> SEQ ID NO 58
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 58
ttcctacctt ccctccata                                                19

<210> SEQ ID NO 59
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 59
attcctacct tccctccat                                                19

<210> SEQ ID NO 60
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 60
ccttagggtt gcagctaatt                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 61
atcccagcta ctcaggaggc                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 62
tctggctgag tgcagtggct                                               20

<210> SEQ ID NO 63
<211> LENGTH: 20
```

```
<212> TYPE: DNA
<213> ORGANISM: Artificial Sequence
<220> FEATURE:
<223> OTHER INFORMATION: Antisense oligonucleotide

<400> SEQUENCE: 63
cctgggagtt ggaggttgca                                           20

<210> SEQ ID NO 64
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 64
cagatcccat gaagccaaga g                                         21

<210> SEQ ID NO 65
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 65
ctgactgcca tcgagaagtg g                                         21

<210> SEQ ID NO 66
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 66
gcccatctgc ttgcttgat                                            19

<210> SEQ ID NO 67
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 67
atcctcacca cagtcttgt                                            19

<210> SEQ ID NO 68
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 68
gcttacttcc tcctcccttt                                           20

<210> SEQ ID NO 69
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 69
```
ccaggtgata ggagcagaac t                                      21

<210> SEQ ID NO 70
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 70
accctccttc ctccctctct                                        20

<210> SEQ ID NO 71
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 71
ccactctccc ttctgtcctc t                                      21

<210> SEQ ID NO 72
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 72
cctccttcct ccctctctct                                        20

<210> SEQ ID NO 73
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 73
gtctgtccca tcatgccagg                                        20

<210> SEQ ID NO 74
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 74
tttctgatcc tgctgcctct                                        20

<210> SEQ ID NO 75
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 75
accctccttc ctccc                                             15

<210> SEQ ID NO 76
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 76
ctccttcctc cctc                                                   14

<210> SEQ ID NO 77
<211> LENGTH: 11
<212> TYPE: DNA
<213> ORGANISM: Artificial Sequence
<220> FEATURE:
<223> OTHER INFORMATION: Antisense oligonucleotide

<400> SEQUENCE: 77
ctccttcctc c                                                      11

<210> SEQ ID NO 78
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 78
cttcctccct ctctc                                                  15

<210> SEQ ID NO 79
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 79
atcctgctgc ctct                                                   14

<210> SEQ ID NO 80
<211> LENGTH: 14
<212> TYPE: DNA
<213> ORGANISM: Artificial Sequence
<220> FEATURE:
<223> OTHER INFORMATION: Antisense oligonucleotide

<400> SEQUENCE: 80
ctccttcctc cctc                                                   14

<210> SEQ ID NO 81
<211> LENGTH: 15
<212> TYPE: DNA
<213> ORGANISM: Artificial Sequence
<220> FEATURE:
<223> OTHER INFORMATION: Antisense oligonucleotide

<400> SEQUENCE: 81
accctccttc ctccc                                                  15

<210> SEQ ID NO 82
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 82
gttctggctc tgctgtagga                                             20

<210> SEQ ID NO 83
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 83
atgctcactc acttccggcg                                              20

<210> SEQ ID NO 84
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 84
ctttgtggtg tcagcctttg t                                            21

<210> SEQ ID NO 85
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 85
aggtgtgagc gcagggtaca                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 86
ctcggttaca gcgcgtctct                                              20

<210> SEQ ID NO 87
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 87
aactctccgg cgtttgcag                                               19

<210> SEQ ID NO 88
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 88
tgttgtccca gttactcct                                               19

<210> SEQ ID NO 89
<211> LENGTH: 20
<212> TYPE: DNA
<213> ORGANISM: Artificial Sequence
<220> FEATURE:
<223> OTHER INFORMATION: Antisense oligonucleotide

```
<400> SEQUENCE: 89
gccaggagtt caagagcagc                                        20

<210> SEQ ID NO 90
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 90
ccttgttggc acctcactgt                                        20

<210> SEQ ID NO 91
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 91
gttgtgcggt taatactccc                                        20

<210> SEQ ID NO 92
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 92
gtgagtctcg aagtggtagc t                                      21

<210> SEQ ID NO 93
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 93
gactcttatc tacctgtggg a                                      21

<210> SEQ ID NO 94
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 94
gtcccaccac acctagcaca                                        20

<210> SEQ ID NO 95
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 95
ggctatgtgt ggtatgtggt                                        20

<210> SEQ ID NO 96
```

```
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 96
tcagggtgga gtgcggtgtt                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 97
acccacctgc acatcctcct                                              20

<210> SEQ ID NO 98
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 98
gtaatgccca cagtcccacc t                                            21

<210> SEQ ID NO 99
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 99
cagagggtgg tggtcatggt                                              20

<210> SEQ ID NO 100
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 100
tctgtgggtg cttcaagtgt                                              20

<210> SEQ ID NO 101
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 101
agggccatgc tcgttcttgc                                              20

<210> SEQ ID NO 102
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 102
```
gtgttgttgg aagtggaggc        20

<210> SEQ ID NO 103
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 103
tcccattctt gaaccttgcc t        21

<210> SEQ ID NO 104
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 104
cagattccag ttcccattca        20

<210> SEQ ID NO 105
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 105
gttgtggaga gttgctgcct        20

<210> SEQ ID NO 106
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 106
gatagaccca tgctgaccac a        21

<210> SEQ ID NO 107
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 107
gcgtttccaa gtcctgaacc c        21

<210> SEQ ID NO 108
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 108
gccttctctc ctccctccat        20

<210> SEQ ID NO 109
<211> LENGTH: 20
<212> TYPE: DNA

```
<213> ORGANISM: Artificial Sequence
<220> FEATURE:
<223> OTHER INFORMATION: Antisense oligonucleotide

<400> SEQUENCE: 109
tccttcctcc ctcccttgct                                                 20

<210> SEQ ID NO 110
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 110
gcatctcaaa gcctcctccc                                                 20

<210> SEQ ID NO 111
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 111
cttctagacc caggagtgag c                                               21

<210> SEQ ID NO 112
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 112
tccttctcct cttgtctctc c                                               21

<210> SEQ ID NO 113
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 113
gccctgtgtt tctcctctcc                                                 20

<210> SEQ ID NO 114
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 114
actcccgtgg tctctgtgtc t                                               21

<210> SEQ ID NO 115
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 115
tccagcaacc tcactctccc                                                 20
```

<210> SEQ ID NO 116
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 116
gcgtgggtgt ggtcagtgta                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 117
accacctcct gctccagact                                               20

<210> SEQ ID NO 118
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 118
cctctccctc tctctgtctc t                                             21

<210> SEQ ID NO 119
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 119
atcttccctc tcacccttc                                                19

<210> SEQ ID NO 120
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 120
cccttctgtc tgatcttccc t                                             21

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
tctgtgtcca cctgtctccc                                               20

<210> SEQ ID NO 122
<211> LENGTH: 19
<212> TYPE: DNA
<213> ORGANISM: Artificial Sequence
<220> FEATURE:

```
<223> OTHER INFORMATION: Antisense oligonucleotide

<400> SEQUENCE: 122 cgggtatttta ttgctgtac                                                    19

<210> SEQ ID NO 123
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 123
gccagtccca cacatttcca c                                                  21

<210> SEQ ID NO 124
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 124
gggaggttgt gtgtgtggga                                                    20

<210> SEQ ID NO 125
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 125
caaccttgtg tcccagccct                                                    20

<210> SEQ ID NO 126
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 126
ccagugugcc aaucccagau ggugcuu                                            27

<210> SEQ ID NO 127
<211> LENGTH: 27
<212> TYPE: DNA
<213> ORGANISM: Artificial Sequence
<220> FEATURE:
<223> OTHER INFORMATION: Antisense oligonucleotide

<400> SEQUENCE: 127
cugcucagac acugguagau ccuugau                                            27

<210> SEQ ID NO 128
<211> LENGTH: 25
<212> TYPE: DNA
<213> ORGANISM: Homo sapiens

<400> SEQUENCE: 128
aactggagct ggggtgtctg tttca                                              25

<210> SEQ ID NO 129
<211> LENGTH: 25
```

```
<212> TYPE: DNA
<213> ORGANISM: Artificial Sequence
<220> FEATURE:
<223> OTHER INFORMATION: Forward Primer Sequence

<400> SEQUENCE: 129
ccatcagacg acatccctta acaaa                                        25

<210> SEQ ID NO 130
<211> LENGTH: 31
<212> TYPE: DNA
<213> ORGANISM: Artificial Sequence
<220> FEATURE:
<223> OTHER INFORMATION: Reverse Primer Sequence

<400> SEQUENCE: 130
acattatatc atagctccta aaggagatgc a                                 31

<210> SEQ ID NO 131
<211> LENGTH: 16
<212> TYPE: DNA
<213> ORGANISM: Artificial Sequence
<220> FEATURE:
<223> OTHER INFORMATION: Reporter Sequence

<400> SEQUENCE: 131
cagagtttca attccc                                                  16

<210> SEQ ID NO 132
<211> LENGTH: 12
<212> TYPE: DNA
<213> ORGANISM: Artificial Sequence
<220> FEATURE:
<223> OTHER INFORMATION: Antisense Oligonucleotide

<400> SEQUENCE: 132
gctagtctgt tg                                                      12

<210> SEQ ID NO 133
<211> LENGTH: 3604
<212> TYPE: DNA
<213> ORGANISM: Homo sapiens
<300> PUBLICATION INFORMATION:
<308> DATABASE ACCESSION NUMBER: NM_001142498.1
<309> DATABASE ENTRY DATE: 2011-01-03
<313> RELEVANT RESIDUES IN SEQ ID NO: (1)..(3604)

<400> SEQUENCE: 133
gcatctcctc ctccctctcc ccgggctcct actggcctga ggttgagggc ggctgggggc      60
tcggggcagg ctccgcggcg ttcccctccc caccccggcc ctccgttcag ccgcgctcct     120
ccggggctgc ggttcctact gcgcgagctg ccagtggatt cgctcttttc ctccgtccgt     180
ggcccgcctg gcggccttg ttctttccgc agcagccaga taaccttctg ttcggtgatg      240
aaattatcac taatggtttt cattcctgtg aaagtgatga ggaggataga gcctcacatg     300
caagctctag tgactggact ccaaggccac ggataggtgt ctgtttcatg tggaatacct     360
gacttcaggt caagggatgg tatttatgct cgccttgctg tagacttccc agatcttcca     420
gatcctcaag cgatgtttga tattgaatat ttcagaaaag atccaagacc attcttcaag     480
tttgcaaagg aaatatatcc tggacaattc cagccatctc tctgtcacaa attcatagcc     540
ttgtcagata aggaaggaaa actacttcgc aactataccc agaacataga cacgctggaa     600
caggttgcgg gaatccaaag gataattcag tgtcatggtt cctttgcaac agcatcttgc     660
```

```
ctgatttgta aatacaaagt tgactgtgaa gctgtacgag gagatatttt taatcaggta    720
gttcctcgat gtcctaggtg cccagctgat gaaccgcttg ctatcatgaa accagagatt    780 gtgtttttg  gtgaaaattt accagaacag tttcatagag ccatgaagta tgacaaagat    840
gaagttgacc tcctcattgt tattgggtct tccctcaaag taagaccagt agcactaatt    900
ccaagttcca tacccatga agtgcctcag atattaatta atagagaacc tttgcctcat    960
ctgcattttg atgtagagct tcttggagac tgtgatgtca taattaatga attgtgtcat   1020
aggttaggtg gtgaatatgc caaactttgc tgtaaccctg taaagctttc agaaattact   1080
gaaaaacctc cacgaacaca aaaagaattg gcttatttgt cagagttgcc acccacacct   1140
cttcatgttt cagaagactc aagttcacca gaaagaactt caccaccaga ttcttcagtg   1200
attgtcacac ttttagacca agcagctaag agtaatgatg atttagatgt gtctgaatca   1260
aaaggttgta tggaagaaaa accacaggaa gtacaaactt ctaggaatgt tgaaagtatt   1320
gctgaacaga tggaaaatcc ggatttgaag aatgttggtt ctagtactgg ggagaaaaat   1380
gaaagaactt cagtggctgg aacagtgaga aaatgctggc ctaatagagt ggcaaaggag   1440
cagattagta ggcggcttga tggtaatcag tatctgtttt tgccaccaaa tcgttacatt   1500
ttccatggcg ctgaggtata ttcagactct gaagatgacg tcttatcctc tagttcttgt   1560
ggcagtaaca gtgatagtgg gacatgccag agtccaagtt tagaagaacc catggaggat   1620
gaaagtgaaa ttgaagaatt ctacaatggc ttagaagatg agcctgatgt tccagagaga   1680
gctggaggag ctggatttgg gactgatgga gatgatcaag aggcaattaa tgaagctata   1740
tctgtgaaac aggaagtaac agacatgaac tatccatcaa acaaatcata gtgtaataat   1800
tgtgcaggta caggaattgt tccaccagca ttaggaactt tagcatgtca aaatgaatgt   1860
ttacttgtga actcgataga gcaaggaaac cagaaaggtg taatatttat aggttggtaa   1920
aatagattgt ttttcatgga taatttttaa cttcattatt tctgtacttg tacaaactca   1980
acactaactt tttttttttt aaaaaaaaaa aggtactaag tatcttcaat cagctgttgg   2040
tcaagactaa ctttctttta aaggttcatt tgtatgataa attcatatgt gtatatataa   2100 tttttttgt  tttgtctagt gagtttcaac atttttaaag ttttcaaaaa gccatcggaa   2160
tgttaaatta atgtaaaggg aacagctaat ctagaccaaa gaatggtatt ttcacttttc   2220
tttgtaacat tgaatggttt gaagtactca aaatctgtta cgctaaactt ttgattcttt   2280
aacacaatta ttttaaaca  ctggcatttt ccaaaactgt ggcagctaac ttttaaaat    2340 ctcaaatgac atgcagtgtg agtagaagga agtcaacaat atgtggggag agcactcggt   2400
tgtctttact tttaaaagta atacttggtg ctaagaattt caggattatt gtatttacgt   2460
tcaaatgaag atggctttg  tacttcctgt ggacatgtag taatgtctat attggctcat   2520
aaaactaacc tgaaaacaa  ataaatgctt tggaaatgtt tcagttgctt tagaaacatt   2580
agtgcctgcc tggatcccct tagttttgaa atatttgcca ttgttgttta aatacctatc   2640
actgtggtag agcttgcatt gatcttttcc acaagtatta aactgccaaa atgtgaatat   2700
gcaaagcctt tctgaatcta taataatggt acttctactg gggagagtgt aatattttgg   2760
actgctgttt tccattaatg aggagagcaa caggccoctg attatacagt tccaaagtaa   2820
taagatgtta attgtaattc agccagaaag tacatgtctc ccattgggag gatttggtgt   2880
taaataccaa actgctagcc ctagtattat ggagatgaac atgatgatgt aacttgtaat   2940
agcagaatag ttaatgaatg aaactagttc ttataattta tctttattta aaagcttagc   3000
ctgccttaaa actagagatc aactttctca gctgcaaaag cttctagtct ttcaagaagt   3060
```

```
tcatacttta tgaaattgca cagtaagcat ttattttttca gaccattttt gaacatcact    3120
cctaaattaa taaagtattc ctctgttgct ttagtattta ttacaataaa aagggtttga    3180
aatatagctg ttctttatgc ataaaacacc cagctaggac cattactgcc agagaaaaaa    3240
atcgtattga atggccattt ccctactat aagatgctc aatctgaatt tatttggcta     3300
cactaaagaa tgcagtatat ttagttttcc atttgcatga tgtttgtgtg ctatagatga    3360 tatttaaat tgaaaagttt gttttaaatt attttacag tgaagactgt tttcagctct      3420
ttttatattg tacatagtct tttatgtaat ttactggcat atgttttgta gactgtttaa    3480
tgactggata tcttccttca acttttgaaa tacaaaacca gtgtttttta cttgtacact    3540
gttttaaagt ctattaaaat tgtcatttga cttttttctg ttaacttaaa aaaaaaaaa    3600 aaaa                                                                3604
```

<210> SEQ ID NO 134
<211> LENGTH: 2078
<212> TYPE: DNA
<213> ORGANISM: Homo sapiens
<300> PUBLICATION INFORMATION:
<308> DATABASE ACCESSION NUMBER: NM_030593.2
<309> DATABASE ENTRY DATE: 2010-08-15
<313> RELEVANT RESIDUES IN SEQ ID NO: (1)..(2078)

<400> SEQUENCE: 134

```
agagtattcg ggaggactac aactctctag ccgttcccac attttccggg cgcccttttac     60 caacatggct gctgacgcca cgccttctgg gactcgtagt ccggtcctcg cgcgcttttct   120 tacctaactg gggcgctctg ggtgttgtac gaaagcgcgt ctgcggccgc aatgtctgct   180
gagagttgta gttctgtgcc ctatcacggc cactcccatt tctggtgccg tcacgggaca   240
gagcagtcgg tgacaggaca gagcagtcgg tgacgggaca cagtggttgg tgacgggaca   300
gagcggtcgg tgacagcctc aagggcttca gcaccgcgcc catggcagag ccagaccgac   360
tcagattcag actctgaggg aggagccgct ggtggagaag cagacatgga cttcctgcgg   420
aacttattct cccagacgct cagcctgggc agccagaagg agcgtctgct ggacgagctg   480
accttggaag gggtggcccg gtacatgcag agcgaacgct gtcgcagagt catctgtttg   540
gtgggagctg gaatctccac atccgcaggc atccccgact ttcgctctcc atccaccggc   600
ctctatgaca acctagagaa gtaccatctt ccctacccag aggccatctt tgagatcagc   660
tatttcaaga acatccggga acccttcttc gccctcgcca aggaactcta tcctgggcag   720
ttcaagccaa ccatctgtca ctacttcatg cgcctgctga aggacaaggg gctactcctg   780
cgctgctaca cgcagaacat agataccctg gagcgaatag ccgggctgga acaggaggac   840
ttggtggagg cgcacggcac cttctacaca tcacactgcg tcagcgccag ctgccggcac   900
gaatacccgc taagctggat gaaagagaag atcttctctg aggtgacgcc caagtgtgaa   960
gactgtcaga gcctggtgaa gcctgatatc gtcttttttg gtgagagcct cccagcgcgt  1020
ttcttctcct gtatgcagtc agacttcctg aaggtggacc tcctcctggt catgggtacc  1080
tccttgcagg tgcagcccct tgcctccctc atcagcaagg cacccctctc cacccctcgc  1140
ctgctcatca acaaggagaa agctggccag tcggaccctt tcctggggat gattatgggc  1200
ctcggaggag gcatggactt tgactccaag aaggcctaca gggacgtggc ctggctgggt  1260
gaatgcgacc agggctgcct ggcccttgct gagctccttg atggaagaa ggagctggag  1320 gaccttgtcc ggagggagca cgccagcata gatgcccagt cggggcggg ggtccccaac  1380
```

| | |
|---|---|
| cccagcactt cagcttcccc caagaagtcc ccgccacctg ccaaggacga ggccaggaca | 1440 |
| acagagaggg agaaacccca gtgacagctg catctcccag gcgggatgcc gagctcctca | 1500 |
| gggacagctg agccccaacc gggcctggcc ccctcttaac cagcagttct tgtctgggga | 1560 |
| gctcagaaca tcccccaatc tcttacagct ccctccccaa aactgggtc ccagcaaccc | 1620 |
| tggcccccaa ccccagcaaa tctctaacac ctcctagagg ccaaggctta aacaggcatc | 1680 |
| tctaccagcc ccactgtctc taaccactcc tgggctaagg agtaacctcc ctcatctcta | 1740 |
| actgccccca cggggccagg gctaccccag aacttttaac tcttccagga cagggagctt | 1800 |
| cgggccccca ctctgtctcc tgccccgggg ggcctgtggc taagtaaacc atacctaacc | 1860 |
| taccccagtg tgggtgtggg cctctgaata taacccacac ccagcgtagg gggagtctga | 1920 |
| gccgggaggg ctcccgagtc tctgccttca gctcccaaag tgggtggtgg gccccctcca | 1980 |
| cgtgggaccc acttcccatg ctggatgggc agaagacatt gcttattgga gacaaattaa | 2040 |
| aaacaaaaac aactaacaat ccggaaaaaa aaaaaaa | 2078 |

<210> SEQ ID NO 135
<211> LENGTH: 1926
<212> TYPE: DNA
<213> ORGANISM: Homo sapiens
<300> PUBLICATION INFORMATION:
<308> DATABASE ACCESSION NUMBER: NM_001193286
<309> DATABASE ENTRY DATE: 2010-08-15
<313> RELEVANT RESIDUES IN SEQ ID NO: (1)..(1926)

<400> SEQUENCE: 135

| | |
|---|---|
| agagtattcg ggaggactac aactctctag ccgttcccac attttccggg cgcccttttac | 60 |
| caacatggct gctgacgcca cgccttctgg gactcgtagt ccggtcctcg cgcgctttct | 120 |
| tacctaactg gggcgctctg ggtgttgtac gaaagcgcgt ctgcggccgc aatgtctgct | 180 |
| gagagttgta gttctgtgcc ctatcacggc cactcccatt tctggtgccg tcacgggaca | 240 |
| gagcagtcgg tgacaggaca gagcagtcgg tgacgggaca cagtggttgg tgacgggaca | 300 |
| gagcggtcgg tgacagcctc aagggcttca gcaccgcgcc catggcagag ccagaccgac | 360 |
| tcagattcag actctgaggg aggagccgct ggtggagaag cagacatgga cttcctgcgg | 420 |
| aacttattct cccagacgct cagcctgggc agccagaagg agcgtctgct ggacgagctg | 480 |
| accttggaag gggtggcccg gtacatgcag agcgaacgct gtcgcagagt catctgtttg | 540 |
| gtgggagctg gaatctccac atccgcaggc atccccgact ttcgctctcc atccaccggc | 600 |
| ctctatgaca acctagagaa gtaccatctt ccctacccag aggccatctt tgagatcagc | 660 |
| tatttcaaga acatccgga acccttcttc gccctcgcca aggaactcta tcctgggcag | 720 |
| ttcaagccaa ccatctgtca ctacttcatg cgcctgctga aggacaaggg gctactcctg | 780 |
| cgctgctaca cgcagaacat agatacctg gagcgaatag ccgggctgga acaggaggac | 840 |
| ttggtggagg cgcacggcac cttctacaca tcacactgcg tcagcgccag ctgccggcac | 900 |
| gaatacccgc taagctggat gaaagagaag atcttctctg aggtgacgcc caagtgtgaa | 960 |
| gactgtcaga gcctggtgaa gcctgatatc gtctttttg gtgagagcct cccagcgcgt | 1020 |
| ttcttctcct gtatgcagtc agacttcctg aaggtggacc tcctcctggt catgggtacc | 1080 |
| tccttgcagg gacgtggcct ggctgggtga atgcgaccag ggctgcctgg cccttgctga | 1140 |
| gctccttgga tggaagaagg agctggagga ccttgtccgg agggagcacg ccagcataga | 1200 |
| tgcccagtcg ggggcggggg tccccaaccc cagcacttca gcttccccca agaagtcccc | 1260 |
| gccacctgcc aaggacgagg ccaggacaac agagagggag aaacccagt gacagctgca | 1320 |

```
tctcccaggc gggatgccga gctcctcagg gacagctgag ccccaaccgg gcctggcccc    1380
ctcttaacca gcagttcttg tctggggagc tcagaacatc ccccaatctc ttacagctcc    1440
ctccccaaaa ctggggtccc agcaaccctg gcccccaacc ccagcaaatc tctaacacct    1500
cctagaggcc aaggcttaaa caggcatctc taccagcccc actgtctcta accactcctg    1560
ggctaaggag taacctccct catctctaac tgccccacg gggccagggc taccccagaa     1620
cttttaactc ttccaggaca gggagcttcg ggccccact ctgtctcctg ccccggggg      1680 cctgtggcta agtaaaccat acctaaccta ccccagtgtg ggtgtgggcc tctgaatata    1740
acccacaccc agcgtagggg gagtctgagc cgggagggct cccgagtctc tgccttcagc    1800
tcccaaagtg ggtggtgggc cccttcacg tgggacccac ttcccatgct ggatgggcag     1860
aagacattgc ttattggaga caaattaaaa acaaaaacaa ctaacaatcc ggaaaaaaaa    1920
aaaaaa                                                               1926
```

<210> SEQ ID NO 136
<211> LENGTH: 2009
<212> TYPE: DNA
<213> ORGANISM: Homo sapiens
<300> PUBLICATION INFORMATION:
<308> DATABASE ACCESSION NUMBER: NR_034146.1
<309> DATABASE ENTRY DATE: 2010-08-15
<313> RELEVANT RESIDUES IN SEQ ID NO: (1)..(2009)

<400> SEQUENCE: 136

```
cagtgcactc cagcctgggc aacagagcga gacactgtct caaaaaagaa aagcaaagca      60
aagccactca catgaggtct tgctcctggg gacgggcatg gccaggactc caaccccggc     120
agcctgtccc agagccctgg agctagcccc agtgcagtct ctccaccacc ccgcacttcc     180
tcaggccacc ttcctgccac agccttttcc ccaaacctgg tatcacccc  tctcctccct     240 ccctaatccc acctctcggg cctggccact ccacccacc ccttccagga ctcagattca      300
gactctgagg gaggagccgc tggtggagaa gcagacatgg acttcctgcg gaacttattc     360
tcccagacgc tcagcctggg cagccagaag gagcgtctgc tggacgagct gaccttggaa     420
ggggtggccc ggtacatgca gagcgaacgc tgtcgcagag tcatctgttt ggtgggagct     480
ggaatctcca catccgcagg catccccgac tttcgctctc catccaccgg cctctatgac     540
aacctagaga agtaccatct tccctaccca gaggccatct tgagatcag ctatttcaag      600 aaacatccgg aaccttctt cgccctcgcc aaggaactct atcctgggca gttcaagcca     660
accatctgtc actacttcat gcgcctgctg aaggacaagg gctactcct gcgctgctac      720 acgcagaaca tagataccct ggagcgaata gccgggctgg aacaggagga cttggtggag    780
gcgcacggca ccttctacac atcacactgc gtcagcgcca gctgccggca cgaatacccg    840
ctaagctgga tgaaagagaa gatcttctct gaggtgacgc ccaagtgtga agactgtcag    900
agcctggtga gcctgatat cgtctttttt ggtgagagcc tcccagcgcg tttcttctcc     960
tgtatgcagt cagacttcct gaaggtggac ctcctcctgg tcatgggtac ctccttgcag   1020
gtgcagccct tgcctccct catcagcaag gcaccctct ccaccctcg cctgctcatc      1080 aacaaggaga aagctggcca gtcggaccct ttcctgggga tgattatggg cctcggagga   1140
ggcatggact ttgactccaa gaaggcctac agggacgtgg cctggctggg tgaatgcgac   1200
cagggctgcc tggccttgc tgagctcctt ggatggaaga aggagctgga ggaccttgtc    1260
cggagggagc acgccagcat agatgcccag tcgggggcgg gggtcccaa ccccagcact    1320
```

-continued

| | |
|---|---|
| tcagcttccc ccaagaagtc cccgccacct gccaaggacg aggccaggac aacagagagg | 1380 |
| gagaaacccc agtgacagct gcatctccca ggcgggatgc cgagctcctc agggacagct | 1440 |
| gagccccaac cgggcctggc ccctcttaa ccagcagttc ttgtctgggg agctcagaac | 1500 |
| atcccccaat ctcttacagc tccctcccca aaactgggt cccagcaacc ctggcccca | 1560 |
| accccagcaa atctctaaca cctcctagag gccaaggctt aaacaggcat ctctaccagc | 1620 |
| cccactgtct ctaaccactc ctgggctaag gagtaacctc cctcatctct aactgcccc | 1680 |
| acggggccag ggctaccca gaactttaa ctcttccagg acagggagct cgggccccc | 1740 |
| actctgtctc ctgcccccgg gggcctgtgg ctaagtaaac catacctaac ctaccccagt | 1800 |
| gtgggtgtgg gcctctgaat ataacccaca cccagcgtag ggggagtctg agccgggagg | 1860 |
| gctcccgagt ctctgccttc agctcccaaa gtgggtggtg ggccccttc acgtgggacc | 1920 |
| cacttcccat gctggatggg cagaagacat tgcttattgg agacaaatta aaaacaaaaa | 1980 |
| caactaacaa tccggaaaaa aaaaaaaaa | 2009 |

<210> SEQ ID NO 137
<211> LENGTH: 2773
<212> TYPE: DNA
<213> ORGANISM: Homo sapiens
<300> PUBLICATION INFORMATION:
<308> DATABASE ACCESSION NUMBER: NM_001017524.2
<309> DATABASE ENTRY DATE: 2010-12-24
<313> RELEVANT RESIDUES IN SEQ ID NO: (1)..(2773)

<400> SEQUENCE: 137

| | |
|---|---|
| gcgagtccgg aggactcctt ggactgcgcg gaacatggcg ttctgggtt ggcgcgccgc | 60 |
| ggcagccctc cggctgtggg gccgggtagt tgaacgggtc gaggccgggg gaggcgtggg | 120 |
| gccgtttcag gcctgcggct gtcggctggt gcttggcggc agggacgatt attaaaggtg | 180 |
| gaagaaggtc catatctttt tctgtgggtg cttcaagtgt tgttggaagt ggaggcagca | 240 |
| gtgacaaggg gaagctttcc ctgcaggatg tagctgagct gattcgggcc agagcctgcc | 300 |
| agagggtggt ggtcatggtg ggggccggca tcagcacacc cagtggcatt ccagacttca | 360 |
| gatcgccggg gagtggcctg tacagcaacc tccagcagta cgatctcccg tacccccgagg | 420 |
| ccatttttga actcccattc ttctttcaca accccaagcc cttttttcact ttggccaagg | 480 |
| agctgtaccc tggaaaactac aagcccaacg tcactcacta cttctccgg ctgcttcatg | 540 |
| acaaggggct gcttctgcgg ctctacacgc agaacatcga tgggcttgag agagtgtcgg | 600 |
| gcatccctgc ctcaaagctg gttgaagctc atggaacctt tgcctctgcc acctgcacag | 660 |
| tctgccaaag acccttccca ggggaggaca ttcgggctga cgtgatggca gacagggttc | 720 |
| cccgctgccc ggtctgcacc ggcgttgtga agcccgacat tgtgttcttt ggggagccgc | 780 |
| tgccccagag gttcttgctg catgtggttg atttccccat ggcagatctg ctgctcatcc | 840 |
| ttgggacctc cctggaggtg gagcttttg ccagcttgac cgaggccgtg cggagctcag | 900 |
| ttccccgact gctcatcaac cgggacttgg tgggccctt ggcttggcat cctcgcagca | 960 |
| gggacgtggc ccagctgggg gacgtggttc acggcgtgga aagcctagtg gagcttctgg | 1020 |
| gctggacaga agagatgcgg gaccttgtgc agcgggaaac tgggaagctt gatgaccag | 1080 |
| acaaatagga tgatggctgc ccccacacaa taaatggtaa cataggagac atccacatcc | 1140 |
| caattctgac aagacctcat gcctgaagac agcttgggca ggtgaaacca gaatatgtga | 1200 |
| actgagtgga caccccgaggc tgccactgga atgtcttctc aggccatgag ctgcagtgac | 1260 |
| tggtagggct gtgtttacag tcagggccac cccgtcacat atacaaagga gctgcctgcc | 1320 |

```
tgtttgctgt gttgaactct tcactctgct gaagctccta atggaaaaag ctttcttctg    1380
actgtgaccc tcttgaactg aatcagacca actggaatcc cagaccgagt ctgctttctg    1440
tgcctagttg aacggcaagc tcggcatctg ttggttacaa gatccagact tgggccgagc    1500
ggtccccagc cctcttcatg ttccgaagtg tagtcttgag gccctggtgc cgcacttcta    1560
gcatgttggt ctcctttagt ggggctattt ttaatgagag aaaatctgtt ctttccagca    1620
tgaaatacat ttagtctcct caaagggact gcaggtgttg acatgagttg aaagggaac     1680 cctgggatac gtggcgtccc ctctattgga acagtctgag gactgaaggc atttgtccct    1740
ggatttattg gagacggccc agctcctccc tctgaaggtg gtcacattct gttgactctc    1800
catactcagc ctctcctcca gaaacagatc tgttccagaa cattccagca ctttctatct    1860
ggcctccttg tccccacact acgccccccc ccctcgcca gggcttcctc tagtgacact     1920
gttagagcta atctctgaga cagggaaggc attactcact taaaacccag gctgagtcct    1980
ggccacctgc tggattgtga cataggaggt ggaatccact gaactgctac ttctgcacag    2040
gctccttctc ctggggctgt acccaggccc agccctgatg gctcaccctg tcaggcacca    2100
gctgctccct cctgggctct cacccacctg cacatcctcc ttcctagcat cacattacct    2160
gcgtgtttcc ccagacaaaa gcacttccca ttcttgaacc ttgcctaccc tgggctgagc    2220
tgacggcaat agatttaatg acagtgactc caggaaggg ggtcctgtga ctttgcgcct     2280
taataagaac aaaaggtgga attggtgacc taggaaaact gttgaattct aaaaagaatg    2340
aagttagttt ctaaccctag ttaatgttcc ttttttattt tttgagtctt gccctgtcac    2400
tcagggtgga gtgcggtgtt atgatctcag ctcactgcaa cttccgcctc ccgggtttaa    2460
gcgattctcc tgggtagctg ggattacagg tgtgtcccac cacacctagc acatgggcat    2520
atttgtaata gagacaaggt tttgctatgt tggccaggct ggtctcgaac tcctggcttc    2580
aagtgatcca cccacctcgg cctcccaaag tgctgggatt acaggcatga gccactgtgc    2640
ctggcccctt tatttgataa tttacacata catttttgtc caaaactctt ctttatttca    2700
agatgatgtt tctgtggcta tgtgtggtat gtggtataaa tctcaatcta tggtcaaaaa    2760
aaaaaaaaaa aaa                                                       2773
```

<210> SEQ ID NO 138
<211> LENGTH: 2398
<212> TYPE: DNA
<213> ORGANISM: Homo sapiens
<300> PUBLICATION INFORMATION:
<308> DATABASE ACCESSION NUMBER: NM_031244.2
<309> DATABASE ENTRY DATE: 2010-12-26
<313> RELEVANT RESIDUES IN SEQ ID NO: (1)..(2398)

<400> SEQUENCE: 138

```
tgggagggag gcaccccggg gggcggggcg tgggagactg tattcggggg cgcgagctgc      60
cccagtaaat ggaaatgttt tctaacatat aaaaacctac agaagaagaa ataattttc      120 tggatcaaat tagaagtctg tattatattg atgtctccag attcaaatat attagaaagc     180
agccgtggag acaaccatct tcattttggg agaaataact aaagcccgcc tcaagcatta     240
gaactacaga caaaccctga tgcgacctct ccagattgtc ccagtcgat tgatttccca      300 gctatattgt ggcctgaagc ctccagcgtc cacacgaaac cagatttgcc tgaaaatggc     360
tcggccaagt tcaagtatgg cagattttcg aaagtttttt gcaaaagcaa agcacatagt     420
catcatctca ggagctggtg ttagtgcaga aagtggtgtt ccgaccttca gaggagctgg     480
```

```
aggttattgg agaaaatggc aagcccagga cctggcgact ccctggcct ttgcccacaa      540 cccgtcccgg gtgtgggagt tctaccacta ccggcgggag gtcatgggga gcaaggagcc      600
caacgccggg caccgcgcca tagccgagtg tgagacccgg ctgggcaagc agggccggcg      660
agtcgtggtc atcacccaga acatcgatga gctgcaccgc aaggctggca ccaagaacct      720
tctggagatc catggtagct atttaaaac tcgatgtacc tcttgtggag ttgtggctga       780
gaattacaag agtccaattt gtccagcttt atcaggaaaa ggtgctccag aacctggaac      840
tcaagatgcc agcatcccag ttgagaaact cccccggtgt gaagaggcag gctgcggggg      900
cttgctgcga cctcacgtcg tgtggtttgg agaaaacctg gatcctgcca ttctggagga      960
ggttgacaga gagctcgccc actgtgattt atgtctagtg gtgggcactt cctctgtggt     1020
gtacccagca gccatgtttg ccccccaggt ggctgccagg ggcgtgccag tggctgaatt     1080
taacacggag accacccag ctacgaacag attcagtcat ttgatctcca tctcatctct     1140
aattattata aagaattaaa acaagtcatc attgtagaaa agcaagaaaa tgcagataga     1200 gaaaagaag aaaataaaac tggagtattt ccacaaccca agtttagagt tggcccccac      1260
ctcccatgcc atggactgag cagcaggggc ccagcatccc ttggatatgg tggctgtgtc     1320
ttcatgtgaa agaaactgaa cttggtggtt tttcctgcca gttcaggaga gattcttggc     1380
atgtaatata tatcactgct caagtcaagc ctcctaaaac cacagacctg tttcagctgc     1440
tacttcagcc aaaattcttc agcttcatat tgtcttgaaa acctatgatt gtctctaaca     1500
aacaggctac ttgctagtta gaaattctta tcaatttggc aagctactta tcaaccagac     1560
tgaccacaag aactgtcatc tcatcaatga aggagtaact gatcaatgaa gccagcaatg     1620 ctttttttctt ggcatcatca aagctgacat ttagaagaga tgctggtgat agtcatctca     1680
tcctactcaa tttttcaaag gcagaaacca accctggagc aattgagagg actgtttaaa     1740
cacagagctt aacaatggca gaattgtata tctcgtgctt aacagatttt ggttgaactt     1800
taccctaggt caggggtcag caaactactg cctgtgggcc aaatttgccc accacctgta     1860
tctgtaaata aggtttcatt ggaacacagc tgtggccata tgtttgtata ttgtgtgtgg     1920
ctgcttttgc attaggatga cagaggtgaa tagttgcaac agagactggc tggtctgcaa     1980
agcctaaaat atgtcctgtg tggcccttta cagaaaagt tttctaaccc ctgctctagg       2040
ttacggagaa aaaaaaatg gaataatgtt ctctgctact tttaacctga ttttctttgt       2100
tacctaaata ggcagctaga atgctgccta tattttaata aggatttgga tctcacaaga     2160
caccttaggc cttacacaag ttgttcagat tctttgcccc agttctaatc tagtgacaaa     2220
ggcatagaat tctcctccca caggaatgta tttctatttt caaggtgtta attagttcca     2280
gttttggttt tgtcgttttc cccatgtccg atgcttatat tggatgattt ctgataaacc     2340
ctgactattc caataaaccc taggcatttt tgaatttaaa aaaaaaaaa aaaaaaa        2398
```

<210> SEQ ID NO 139
<211> LENGTH: 3831
<212> TYPE: DNA
<213> ORGANISM: Homo sapiens
<300> PUBLICATION INFORMATION:
<308> DATABASE ACCESSION NUMBER: NM_001193267.1
<309> DATABASE ENTRY DATE: 2010-12-20
<313> RELEVANT RESIDUES IN SEQ ID NO: (1)..(3831)

<400> SEQUENCE: 139

```
tgggagggag gcaccccggg gggcggggcg tgggagactg tattcggggg cgcgagctgc       60
cccagtaaat ggaaatgttt tctaacatat aaaaacctac agaagaagaa aataattttc      120
```

```
tggatcaaat tagaagtctg tattatattg atgtctccag attcaaatat attagaaagc    180
agccgtggag acaaccatct tcattttggg agaaataact aaagcccgcc tcaagcatta    240
gaactacaga caaaccctga tgcgacctct ccagattgtc ccaagtcgat tgatttccca    300
gctatattgt ggcctgaagc ctccagcgtc cacacgaaac cagatttgcc tgaaaatggc    360
tcggccaagt tcaagtatgg cagattttcg aaagttttt gcaaaagcaa agcacatagt     420
catcatctca ggagctggtg ttagtgcaga agtggtgtt ccgaccttca gaggagctgg     480
aggttattgg agaaaatggc aagcccagga cctggcgact cccctggcct ttgcccacaa    540
cccgtcccgg gtgtgggagt tctaccacta ccggcgggag gtcatgggga gcaaggagcc    600
caacgccggg caccgcgcca tagccgagtg tgagacccgg ctgggcaagc agggccggcg    660
agtcgtggtc atcacccaga acatcgatga gctgcaccgc aaggctggca ccaagaacct    720
tctggagatc catggtagct atttaaaaac tcgatgtacc tcttgtggag ttgtggctga    780
gaattacaag agtccaattt gtccagcttt atcaggaaaa gggtgtgaag aggcaggctg    840
cggggggcttg ctgcgacctc acgtcgtgtg gtttggagaa aacctggatc ctgccattct    900
ggaggaggtt gacagagagc tcgcccactg tgatttatgt ctagtggtgg gcacttcctc    960
tgtggtgtac ccagcagcca tgtttgcccc ccaggtggct gccaggggcg tgccagtggc   1020
tgaatttaac acggagacca ccccagctac gaacagattc aggtttcatt tccagggacc   1080
ctgtggaacg actcttcctg aagcccttgc ctgtcatgaa aatgaaactg tttcttaagt   1140
gtcctgggga agaaagaaat tacagtatat ctaagaacta ggccacacgc agaggagaaa   1200
tggtcttatg ggtggtgagc tgagtactga acaatctaaa aatagcctct gattccctcg   1260
ctggaatcca acctgttgat aagtgatggg ggtttagaag tagcaaagag cacccacatt   1320
caaaagtcac agaactggaa agttaattca tattatttgg tttgaactga acgtgaggt    1380
atctttgatg tgtatggttg gttattggga gggaaaaatt ttgtaaatta gattgtctaa   1440
aaaaaatagt tattctgatt atatttttgt tatctgggca aagtagaagt caaggggtaa   1500
aaacccctact attctgattt ttgcacaagt tttagtggaa aataaaatca cactctacag   1560
taggtaattt attgtataaa gacattaccc cacgatatgg ctttattagg actttttttt   1620
tttttttttt gagacagagt ttcactcttg ttgcccaggc tggagtgcag tggtgcgatc   1680
tcagctcaca gcaacctccg cctcccgggt tcaagagatt ctcctgcctc agcctcatga   1740
gtagctggga ttacaggtat gtaccaccac acccagctaa ttttgtattt ttagtagaga   1800
cggggttct ccatgttggt caggctggtc ttaaactctc gacctcaggt gatctgcccg    1860
cctcggcctc ccaaagtgct gagattacgg gcatgagcca ccgcacccgg cttactgggg   1920
gcttttaac cttgtttggc tacattacct cagtgaacaa ggggaagctc acaacaggaa    1980
ctcacacaaa gaaggaagag aacagtacca acaaggtaga acatcacgat gagaagaaag   2040
aatgatgcaa atatgtggac ccccaggata aacacagctg cccaaaattt agctctggcc   2100
cccttagatg ggggaagtca acagtgaagt gtttctcagc atcataaagg cagaagctgt   2160
ggttcctgtg gggcctgcca accgttccca gatgctgaac tctgctggga gttttttcca   2220
tgggacttta aaaaatgatg cccttaggtt gggccagacc tctgttaact tcagtaggga   2280
tggcaccagg ttcaagaggc caaagaagag acctggagct agtgaaggaa acatagggtt   2340
tatttgggga accttacagg gtggtccagt ggccgcgggc tggacagaac tgcaaccact   2400
tataaaaagc atgcagttta catagcactt tcactcagca ccctcccctc agcagcctcc   2460
```

| | | | | |
|---|---|---|---|---|
| acgtggcaac | cctcacttct | taagttattg | ctgtcagatg | catctgccat acagggtcat | 2520 |
| tctcagggga | tgcttaagtt | atttctgtca | ggtacatctt | ccatacactt tactaccttg | 2580 |
| gagtaaagta | gtaagaatac | agcttttttcc | ttaacccttta | ccagctaact cagtgcttag | 2640 |
| gggccttgga | atgcctgctg | tccagcaggt | gtcacaggcc | tgactgggag gcatggccat | 2700 |
| tatcaacagt | gtatgaaggt | cacatatggc | tccctgaagt | gattacatac ttggaccaca | 2760 |
| tcacctcagc | cccttgcaaa | attgcattta | atgttacacc | cttggctttt gtagaaacag | 2820 |
| gcaacaagac | actatcatat | aaaactttgt | actgcattgc | aaggcataac ctttaataaa | 2880 |
| tcccagtggt | cctttgtgta | gggaacgggg | atgctcatag | cctatggggc ggctggagaa | 2940 |
| ccagtcaggg | accctgaggg | ctcgatgtac | actttacatg | ggtgggccaa ggagtttaca | 3000 |
| ctgagggcac | tggtaatacc | tgtaatagtc | ttatagtact | tataaagcag ttttgcacat | 3060 |
| aaaataccat | catgcactta | taagtttgtt | cttgggctgc | tccaagttaa ctttattcat | 3120 |
| tttcctagtg | ttagtgtctc | agggagtctg | attatatttt | tgatttgtaa tttctatctg | 3180 |
| actaaggcct | agagatttca | aaactgttct | ttgcaattcc | tctcatactg aacctctggt | 3240 |
| tcagcagctt | tttttgttgt | tgttgttttc | aagtttatc | attttttgttc ctatttggtt | 3300 |
| ttgtcgtttt | taaattgaga | attgcttcta | aaacagaaga | catgaaaaga gaattaaaaa | 3360 |
| tacaatatat | gtgtaagata | gaattattca | acttagcatt | tattaaacat ctaccagatg | 3420 |
| atagacatta | gaaataaaat | gactagcaag | acctggcccct | tccccctcagg ggttcacaga | 3480 |
| atggctggag | caactgtcat | ataagctgtt | atgaagtgca | gaaactacac agacatttgt | 3540 |
| gcgggttcag | accagcgcaa | ttagagatgg | gcagagtggg | atggggtagg ggtaaggtgc | 3600 |
| ttgaaatttg | cctgggtggg | aattttttgaa | gtataaaaag | gacttctacc tgggggggctg | 3660 |
| cggcagtaga | gggaagagca | cggtcggtac | aaatgcatgg | caggtgtgaa acagtttgat | 3720 |
| ttgttcaaag | aatgatgaat | cacttagtgt | tgtataatgg | atgggaggag agaaacacag | 3780 |
| cgatcacaaa | gggccatgtt | tgccaagaaa | taaaatatac | ttggaaaaaa a | 3831 |

<210> SEQ ID NO 140
<211> LENGTH: 1555
<212> TYPE: DNA
<213> ORGANISM: Homo sapiens
<300> PUBLICATION INFORMATION:
<308> DATABASE ACCESSION NUMBER: NM_001193285.1
<309> DATABASE ENTRY DATE: 2010-10-03
<313> RELEVANT RESIDUES IN SEQ ID NO: (1)..(1555)

<400> SEQUENCE: 140

| | | | | |
|---|---|---|---|---|
| gcttccggcg | gaagcggcct | caacaaggga | aactttattg | ttcccgtggg gcagtcgagg | 60 |
| atgtcggtga | attacgcggc | ggggctgtcg | ccgtacgcgg | acaagggcaa gtgcggcctc | 120 |
| ccggagatct | tcgaccccccc | ggaggagctg | gagcggaagg | tgtgggaact ggcgaggctg | 180 |
| gtctggcagt | cttccagtgt | ggtgttccac | acgggtgccg | gcatcagcac tgcctctggc | 240 |
| atccccgact | tcagggggtcc | ccacggagtc | tggaccatgg | aggagcgagg tctggcccccc | 300 |
| aagttcgaca | ccacccttttga | gagcgcgcgg | cccacgcaga | cccacatggc gctggtgcag | 360 |
| ctggagcgcg | tgggcctcct | ccgcttcctg | gtcagccaga | acgtggacgg gctccatgtg | 420 |
| cgctcaggct | tccccaggga | caaactggca | gagctccacg | ggaacatgtt tgtggaagaa | 480 |
| tgtgccaagt | gtaagacgca | gtacgtccga | gacacagtcg | tgggcaccat gggcctgaag | 540 |
| gccacgggcc | ggctctgcac | cgtggctaag | gcaggggggc | tgcagagctg caggaacgcc | 600 |
| gacctgtcca | tcacgctggg | tacatcgctg | cagatccggc | ccagcgggaa cctgccgctg | 660 |

```
gctaccaagc gccggggagg ccgcctggtc atcgtcaacc tgcagcccac caagcacgac    720
cgccatgctg acctccgcat ccatggctac gttgacgagg tcatgacccg gctcatgaag    780
cacctggggc tggagatccc cgcctgggac ggccccgtg tgctggagag ggcgctgcca     840
cccctgcccc gcccgcccac ccccaagctg agcccaagg aggaatctcc cacccggatc     900
aacggctcta tccccgccgg ccccaagcag gagccctgcg cccagcacaa cggctcagag    960
cccgccagcc ccaaacggga gcggcccacc agccctgccc ccacagacc ccccaaaagg     1020 gtgaaggcca aggcggtccc cagctgacca gggtgcttgg ggagggtggg cttttttgta    1080
gaaactgtgg attcttttc tctcgtggtc tcactttgtt acttgtttct gtccccggga     1140
gcctcagggc tctgagagct gtgctccagg ccaggggtta cacctgccct ccgtggtccc    1200
tccctgggct ccaggggcct ctggtgcggt tccgggaaga agccacaccc cagaggtgac    1260
aggtgagccc ctgccacacc ccagcctctg acttgctgtg ttgtccagag gtgaggctgg    1320
gccctccctg gtctccagct taaacaggag tgaactccct ctgtcccag gcctcccctt     1380 ctgggccccc tacagcccac cctacccctc ctccatgggc cctgcaggag ggagaccca     1440 ccttgaagtg ggggatcagt agaggcttgc actgcctttg gggctggagg gagacgtggg    1500
tccaccaggc ttctggaaaa gtcctcaatg caataaaaac aatttctttc ttgca         1555

<210> SEQ ID NO 141
<211> LENGTH: 2714
<212> TYPE: DNA
<213> ORGANISM: Homo sapiens
<300> PUBLICATION INFORMATION:
<308> DATABASE ACCESSION NUMBER: NM_021932.4
<309> DATABASE ENTRY DATE: 2010-12-26
<313> RELEVANT RESIDUES IN SEQ ID NO: (1)..(2714)

<400> SEQUENCE: 141
gcagggcacg gtgggggctg agatcgtttc ctgttggaac ttctggccca agaagcgcgg    60
gtcacaagga gagggtcag ttcggttcag agcgactcag cccctcgact cgggtcttaa     120
aacctccgag ccgccagttc tgcctcaggc cgcgcccccct aaagcgcca ccagacgctg    180 cgccccgtta aagcgccacc agacgccgcg ccccgtcccg gcctccccg cgcgctggcg    240 cggggctttc tgggccaggg cggggccggc gaactgcggc ccggaacggc tgaggaaggg    300
cccgtcccgc cttccccggc gcgccatgga gccccgggcg gttgcagaag ccgtggagac    360
gggtgaggag gatgtgatta tggaagctct gcggtcatac aaccaggagc actcccagag    420
cttcacgttt gatgatgccc aacaggagga ccggaagaga ctggcggagc tgctggtctc    480
cgtcctggaa cagggcttgc caccctccca ccgtgtcatc tggctgcaga gtgtccgaat    540
cctgtcccgg gaccgcaact gcctggaccc gttcaccagc cgccagagcc tgcaggcact    600
agcctgctat gctgacatct ctgtctctga ggggtccgtc ccagagtccg cagacatgga    660
tgttgtactg gagtccctca gtgcctgtg caacctcgtg ctcagcagcc tgtggcaca     720 gatgctggca gcagaggccc gcctagtggt gaagctcaca gagcgtgtgg ggctgtaccg    780
tgagaggagc ttcccccacg atgtccagtt ctttgacttg cggctcctct tcctgctaac    840
ggcactccgc accgatgtgc gccagcagct gtttcaggag ctgaaggag tgcgcctgct    900 aactgacaca ctggagctga cgctgggggt gactcctgaa gggaacccc cacccacgct    960 ccttccttcc caagagactg agcgggccat ggagatcctc aaagtgctct tcaacatcac    1020
cctggactcc atcaaggggg aggtggacga ggaagacgct gccctttacc gacacctggg    1080
```

```
gacccttctc cggcactgtg tgatgatcgc tactgctgga gaccgcacag aggagttcca    1140
cggccacgca gtgaacctcc tggggaactt gcccctcaag tgtctggatg ttctcctcac    1200
cctggagcca catggagact ccacggagtt catgggagtg aatatggatg tgattcgtgc    1260
cctcctcatc ttcctagaga agcgtttgca caagacacac aggctgaagg agagtgtagc    1320
tcccgtgctg agcgtgctga ctgaatgtgc ccggatgcac cgcccagcca ggaagttcct    1380
gaaggcccag ggatggccac ctccccaggt gctgcccct ctgcgggatg tgaggacacg    1440
gcctgaggtt ggggagatgc tgcggaacaa gcttgtccgc ctcatgacac acctggacac    1500
agatgtgaag agggtggctg ccgagttctt gtttgtcctg tgctctgaga gtgtgccccg    1560
attcatcaag tacacaggct atgggaatgc tgctggcctt ctggctgcca ggggcctcat    1620
ggcaggaggc cggcccgagg ccagtactc agaggatgag gacacagaca cagatgagta    1680
caaggaagcc aaagccagca taaaccctgt gaccgggagg gtggaggaga agccgcctaa    1740
ccctatggag ggcatgacag aggagcagaa ggagcacgag gccatgaagc tggtgaccat    1800
gtttgacaag ctctccagga acagagtcat ccagccaatg gggatgagtc cccggggtca    1860
tcttacgtcc ctgcaggatg ccatgtgcga gactatggag cagcagctct cctcggaccc    1920
tgactcggac cctgactgag gatggcagct cttctgctcc cccatcagga ctggtgctgc    1980
ttccagagac ttccttgggg ttgcaacctg gggaagccac atcccactgg atccacaccc    2040
gcccccactt ctccatctta gaaaccccct tcttgactc ccgttctgtt catgatttgc    2100
ctctggtcca gtttctcatc tctggactgc aacggtcttc ttgtgctaga actcaggctc    2160
agcctcgaat tccacagacg aagtactttc ttttgtctgc gccaagagga atgtgttcag    2220
aagctgctgc ctgagggcag ggcctacctg gcacacaga agagcatatg ggagggcagg    2280
ggtttgggtg tgggtgcaca caaagcaagc accatctggg attggcacac tggcagagcc    2340
agtgtgttgg ggtatgtgct gcacttccca gggagaaaac ctgtcagaac tttccatacg    2400
agtatatcag aacacaccct tccaaggtat gtatgctctg ttgttcctgt cctgtcttca    2460
ctgagcgcag ggctggaggc ctcttagaca ttctccttgg tcctcgttca gctgcccact    2520
gtagtatcca cagtgcccga gttctcgctg gtttttggcaa ttaaacctcc ttcctactgg    2580
tttagactac acttacaaca aggaaaatgc ccctcgtgtg accatagatt gagatttata    2640
ccacatacca cacatagcca cagaaacatc atcttgaaat aaagaagagt tttggacaaa    2700
aaaaaaaaaa aaaa                                                     2714
```

<210> SEQ ID NO 142
<211> LENGTH: 1757
<212> TYPE: DNA
<213> ORGANISM: Homo sapiens
<300> PUBLICATION INFORMATION:
<308> DATABASE ACCESSION NUMBER: NM_002817.3
<309> DATABASE ENTRY DATE: 2010-12-26
<313> RELEVANT RESIDUES IN SEQ ID NO: (1)..(1757)

<400> SEQUENCE: 142

```
tttgacgcct caatggcaca gccaagtgcg cgggaagtgg gctgcaaacg ccggagagtt     60 tgtccggag cgcagagacg cgctgtaacc gagcaaccag cggggcccgc cccggcctg     120 ctacggcgct cccagcctgc cccgcgccgc tcggcgccgg aagtgagtga gcatttccgg    180
cagccatccc cgcggtgctg acatcccggt tgttcttctg tgccgggggt cttcctgctg    240
tcatgaagga cgtaccgggc ttcctacagc agagccagaa ctccgggccc gggcagcccg    300
ctgtgtggca ccgtctggag gagctctaca cgaagaagtt gtggcatcag ctgacacttc    360
```

```
aggtgcttga ttttgtgcag gatccgtgct tgcccaagg agatggtctc attaagcttt      420
atgaaaactt tatcagtgaa tttgaacaca gggtgaaccc tttgtccctc gtggaaatca      480
ttcttcatgt agttagacag atgactgatc ctaatgtggc tcttacttt ctggaaaaga       540 ctcgtgagaa ggtgaaaagt agtgatgagg cagtgatcct gtgtaaaaca gcaattggag      600
ctctaaaatt aaacatcggg gacctacagg ttacaaagga acaattgaa gatgttgaag       660 aaatgctcaa caaccttcct ggtgtgacat cggttcacag tcgtttctat gatctctcca      720
gtaaatacta tcaaacaatc ggaaaccacg cgtcctacta caaagatgct ctgcggtttt      780
tgggctgtgt tgacatcaag gatctaccag tgtctgagca gcaggagaga gccttcacgc      840
tggggctagc aggacttctc ggcgagggag ttttttaactt tggagaactc ctcatgcacc     900
ctgtgctgga gtccctgagg aatactgacc ggcagtggct gattgacacc ctctatgcct      960
tcaacagtgg caacgtagag cggttccaga ctctgaagac tgcctggggc cagcagcctg     1020
atttagcagc taatgaagcc cagcttctga ggaaaattca gttgttgtgc ctcatggaga     1080
tgactttcac acgacctgcc aatcacagac aactcacttt tgaagaaatt gccaaaagtg     1140
ctaaaatcac agtgaatgag gtggagcttc tggtgatgaa ggcccttcg gtggggctgg      1200 tgaaaggcag tatagacgag gtggacaaac gagtccacat gacctgggtg cagccccgag     1260
tgttggattt gcaacagatc aagggaatga aggaccgcct ggagttctgg tgcacggatg     1320
tgaagagcat ggagatgctg gtggagcacc aggcccatga catcctcacc tagggccccc     1380
tggttccccg tcgtgtctcc tttgactcac ctgagagagg cgtttgcagc caatgaagct     1440
ggctgctcag acggtcgaca ttgaatttgg gtggggttg ggatcctgtc tgaagtacag      1500
actgttcttg ctctaaaaac aggactgtcc ctgatgggag ccaggccaca gggaggaggc     1560
ttctttgtgg gtctctcctg cagagggtgg gggtctcagg gtcttaggtg atacgggaga     1620
gaaagaacgt gccaggcagg aggcccctg aagtctgtgt actccgaggt ggatctccat      1680
ccccatccac ctgtacggac atcttttccg ttgcggtttg agaatgttcc tataataaac      1740
ccctctgctt tgttctt                                                    1757
```

<210> SEQ ID NO 143
<211> LENGTH: 3647
<212> TYPE: DNA
<213> ORGANISM: Homo sapiens

<400> SEQUENCE: 143

```
catgtcagga aagttcaaac atttccttct aataaggaag atatctttga aatagtcttt       60
tgtaataaaa atgccatttt atttatttat tattattatt ttttgagacg gagtttcatt      120
cttatcaccc aggctggagt gcaatggcac agtctcagct cactcatcc tcctcctccc       180 gggttccagt gattctcctg ccacagcctc cagagtagct gggattacag gcacccgcca      240
ccacgcctgg ataattttg tattttagt agagacaggg tttcatcatg ttgaccaggc        300
tggtctcaaa ctcctaacct caggcgatcc accgccttg gcctcccaaa gtgctgggat      360
tacaggtgtg aaccaccacc tggccaccat tttattat tgggtgggc aaagggacag         420 agtctcgcac tgtcgcccag gctggagtgc aatggcagat ctcagctcgc tgcaacctcc     480
gtctccccag ttcaagccat tctcatgcct cagcctccca gtagctggg attacaagcg     540 tgtgccacca cacctggcta atttttgtag ttttagtaga gatggcattt caccatgttg     600
gccaggctgg tcttgaactc ctgtcctcac gtgatccacc agcctcggcc tcccaaagtg     660
```

| | |
|---|---|
| ctacataaca gacgtgagcc acagcaccgg gacaaaaatg ccattttatt tagttgactg | 720 |
| tttcttgtgt gcctgattgg aatatgtaat tgctacaggg gtgttttcat ccttctacct | 780 |
| tcatatccca gaggaactac aggctctcct aatccaaagt taaggtcatt tggaggttcc | 840 |
| ctctcctact gtgcccacac taggcgctct tggcccagtt acccctaact caggggttat | 900 |
| tgtcagctct ccttctctgt gaccggccca catctgagtg agtctggttc gttacccta | 960 |
| aatctctctc aaattattca tccatcctca ttacggttgc tccctcactc tcctgtcttg | 1020 |
| gccagtacta gcctctgact gttctctctc agtctctttc acctgctgtc ctctctgccc | 1080 |
| caggcgtgtt tctaaaatag aaatgatcat gtgtgtcctc tggttcggcc ttgcactctg | 1140 |
| gacagagacc aatcttcagt gcttcctagt ctgtgtccct cagaaatgcc cctgaaacat | 1200 |
| aatgtatttt tttcttcagt gcttttgcac atgtttgtta ctgtctggaa tgttcttctc | 1260 |
| tcagcttctt cccctcccac accaaatggc cacctctcta accgcccttc attccttgaa | 1320 |
| actcagtatt gccacttcta cagtaacctt tgaagcctct cccttttggct gatgcacttc | 1380 |
| tgccccttttt tttttctttc tttcttttttg ctcttaaact cactgtattg tcatttattt | 1440 |
| gtttaaagac tgtcttcagt ggaccaggag ctccttgaag acacatcatt tgtcttacac | 1500 |
| gttctatgtt gtagtatcta gtatggagtc tgaggaagtg ctcaagtgtg ctgaatggct | 1560 |
| aagaaatttg aaaacggtgc ataattagct ttaattaaaa tctgaaggaa ctccattctg | 1620 |
| tttgattagc aaacatttct ctttttgttt taaattttat ttcattaact taataggtga | 1680 |
| acaaaatgtg tatttcaaat ctaattgaaa ttcatctgaa acatgtttac acagaagata | 1740 |
| gatataagat ttcaagtaac ttattgtaca gtccattgtc cattttaaga tattctttct | 1800 |
| tccaaaaaaa ctgcgttgaa tgtcaaaaaa aatcttttat actccataaa attgagatgc | 1860 |
| aaacttctga tataaatttt tttcactgtc aactccgatg ataaagatgg gaggcacaag | 1920 |
| cgttcacagt tcagttaaat gatgcaaacg aaaagcttct gttttccttt gatacaaatt | 1980 |
| agaagcctcc attcaggtct cttacagtag taccgcatac ttgatcctga tactacatta | 2040 |
| tgtctttttc ttttctctt ttttttttga gatggagttt cactcttgtt gcctaggctg | 2100 |
| gaatgcaatg gcacaatctc agctcacagc aacctctgcc tccctggttc aagcgattct | 2160 |
| tctgcctcag cctcccaagt agctgggact acaggcgcgc gccaccatgc ccagctgatt | 2220 |
| tttgtatttt tagtagagac ggggtttcac catgttgacc aggatggttc caatctcttg | 2280 |
| acctcatgat ccacccacct ctgcctccca aagtgctggg attacaggcg tgagccactg | 2340 |
| cgcccggatg gttacgtctt tttctttccc tttttttact tccctctcct tgttgaagac | 2400 |
| tttggtcacc acctcctgtt tttttgtgtc cttgttttta atttaggtat catttatgct | 2460 |
| gcacacaaca ttactgactt aacgtggtgg gaaatgtaca agatagaggc tgccattttc | 2520 |
| ctgtttgagc tgggcccaga ttctgctttt atattgaaca tcacgattcc attctctaga | 2580 |
| gaacatttta ttttctcaa gaaatgcatt aagtccaact gctaaacata gatcttgaat | 2640 |
| ctctagctgt aggattttca acagtcttac ttatggggat tcaccttcct tccacaatgg | 2700 |
| tcttattatt taaatgagta ggacagatac aaataaacct gaacatagat cttgaatctc | 2760 |
| tggctgtagg attttcaaca gccttactta tgggattcac cttccttcca cagtggtctt | 2820 |
| cttattattt aaataagcag gatagataca aataaacctg tcctggtagg ctggggacca | 2880 |
| cacggcagcg caggccatct tcacaagggt ccaaatacca acagcccgga agccacaggg | 2940 |
| agagaactga gggagcgttt caatctgata gtctatttag cttacagtac ctggaagaaa | 3000 |
| gaatatagga atctgtctgg aggttcttat aggtcagtac tctaattccc aaaactagaa | 3060 |

```
gaaacctaat attccttagt aatctgttga tcatttatgt gaatgtaagt aagccctgat    3120
atggtctcct atcattctgc aaacatgcat tgcttactgt gtgctgggca ctgtggcttg    3180
cacactccca acttgatagc attgatgcag cttctttacc aaagatagtg tttggggtct    3240
tcgttttgca gaataaaaga catcctataa tttctctcca tgttttggtt tcacagcttt    3300
atgaaaactt tatcagtgaa tttgaacaca ggtaaaagcc tctcatccgt ttttcacttt    3360
gaaaatgagt gcattgatgc tcggcggtgc tcaaaggctg gtggcttta tttcagggtg     3420 aaccctttgt ccctcgtgga aatcattctt catgtagtta gacagatgac tggtaagtct    3480
cactttgttt tataaaggag cagatccaaa tggtggttaa aattgaaata taagttaact    3540
gaacttttgt gttttctgta tcagatatta tgtttttatt atactttatg gtcaaaacct    3600
aaagattacc ctacctaagg gtgtcttggt tagcagaaac cagtctg                 3647

<210> SEQ ID NO 144
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 126

<400> SEQUENCE: 144
gcaccaucug ggauuggcac acugg                                            25

<210> SEQ ID NO 145
<211> LENGTH: 25
<212> TYPE: DNA
<213> ORGANISM: Artificial Sequence
<220> FEATURE:
<223> OTHER INFORMATION: Reverse complement of the antisense
      oligonucleotide SEQ ID NO: 127

<400> SEQUENCE: 145
caaggaucua ccagugucug agcag                                            25
```

TREATMENT OF SIRTUIN (SIRT) RELATED DISEASES BY INHIBITION OF NATURAL ANTISENSE TRANSCRIPT TO A SIRTUIN (SIRT)

The present application is a divisional of U.S. application Ser. No. 13/695,801 filed on Nov. 2, 2012, now U.S. Pat. No. 9,089,588, which is a National Stage Entry of International Application No. PCT/US2011/021052 filed on Jan. 13, 2011, which claims priority to U.S. Provisional Application Nos. 61/415,891 filed on Nov. 22, 2010, 61/412,066 filed Nov. 10, 2010, 61/409,136 filed Nov. 2, 2010, and 61/330,427 filed May 3, 2010, which are all incorporated herein by reference in their entireties.

FIELD OF THE INVENTION

Embodiments of the invention comprise oligonucleotides modulating expression and/or function of a Sirtuin (SIRT) and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of a Sirtuin (SIRT) polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 1028 of SEQ ID NO: 9 or nucleotides 1 to 429 of SEQ ID NO: 10, or nucleotides 1 to 508 of SEQ ID NO: 11 or nucleotides 1 to 593 of SEQ ID NO: 12, 1 to 373 of SEQ ID NO: 13, 1 to 1713 of SEQ ID NO: 14, 1 to 660 of SEQ ID NO: 15, 1 to 589 of SEQ ID NO: 16, 1 to 726 of SEQ ID NO: 17, 1 to 320 of SEQ ID NO: 18, 1 to 616 of SEQ ID NO: 19, 1 to 492 of SEQ ID NO: 20, 1 to 428 of SEQ ID NO: 21, 1 to 4041 of SEQ ID NO: 22 or 1 to 705 of SEQ ID NO: 23 or 1 to 2714 of SEQ ID NO: 141 or 1 to 1757 of SEQ ID NO: 142 or 1 to 3647 of SEQ ID NO: 143, thereby modulating function and/or expression of the Sirtuin (SIRT) polynucleotide in patient cells or tissues in vivo or in vitro.

In another embodiment, an oligonucleotide targets a natural antisense sequence of a Sirtuin (SIRT) polynucleotide, for example, nucleotides set forth in SEQ ID NO: 9 to 23, 141 to 143, and any variants, alleles, homology, mutants, derivatives, fragments and complementary sequences thereto. Examples of antisense oligonucleotides useful in practicing the methods of the present invention are set forth as SEQ ID NOS: 24 to 127.

Another embodiment provides a method of modulating function and/or expression of a Sirtuin (SIRT) polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of an antisense of the Sirtuin (SIRT) polynucleotide; thereby modulating function and/or expression of the Sirtuin (SIRT) polynucleotide in patient cells or tissues is vivo or in vitro.

Another embodiment provides a method of modulating function and/or expression of a Sirtuin (SIRT) polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to a Sirtuin (SIRT) antisense polynucleotide; thereby modulating function and/or expression of the Sirtuin (SIRT) polynucleotide in patient cells or tissues in vivo or in vitro.

In one embodiment, a composition comprises one or more antisense oligonucleotides which bind to sense and/or antisense Sirtuin (SIRT) polynucleotides.

In another embodiment, the oligonucleotides comprise one or more modified or substituted nucleotides.

In another embodiment, the oligonucleotides comprise one or more modified bonds.

In yet another embodiment, the modified nucleotides comprise modified bases comprising phosphorothioate, methylphosphonate, peptide nucleic acids, 2'-O-methyl, flouro- or carbon, methylene or other locked nucleic acid (LNA) molecules. Preferably, the modified nucleotides are locked nucleic acid molecules, including α-L-LNA.

In another embodiment, the oligonucleotides are administered to a patient subcutaneously, intramuscularly, intravenously or intraperitoneally.

In another embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another embodiment, the oligonucleotides are encapsulated in a liposome or attached to a carrier molecule (e.g. cholesterol, TAT peptide).

Other aspects are described infra.

SEQUENCE LISTING DESCRIPTION

Figure 1:
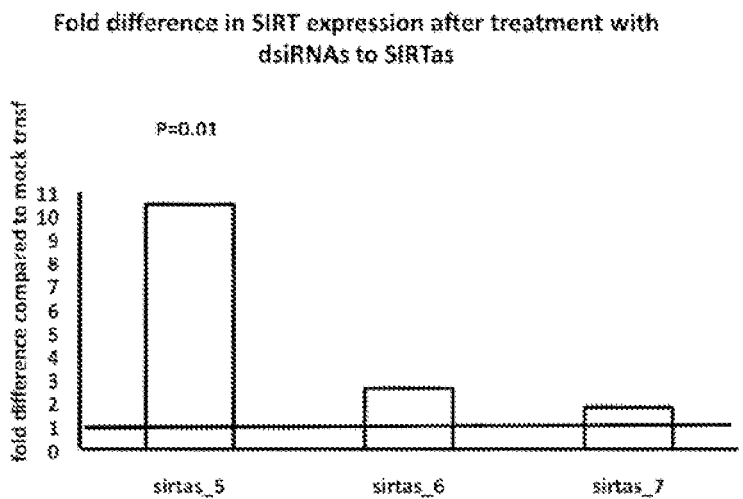
FIGS. 1 and 2 show Real time PCR results of experiments in which HepG2 cells were treated with oligonucleotides designed to target SIRT antisense CV396200. The results show that the levels of the SIRT1 mRNA in HepG2 cells were significantly increased 48 h after treatment with one of the siRNAs designed to sirtas (sirtas_5, P=0.01). In the same samples the levels of sirtas RNA were significantly decreased after treatment with sirtas_5, but unchanged after treatment with sirtas_6 and sirtas_7, which also had no effect on the SIRT1 mRNA levels (FIG. 2). sirtas_5, sirtas_6 and sirtas_7 correspond to SEQ ID NOs: 47, 48 and 49 respectively.

SEQ ID NO: 1: *Homo sapiens* sirtuin (silent mating type information regulation 2 homolog) 1 (*S. cerevisiae*) (SIRT1), mRNA (NCBI Accession Number: NM_012238.4)

SEQ ID NO: 133: *Homo sapiens* sirtuin 1 (SIRT1), transcript variant 2, mRNA (NCBI Accession Number: NM_001142498.1)

SEQ ID NO: 2: *Mus musoulus* sirtuin 1 (silent mating type information regulation 2, homolog) 1 (*S. cerevisiae*) (SIRT1) mRNA (NCBI Accession Number: NM_001159589)

SEQ ID NO: 3: *Homo sapiens* sirtuin 2 (SIRT2), transcript variant 1, mRNA (NCBI Accession No.: NM_012237.3).

SEQ ID NO: 134: *Homo sapiens* sirtuin 2 (SIRT2), transcript variant 2, mRNA (NCBI Accession Number: NM_030593.2)

SEQ ID NO: 135: *Homo sapiens* sirtuin 2 (SIRT2), transcript variant 3, mRNA (NCBI Accession Number: NM_001193286.1)

SEQ ID NO: 136: *Homo sapiens* sirtuin 2 (SIRT2), transcript variant 4, non-coding RNA (NCBI Accession Number: NR_034146.1)

SEQ ID NO: 4: *Homo sapiens* sirtuin (silent mating type information regulation 2 homolog) 3 (*S. cerevisiae*) (SIRT3). transcript variant 1, mRNA (NCBI Accession No.: NM_012239.5).

SEQ ID NO: 137: *Homo sapiens* sirtuin 3 (SIRT3), transcript variant 2, mRNA (NCBI Accession Number: NM_001017524.2)

SEQ ID NO: 5: *Homo sapiens* sirtuin 4 (SIRT4), mRNA (NCBI Accession No.: NM_012240).

SEQ ID NO: 138: *Homo sapiens* sirtuin 5 (SIRT5), transcript variant 2, mRNA (NCBI Accession Number: NM_031244.2)

SEQ ID NO: 139: *Homo sapiens* sirtuin 5 (SIRT5), transcript variant 3, mRNA (NCBI Accession Number: NM_001193267.1)

SEQ ID NO: 6: *Homo sapiens* sirtuin 5 (SIRT5), transcript variant 1, mRNA (NCBI Accession No.: NM_012241).

SEQ ID NO: 7: *Homo sapiens* sirtuin 6 (SIRT6), transcript variant 1, mRNA (NCBI Accession No.: NM_016539).

SEQ ID NO: 140: *Homo sapiens* sirtuin 6 (SIRT6), transcript variant 2, mRNA (NCBI Accession Number: NM_001193285.1)

SEQ ID NO: 8: *Homo sapiens* sirtuin 7 (SIRT7), mRNA (NCBI Accession No.: NM_016538). *Natural Antisense Sequences*-SEQ ID NO: 9: Expanded natural antisense sequence (CV396200-expanded); SEQ ID NO: 10: Natural Antisense sequence (CV428275); SEQ ID NO: 11: Natural Antisense Sequence (BE717453) SEQ ID NO: 12: Natural Antisense Sequence (AV718812); SEQ ID NO: 13: Natural SIRT1 antisense sequence (AW169958): SEQ ID NO: 14: Mouse Natural SIRT1 mouse antisense sequence (AK044604); SEQ ID NO: 15: Natural SIRT3 antisense sequence (Hs.683117); SEQ ID NO: 16: Natural SIRT3 antisense sequence (DA645474) SEQ ID NO: 17: Natural SIRT3 antisense sequence (BQ024738); SEQ ID NO: 18: Natural SIRT3 antisense sequence (BE164357); Natural SIRT3 antisense sequence (RIC8A) SEQ ID NO: 141, Natural SIRT3 antisense sequence (PMSD13) SEQ ID NO: 142, Natural SIRT3 antisense sequence (DA246502) SEQ ID NO: 143, SEQ ID NO: 19: Natural SIRT4 antisense sequence (AA156947); SEQ ID NO: 20: Natural SIRT5 antisense sequence (Hs.671550); SEQ ID NO: 21: Natural SIRT6 antisense sequence (BF772662); SEQ ID NO: 22: Natural SIRT6 antisense sequence (ANKRD24); SEQ ID NO: 23; Natural SIRT7 antisense sequence (Hs.671550) *Antisense oligonucleotides*-SEQ ID NOs: 24 to 127.* indicates phosphothioate bond, + indicates LNA and m indicates 2'O Me, r indicates RNA SEQ ID NO: 128 to 130-SEQ ID NO: 128 correspond to the exon 4 of the SIRT1 natural antisense CV396200, SEQ ID NO: 129, 130 and 131 correspond to the forward primer sequence, reverse primer sequence and the reporter sequence respectively. SEQ ID NO: 132 corresponds to CUR 962, * indicates phosphothioate bond and + indicates LNA.

SEQ ID NO: 144 and 145 correspond to reverse complement of the antisense oligonucleotide SEQ ID NOS: 126 and 127 respectively.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In embodiments, the genes or nucleic acid sequences are human.

The accession numbers named herein identify publicly available sequences in the National Institutes of Health database, GenBank (see Nucleic Acids Research, 2008 Jan. 36 Database issue: D25-30), unless otherwise indicated. All sequences referenced by accession number are incorporated herein by reference.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise slated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register" that is, when the monomers are linked consecutively, as in native DNA, or linked via spacers. The spacers are intended to constitute a covalent "bridge" between the regions and have in cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "Sirtuins (SIRT)s" are inclusive of all family members, mutants, alleles, fragments, species, coding and noncooding sequences, sense and antisense polynucleotide strands, etc.

As used herein, the words Sirtuin 1, SIRT1, sirtuin, silent mating type information regulation 2 homolog 1, hSIR2, hSIRT1, NAD-dependent deacetylase sirtuin-1, SIR2L1, SIR2-like protein 1, are considered the same in the literature and are used interchangeably in the present application.

As used herein, the words Sirtuin2, Sirtuin-2, SIRT2, SIR2L and SIR2L2, are considered same in the literature and used interchangeably in the present application.

As used herein, the words 'Sirtuin 3', Sirtuin3, Sirtuin-3, SIRT3, SIRT-3, hSIRT3, NAD-dependent deacetylase sirtuin-3, mitochondrial, SIR2L3, SIR2-like protein 3 are used interchangeably in the present application.

As used herein, the words Sirtuin4, SIRT4, MGC130046, MGC130047, MGC57437, NAD-dependent ADP-ribosyl-transferase sirtuin-4, SIR2L4, SIR2-like protein 4, are considered same in the literature and used interchangeably in the present application.

As used herein, the words Sirtuin 5, SIRT5, FLJ36950, NAD-dependent deacetylase sirtuin-5, SIR2L5, SIR2-like protein 5, are considered same in the literature and used interchangeably in the present application.

As used herein, the words 'Sirtuin 6', Sirtuin6, Sirtuin-6, SIRT6, SIRT-6, NAD-dependent deacetylase sirtuin-6, SIR2L6, SIR2-like protein 6 are considered the same in the literature and are used interchangeably in the present application.

As used herein, the words Sirtuin 7, SIRT7, MGC126840, MGC126842, NAD-dependent deacetylase sirtuin-7, SIR2L7, SIR2-like protein 7, are considered same in the literature and used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs that can be used in accordance with the present invention cast be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" meant an RNA molecule with enzymatic activity. Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphomates, phosphoroselenoate, phosphoramidate, and the like, as more fully described below.

The term "nucleotide" covers naturally incurring nucleotides as well as non-naturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo- N6-methyladenine, 7-deazaxanthine, 7-deazaguanine, N4,N4-ethanocytosin, N6,N6-ethano-2,6-diaminopurine, 5-methylcytosine, 5-(C3-C6)- alkynylcytosine, 5-flourouracil, 5-bromouracil, pseudoisocytosine, 2-hydroxy-5-methyl-4-triazolopyridin, isocytosine, isoguanin, inosine and the "non-naturally occurring" nucleotides described in U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties. Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15 M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound tire complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complemenlarity, can be determined by, for example, the Gap program.

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g. derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radio-isotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc).

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Additional cancers which can be treated by the disclosed composition according to the invention include but not limited to, for example. Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Neurological disease or disorder" refers to any disease or disorder of the nervous system and/or visual system, "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuroopthalmology, movement disorders, demyelinatiag diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Toot disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy Walker syndrome; Dawson disease; De Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; fisher syndrome; Friedreich's ataxia; fronto-temporal dementia and other "tauopathies"; Gaucher's disease; Gerstmann's syndrome; giant cell arteritis; giant cell inclusion disease; globoid cell leukodystrophy; Guillain-Barre syndrome; HTLV-1-associated myelopathy; Hallervorden-Spate disease; head injury; headache; hemifacial spasm; hereditary spastic paraplegia; heredopathia atactic a polyneoritiformis; herpes zoster oticus; herpes zoster; Hirayama syndrome; HIV associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigment; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lissencephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; posterpetic neuralgia; postinfectious encephalomyelitis; postural hypotension; Prader-Willi syndrome; primary lateral sclerosis; prion diseases; progressive hemifacial atrophy; progressive multifocallcukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic, encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

"Metabolic disease" refers to a wide range of diseases and disorders of the endocrine system including, for example, insulin resistance, diabetes, obesity, impaired glucose tolerance, high blood cholesterol, hyperglycemia, dyslipidemia and hyperlipidemia.

An "Inflammation" refers to systemic inflammatory conditions and conditions associated locally with migration and attraction of monocytes, leukocytes and/or neutrophils. Examples of inflammation include, but are not limited to, Inflammation resulting from infection with pathogenic organisms (including grant-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in aterosclerotic plaques. Inflammation includes, but is not limited to, Non-Hodgkin's lymphoma, Wegener's granulomatosis, Hashimoto's thyroiditis, hepatocellular carcinoma, thymus atrophy, chronic pancreatitis, rheumatoid arthritis, reactive lymphoid hyperplasia, osteoarthritis, ulcerative colitis, papillary carcinoma, Crohn's disease, ulcerative colitis, acute cholecystitis, chronic cholecystitis, cirrhosis, chronic sialadenitis, peritonitis, acute pancreatitis, chronic pancreatitis, chronic Gastritis, adenomyosis, endometriosis, acute cervicitis, chronic cervicitis, lymphoid hyperplasia, multiple sclerosis, hypertrophy secondary to idiopathic thrombocytopenic purpura, primary IgA nephropathy, systemic lupus erythematosus, psoriasis, pulmonary emphysema, chronic pyelonephritis, and chronic cystitis.

A 'cardiovascular disease or disorder' includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to Sirtuin3 activation. CVS diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

Polynucleotide and Oligonucleotide Compositions and Molecules

Targets

In one embodiment, the targets comprise nucleic acid sequences of a Sirtuin (SIRT), including without limitation sense and/or antisense noncoding and/or coding sequences associated with a Sirtuin (SIRT).

In one embodiment, the targets comprise nucleic acid sequences of SIRT1, including without limitation sense and/or antisense noncoding and/or coding sequences associated with SIRT1 gene.

In one embodiment, the targets comprise nucleic acid sequences of SIRT2, including without limitation sense and/or antisense noncoding and/or coding sequences associated with SIRT2 gene.

In one embodiment, she targets comprise nucleic acid sequences of SIRT3, including without limitation sense and/or antisense noncoding and/or coding sequences associated with SIRT3 gene.

In one embodiment, the targets comprise nucleic acid sequences of SIRT4, including without limitation sense and/or antisense noncoding and/or coding sequences associated with SIRT4 gene.

In one embodiment, the targets comprise nucleic acid sequences of SIRT5, including without limitation sense and/or antisense noncoding and/or coding sequences associated with SIRT5 gene.

In one embodiment, the targets comprise nucleic acid sequences of SIRT6, including without limitation sense and/or antisense noncoding and/or coding sequences associated with SIRT6 gene.

In one embodiment, the targets comprise nucleic acid sequences of SIRT7, including without limitation sense and/or antisense noncoding and/or coding sequences associated with SIRT7 gene.

"SIRT1 protein" refers to a member of the sir2 family of sirtuin deacetylases. In one embodiment, a SIRT1 protein includes yeast Sir2 (GenBank Accession No. P53685), C. elegans Sir-2,1 (GenBank Accession No. NP.sub.-501912), human SIRT1. (GenBank Accession No. NM.sub.-012238 and NP,snb.-036370 (or AF083106))

SIRT1 "Sirtuins" are proteins that include a SIR2 domain, a domain defined as amino acids sequences that are scored as hits in the Plant family "SIR2"-PF02146 (attached to the Appendix). This family is referenced in the INTERPRO database as INTERPRO description (entry IPR003000). To identify the presence of a "SIR2" domain in a protein sequence, and make the determination that a polypeptide or protein of interest has a particular profile, the amino acid sequence of the protein can be searched against the Pfam database of HMMs (e.g., the Pfam database, release 9) using the default parameters (http://www.sanger.ac.uk/Software/Pfam/HMM_search). The SIR2 domain is indexed in Pfam as PF02146 and in INTERPRO as INTERPRO description (entry IPR003000). A description of the Pfam database can be found in "The Pfam Protein Families Database" Bateman A et al. (2002) Nucleic Acids Research 30(1):276-280 and Sonhammer et al. (1997) Proteins 28(3):405-420 and a detailed description of HMMs can be found, for example, in Gribskov et al. (1990) Meth. Enzymol. 183:146-159; Gribskov et al. (1987) Proc. Natl. Acad. Sci. USA 84:4355-4358; Krogh et al. (1994) J. Mol. Biol. 235:1501-1531; and Stultz et al. (1993) Protein Sci. 2:305-314.

Among the mitochondrial sirtuins, SIRT3 possesses the most robust deacetylase activity. Indeed, significantly higher levels of mitochondrial protein acetylation were detected in the livers of SIRT3-null mice, compared to those of SIRT4 or SIRT5 knockout animals. However, little is known about the physiological role of SIRT3 despite the fact that a number of SIRT3 substrates and co-precipitating proteins have been identified: acetyl-CoA synthetase 2, Ku70, FOXO3a, subunit 9 of mitochondrial Complex I (NDUFA9), glutamate dehydrogenase and isocitrate dehydrogenase 2.

SIRT3 is a major mitochondrial deacetylase. Mitochondrial proteins show hyperacetylation in SIRT3 knockout mice, but not in SIRT4 or SIRT5 knockout mice. Acetyl-CoA synthetase 2 (AceCS2), a mitochondrial enzyme that converts acetate into acetyl-CoA, was the first mitochondrial substrate of SIRT3 identified. Deacetylation of AccCS2 at lysine 642 by SIRT3 activates acetyl-CoA synthetase activity, providing increased acetyl-CoA to feed into the tricarboxylic acid cycle. Glutamate dehydrogenase (GDH), another mitochondrial protein involved in energy production, is deacetylated by SIRT3. GDH can also be ADP-ribosylated by SIRT4 in turn to decrease its enzyme activity. This indicates that SIRT3 could play an important role in cell metabolism. SIRT3 has also been shown to be involved in selective apoptosis pathways and cell growth control SIRT3 and SIRT4, but not SIRT5, have been implicated in the NAD+ salvage pathway that regulates the NAD+ level relating to cell survival. In addition, variability in the hSIRT3 gene has been linked to human longevity.

The Silent Information Regulator-2 gene (Sir2) encodes an NAD-dependent histone deacetylase that links regulation of chromatin, genomic stability, and life span in S. cerevisae. By promoting chromatin silencing, Sir2 inhibits transcription at several genetic loci and represses recombination at ribosomal DNA (rDNA) repeats. Yeast with mutations in Sir2 have increased genomic instability in the context of rDNA recombination, which in turn shortens replicative life span—a marker of reproductive aging in this organism. Conversely, extracopies of Sir2 that suppress rDNA recombination increase replicative life span. These effects of Sir2 suggest paradigms in which genes that promote genome stabilization through chromatin modulation may be important contributors to regulation organismal life span, aging, and age-related pathology.

Consistent with a conserved role for Sir2 factors in life span regulation, increased activity of Sir2 proteins in the multicellular organisms C. elegans and D. melanogaster also increases life span. However, these Sir2 factors may operate through mechanisms that are independent of genome stabilization, and their physiologic molecular substrates are still unclear. In mammals, there are seven Sir2 family members, SIRT1-SIRT7. The SIRTs have been of great interest as candidate regulate of mammalian life span and aging-related processes. In this context, several mammalian SIRTs have functions that impact on aging-associated molecular pathways and disease. However, initial studies of mammalian SIRTs linked these enzymes to biochemical targets and cellular functions that are distinct from those of S. cerevisiae Sir2.

Sirtuins are homologues of the yeast transcriptional repressor Sir2p and are conserved from bacteria to humans. Human SIRT4 is localized to the mitochondria. SIRT4 is a matrix protein and becomes cleaved at amino acid 28 after import into mitochondria. Mass spectrometry analysis of proteins that coimmunoprecipitate with SIRT4 identified insulin degrading enzyme and the ADP/ATP carrier proteins, ANT2 and ANT3. SIRT4 exhibits no histone deacetylase activity but functions as an efficient ADP-ribosyltransferase on histones and bovine serum albumin. SIRT4 is expressed in islets of Langerhans and colocalizes with insulin-expressing β cells. Depletion of SIRT4 from insulin-producing INS-1E cells results in increased insulin secretion in response to glucose.

Sirtuin (silent mating type information regulation 2 homology) 5 (S. cerevisae), also known as SIRT5 is a protein which in humans in encoded by the SIRT5 gene and in other species by the Sirt5 gene. This gene encodes a member of the sirtuin family of proteins, homologs to the yeast Sir2 protein. Members of the sirtuin family are characterized by a sirtuin core domain and grouped into four classes. The functions of human sirtuins have not yet been determined; however, yeast sirtuin proteins are known to regulate epigenetic gene silencing and suppress recombination of rDNA. Studies suggest that the human sirtuins may function as intracellular regulatory proteins with mono-ADP-ribosyltransferase activity. The protein encoded by this gene is included in class III of the sirtuin family. Alternative splicing of this gene results in two transcript variants.

The generation of mice deficient for the mammalian SIRT6 gene revealed a potential role for SIRT6 in linking regulation of life span, chromatin, and genomic stability. In this context, SIRT6 deficiency in mice leads to dramatically shortened life span and acute degenerative phenotypes that overlap with pathologies of premature aging. Moreover, SIRT6 knockout mouse cells have genomic instability and DNA damage hypersensitivity. In biochemical fractionation assays, SIRT6 protein associates preferentially with a chromatin-enriched cellular fraction. Together, these observations suggested that SIRT6 might couple chromatin regulation with DNA repair. However, a physiologic role for SIRT6 in such a process has not yet been demonstrated.

Mammalian sirtuins (SIRT1-7), homologs of the yeast Sir2, have recently been proposed to be involved in the control of critical metabolic pathways as well as apoptosis, stress responses, DNA repair, cell cycle, genomic stability and gene expression. Sirtuins, also designated class III histone deacetylases, are protein deacetylases/ADP ribosyltransferases. These enzymes are highly conserved from prokaryotes to eukaryotes. They all share a conserved NAD-dependent catalytic core domain, and exhibit variable N-terminal and C-terminal extensions that contribute to their unique subcellular localization and may also regulate their catalytic activity. The subcellular distribution, substrate specificity and cellular function of sirtuins are quite diverse. SIRT2 is a predominantly cytoplasmic protein, SIRT3-5 are mitochondrial and SIRT7, -6 and -7 are localized in the nucleus. SIRT7, the most closely related to yeast Sir2 and the best characterized sirtuin, possesses a large number of substrates, including p53, Ku70, NF-κB and forkhead transcription factors, that regulate cellular oxidative and genotoxic stresses. SIRT6 is involved in important functions in preserving cells from genomic instability and progeroid phenotype. Moreover, SIRT6 is the only sirtuin to exhibit a robust auto-ADP-ribosyltransferase activity. SIRT7 is the only sirtuin localized in nucleoli. It was shown to exhibit no deacetylase or ADP-ribosyltansferase activity when tested on acetylated histones and various acetylated components of the RNA Pol I machinery. Concerning the nucleolar function of SIRT7, Ford et al. proposed that SIRT7 could be a positive regulator of rDNA transcription via its association with RNA Pol I. Its overexpression enhances rDNA transcription, whereas its inhibition reduces rDNA transcription. Interestingly, expression of SIRT7 is positively correlated with cell growth: SIRT7 is abundant in metabolically active tissues such as liver, spleen and tests. To date, there are no data concerning the cell cycle regulation of SIRT7 and its fate during mitosis when rDNA transcription is repressed.

In some embodiments, antisense oligonucleotides are used to prevent or treat diseases or disorders associated with Sirtuin (SIRT) family members. Exemplary Sirtuin (SIRT) mediated diseases and disorders which can be treated with cell/tissues regenerated from stem cells obtained using the antisense compounds comprise: a disease or disorder associated with abnormal function and/or expression of Sirtuin, cancer (e.g., breast cancer, colorectal cancer, CCL, CML, prostate cancer), a neurodegenerative disease or disorder (e.g., Alzheimer's Disease (AD), Huntington's disease, Parkinson's disease, Amyotrophic Lateral Sclerosis (ALS), Multiple Sclerosis, and disorders caused by polyglutamine aggregation), a beta-amyloid disease or disorder (e.g., a disorder characterized by .beta.-amyloid accumulation such as Alzheimer's disease), skeletal muscle disease (e.g., Duchene muscular dystrophy, skeletal muscle atrophy, Becker's dystrophy, or myotonic dystrophy); a metabolic disease or disorder (e.g., insulin resistance, diabetes, type 2 diabetes, obesity, impaired glucose tolerance, metabolic syndrome, adult-onset diabetes, diabetic nephropathy, hyperglycemia, diabetic nephropathy, Hypercholesterolemia, dyslipidemia hyperlipidemia and an age-related metabolic disease etc.), a disease or disorder associated with impaired insulin regulation, neuropathy (e.g., sensory neuropathy, autonomic neuropathy, motor neuropathy, retinopathy), a disease or disorder associated with a ketogenic condition, a disease or disorder associated with impaired energy homeostasis, a disease or disorder associated with impaired Acetyl-CoA synthetase 2 activity, a disease or disorder associated with metabolic homeostasis, a lipid metabolism disease or disorder, a disease or disorder associated with impaired thermogenesis, a disease or disorder associated with impaired regulation of cell division, a disease or disorder associated with mitochondrial dysfunction, neuropathy (e.g., sensory neuropathy, autonomic neuropathy, motor neuropathy, retinopathy), fibrosis, inflammatory cardiomyopathy, heart hypertrophy, Ichronic inflammation, atherosclerosis, arthritis, dementia, osteoporosis, and a cardiovascular disease or disorder, a hepatic disease or disorder (e.g., due to alcohol abuse or hepatitis, fatty liver disease etc.), age-related macular degeneration, bone disease (e.g., osteoporosis), a blood disease (e.g., a leukemia), bone resorption, age-related macular degeneration, AIDS related dementia, ALS, Bell's Palsy, atherosclerosis, a cardiac disease or disorder (e.g., cardiac dysrhymias, chronic congestive heart failure, ischemic stroke, coronary artery disease and cardiomyopathy), chronically degenerative disease (e.g., cardiac muscle disease), chronic renal failure, type 2 diabetes, ulceration, cataract, presbiopia, glomerulonephritis, Guillan-Barre syndrome, hemorrhagic stroke, rheumatoid arthritis, inflammatory bowel disease, SLE, Crohn's disease, osteoarthritis, osteoporosis. Chronic Obstructive Pulmonary Disease (COPD), pneumonia, skin aging, a skin disease or disorder, urinary incontinence, a disease or disorder associated with mitochondrial dysfunction (e.g., mitochondrial myopathy, encephalopathy, Leber's disease, Leigh encephalopathia, Pearson's disease, lactic acidosis, 'mitochondrial encephalopathy, lactic acidosis and stroke like symptoms' (MELAS) etc.), liver degeneration, skeletal muscle degeneration, a muscular disease or disorder, inflammation, a disease or disorder associated with ectopic lipid storage, a disease or disorder associated with oxidative stress, a disease or disorder associated with cellular stress, a disease or disorder associated with neuronal cell death, aging or other condition characterized by unwanted cell loss, degenerative syndrome, a disease or disorder associated with ammonia detoxification, aging, a disease or disorder associated with telomere dysfunction, a disease or disorder associated with impaired chromatin regulation, a disease or disorder associated with premature cellular senescence, a disease or disorder associated with impared SIRT mediated DNA repair and a condition characterized by unwanted cell loss.

Sirtuins have been reported to regulate TNF-alpha activity, as described in, e.g., U.S. Pat. App. Pub. No. 2010/0137345, "Prophylactic and therapeutic use of sirtuin inhibitors in TNF-alpha mediated pathologies," incorporated herein by reference in its entirety. In embodiments antisense oligonucleotides of the present invention are used to modulate Sirtuins, e.g., SIRT 6, to treat TNP-alpha-mediated disorders or diseases. TNF-alpha-mediated disorders or diseases include, e.g., ankylosing spondylitis, atherosclerosis, inflammatory bowel disease (IBD) including Crohn's disease and ulcerative colitis, psoriasis, psoriatic arthritis, or rheumatoid arthritis, cachexia, Gram-negative sepsis, endotoxin-induced shock, septic shock syndrome, systemic inflammatory response syndrome (SIRS) or multiple organ dysfunction syndrome (MODS); and/or graft versus host pathologies, including graft versus host disease (GVHD) and rejection of transplanted xenogenic or allogeneic tissues or organs; and/or acute or chronic infectious or parasitic processes, including viral, bacterial or fungal, infections and protozoan or metazoan parasite infections, preferably cerebral malaria or meningococcal meningitis; and/or allergic disorders, including allergic rhinitis, allergic conjunctivitis, asthma, eczema, urticaria, contact dermatitis, systemic allergic response (anaphylaxis) and anaphylactic shock, allergic rhinitis or asthma, acute disseminated encephalomyelitis (ADEM); Addison's disease; ankylosing spondylitis; antiphospholipid antibody syndrome (APS); aplastic anemia; atherosclerosis; autoimmune gastritis; autoimmune hepatitis; autoimmune thrombocytopenia; Behcet's disease; coeliac disease; dermatomyositis; diabetes mellitus type I; diabetes mellitus type II; familial Mediterranean fever; familial cold-induced autoinflammatory syndrome; Goodpasture's syndrome; gout; pseudogout; Graves' disease; Guillain-Barre syndrome (GBS); Hashimoto's disease; hereditary periodic fevers; idiopathic thrombocytopenic purpura; inflammatory bowel disease (IBD) including Crohn's disease and ulcerative colitis; ischemia-reperfusion injury; Kawasaki's disease; mixed connective tissue disease; Muckle-Wells syndrome; multiple sclerosis (MS); myasthenia gravis; opsoclonus myoclonus syndrome (OMS); optic neuritis; Ord's thyroiditis; osteoarthritis; pemphigus; pernicious anaemia; polyarteritis nodosa; polymyositis; postoperative or traumatic inflammation; primary biliary cirrhosis; primary myoxedema; psoriasis; psoriatic arthritis; rheumatic fever; rheumatoid arthritis; Reiter's syndrome; scleroderma; Sjogren's syndrome; stroke-ischemia; systemic lupus erythematosus (SLE); systemic onset juvenile idiopathic arthritis; Takayasu's arteritis; temporal arteritis; vitiligo; warm autoimmune hemolytic anemia; and Wegener's granulomatosis.

In another embodiment, the antisense oligonucleotides modulate the normal expression and/or normal function of a Sirtuin (SIRT) in patients suffering from or at risk of developing diseases or disorders associated with Sirtuin (SIRT).

In embodiments of the present invention, therapeutic and/or cosmetic regimes and related tailored treatments are provided to subjects requiring skin treatments or at risk of developing conditions for which they would require skin treatments. Diagnosis can be made, e.g., based on the subject's SIRT status. A patient's SIRT expression levels in a given tissue such as skin can be determined by methods known to those of skill in the art and described elsewhere herein, e.g., by analyzing tissue using PCR or antibody-based detection methods.

A preferred embodiment of the present invention provides a composition for skin treatment and/or a cosmetic application comprising SIRT antisense oligonucleotides, e.g., to upregulate expression of SIRT in the skin. Examples of antisense oligonucleotides are set forth as SEQ ID NOS: 24 to 127. U.S. Pat. No. 7,544,497, "Compositions for manipulating the lifespan and stress response of cells and organisms," incorporated herein by reference, describes potential cosmetic use for agents that modulate Sirtuin activity by reducing the $K_m$ of the Sirtuin protein for its substrate. In embodiments, cells are treated in vivo with the oligonucleotides of the present invention, to increase cell lifespan or prevent apoptosis. For example, skin can be protected from aging, e.g., developing wrinkles, by treating skin, e.g., epithelial cells, as described herein. In an exemplary embodiment, skin is contacted with a pharmaceutical or cosmetic composition comprising a SIRT antisense compound as described herein. Exemplary skin afflictions or skin conditions include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, skin cancer and the effects of natural aging.

Sirtuin has been reported to interfere with dihydrotestosterone-induced androgen receptor signaling. (See, e.g., Fu, et al., 2006, "Hormonal Control of Androgen Receptor Function through SIRT1," Molecular and Cellular Biology 26(21): 8122-8135, incorporated herein by reference.) In embodiments of the present invention, a composition comprising SIRT antisense oligonucleotides, e.g., to upregulate expression of SIRT in the scalp and inhibit androgen receptor signaling, thereby preventing androgenetic alopecia (hair loss). In embodiments, a patient suffering from alopecia is administered either a topical or systemic formulation. In an embodiment, an antisense oligonucleotide described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Formulations may be colorless, odorless ointments, lotions, creams, microemulsions and gels.

Antisense oligonucleotides of the invention may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well e.g., emolliency or the like. As with other carriers or vehicles, an ointment base should be inert, stable, nonirritating and nonsensitizing. As explained in Remington's Pharmaceutical Sciences (Mack Pub. Co.), ointment bases may be grouped into four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight (see, e.g., Remington's, supra).

Antisense oligonucleotides of the invention may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the case of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor® from Beiersdorf, Inc. (Norwalk, Conn.).

Antisense oligonucleotides of the invention may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation as explained in Remington's, supra, is generally a nonionic, anionic, cationic or amphoteric surfactant.

Antisense oligonucleotides of the invention may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono and di-esters of PEG (e.g., oleoyl macrogol glycerides), etc.

Antisense oligonucleotides of the invention may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents, include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. % solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide (C.sub.10 MSO) and tetradecylmethyl sulfboxide; pyrrolidones such as 2-pyrrolidone, N-methyl-2-pyrrolidone and N-(-hydroxyethyl)pyrrolidone; urea; N,N-diethyl-m-toluamide; C.sub.2-C.sub.6 alkanediols; miscellaneous solvents such as dimethyl formamide (DMF), N,N-dimethylactamide (DNA) and tetrahydrofurfuryl alcohol; and the 1-substituted azacycloheptan-2-ones, particularly 1-n-dodecylcyclazacycloheptan-2-one (laurocapram; available under the trademark Azone® from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol®) and diethylene glycol monoethyl ether oleate (available commercially as Soficutol®); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol®); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In one embodiment, the oligonucleotides are specific for polynucleotides of a Sirtuin (SIRT), which includes, without limitation noncoding regions. The Sirtuin (SIRT) targets comprise variants of a Sirtuin (SIRT); mutants of a Sirtuin (SIRT), including SNPs; noncoding sequences of a Sirtuin (SIRT); alleles, fragments and the like. Preferably the oligonucleotide is an antisense RNA molecule.

In accordance with embodiments of the invention, the target nucleic acid molecule is not limited to Sirtuin (SIRT) polynucleotides alone but extends to any of the isoforms, receptors, homologs, non-coding regions and the like of a Sirtuin (SIRT).

In another embodiment, an oligonucleotide targets a natural antisense sequence (natural antisense to the coding and non-coding regions) of a Sirtuin (SIRT) targets, including, without limitation, variants, alleles, homology mutants, derivatives, fragments and complementary sequences thereto. Preferably the oligonucleotide is an antisense RNA or DNA molecule.

In another embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another embodiment, targeting of a Sirtuin (SIRT) including without limitation, antisense sequences which are identified and expanded, using for example, PCR, hybridization etc., one or more of the sequences set forth as SEQ ID NO: 9 to 23, 141 to 143, and the like, modulate the expression or function of a Sirtuin (SIRT). in one embodiment, expression or function is up-regulated as compared to a control. In another embodiment, expression or function is down-regulated as compared to a control.

In another embodiment, oligonucleotides comprise nucleic acid sequences set forth, as SEQ ID NOS: 24 to 127 including antisense sequences which are identified and expanded, using for example, PCR, hybridization, etc. These oligonucleotides can comprise one or more modified nucleotides, shorter or longer fragments, modified bonds and the like. Examples of modified bonds or internucleotide linkages comprise phosphorothioate, phosphorodithioate or the like. In another embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be unregulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes a Sirtuin (SIRT).

The targeting process usually also includes determination of at least one target region, segment, or site within the target nucleic acid for the antisense interaction, to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In one embodiment, the antisense oligonucleotides bind to the natural antisense sequences of a Sirtuin (SIRT) and modulate the expression and/or function of a Sirtuin (SIRT) (SEQ ID NO: 1 to 23 and 133 to 143). Examples of antisense sequences include SEQ ID NOS: 24 to 127.

In another embodiment, the antisense oligonucleotides bind to one or more segments of a Sirtuin (SIRT) polynucleotide and modulate the expression and/or function of a Sirtuin (SIRT). The segments comprise at least five consecutive nucleotides of a Sirtuin (SIRT) sense or antisense polynucleotides.

In another embodiment, the antisense oligonucleotides are specific for natural antisense sequences of a Sirtuin (SIRT) wherein binding of the oligonucleotides to the natural antisense sequences of a Sirtuin (SIRT) modulate expression and/or function of a Sirtuin (SIRT).

In another embodiment, oligonucleotide compounds comprise sequences set forth as SEQ ID NOS: 24 to 127, antisense sequences which are identified and expanded, using for example, PCR, hybridization, etc. These oligonucleotides can comprise one or more modified nucleotides, shorter or longer fragments, modified bonds and the like. Examples of modified bonds or internucleotide linkages comprise phosphorothioate, phosphorodithioate or the like. In another embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a Sirtuin (SIRT), regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Other target regions of SIRT1 comprise nucleotides 65 to 85, and 221 to 253 of the antisense transcript CV396200. In embodiments, methods of modulating a function of and/or expression of a SIRT1 polynucleotide comprise contacting cells or tissues with at least one antisense oligonucleotide that targets one or more of these regions, in part or in whole. In certain embodiments, a combination of antisense oligonucleotides that target one or more of these regions, and one or more antisense transcripts that target other Sirtuins, are used. In embodiments, multiple antisense oligonucleotides targeting different regions of a SIRT are used in combination, or multiple antisense oligonucleotides targeting one or more different Sirtuins are administered in combination.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more)

mRNAs from different gene sources are known as "fusion transcripts". Introns can be effectively targeted using antisense compounds targeted to, for example, DNA or pre-mRNA.

In another embodiment, the antisense oligonucleotides bind to coding and/or non-coding regions of a target polynucleotide and modulate the expression and/or function of the target molecule.

In another embodiment, the antisense oligonucleotides bind to natural antisense polynucleotides and modulate the expression and/or function of the target molecule.

In another embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure.

Target segments 5-100 nucleotides in length comprising a stretch of at least five (5) consecutive nucleotides selected from within the illustrative target segments are considered to be suitable for targeting as well.

Target segments can include DNA or RNA sequences that comprise at least the 5 consecutive nucleotides from the 5'-terminus of one of the illustrative target segments (the remaining nucleotides being a consecutive stretch of she same DNA or RNA beginning immediately upstream of the 5'-terminus of the target segment and continuing until the DNA or RNA contains about 5 to about 100 nucleotides). Similarly target segments are represented by DNA or RNA sequences that comprise at least the 5 consecutive nucleotides from the 3'-terminus of one of the illustrative target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, specific nucleic acids are targeted by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (mRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polyadenylated. Most researchers have for obvious reasons focused on polyadenylated mRNAs that are processed and exported to the cytoplasm. Recently, it was shown that the set of non-polyadenylated nuclear RNAs may be very large, and that many such transcripts arise from intergenic regions. The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If for example, at antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two stands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAs); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs).

Small double-stranded RNA (dsRNA), such as small interfering RNA (siRNA) and microRNA (miRNA) have been found to be the trigger of an evolutionary conserved mechanism known as RNA interference (RNAi), RNAi invariably leads to gene silencing. However, in instances described in detail in the examples section which follows, oligonucleotides are shown to increase the expression and/or function of the Sirtuin (SIRT) polynucleotides and encoded products thereof. dsRNAs may also act as small activating RNAs (saRNA). Without wishing to be bound by theory, by targeting sequences in gene promoters, saRNAs would induce target gene expression in a phenomenon referred to as dsRNA-induced transcriptional activation (RNAa).

In a further embodiment, the "target segments" identified herein may be employed in a screen for additional compounds that modulate the expression of a Sirtuin (SIRT) polynucleotide. "Modulators" are those compounds that decrease or increase the expression of a nucleic acid molecule encoding a Sirtuin (SIRT) and which comprise at least a 5-nucleotide portion that is complementary to a target segment. The screening method comprises the steps of contacting a target segment of a nucleic acid molecule encoding sense or natural antisense polynucleotides of a Sirtuin (SIRT) with one or more candidate modulators, and selecting for one or more candidate modulators which decrease or increase the expression of a nucleic acid molecule encoding a Sirtuin (SIRT) polynucleotide, e.g. SEQ ID NOS: 24 to 127. Once it is shown that the candidate modulator or modulators are capable of modulating (e.g. either decreasing or increasing) the expression of a nucleic acid molecule encoding a Sirtuin (SIRT) polynucleotide, the modulator may then be employed in further investigative studies of the function of a Sirtuin (SIRT) polynucleotide, or for use as a research, diagnostic, or therapeutic agent in accordance with the present invention.

Targeting the natural antisense sequence modulates the function of the target gene. For example, the Sirtuin (SIRT) (e.g. accession numbers NM_12238.4, NM_001159589, NM_012237.3, NM_012239, NM_012240, NM_012241, NM_016539, NM_016538, NM_101142498.1, NM_030593.2, NM_001193286.1, NR_034146.1, NM_001017524.2, NM_031244.2, NM_001193267.1, NM_001193285.1). In an embodiment, the target, is an antisense polynucleotide of the Sirtuin (SIRT). In an embodiment, an antisense oligonucleotide targets sense and/or natural antisense sequences of a Sirtuin (SIRT) polynucleotide (e.g. accession numbers NM_012238.4, NM_001159589. NM_012237.3, NM_012239, NM_012240, NM_012241, NM_016539, NM_016538, NM_001142498.1, NM_030593.2, NM_00193286.1, NR_034146.1, NM_001017524.2, NM_031244.2, NM_001193267.1, NM_001193285.1), variants, alleles, isoforms, homologs, mutants, derivatives, fragments and complementary sequences thereto. Preferably the oligonucleotide is an antisense molecule and the targets include coding and noncoding regions of antisense and/or sense Sirtuin (SIRT) polynucleotides.

The target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example, such doable-stranded moieties have been shown to inhibit the target by the classical hybridization of antisense strand of the duplex to the target, thereby triggering enzymatic degradation of the target.

In an embodiment, an antisense oligonucleotide targets Sirtuin (SIRT) polynucleotides (e.g. accession numbers NM_012238.4, NM_00159589, NM_012237.3, NM_012239, NM_012240, NM_012241, NM_016539, NM_016538, NM_001142498.1, NM_030593.2, NM_00193286.1, NR_034146.1, NM_001017524.2, NM_031244.2, NM_001193267.1, NM_001193285.1), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Sirtuin (SIRT) alone but extends to any of the isoforms, receptors, homologs and the like of a Sirtuin (SIRT) molecule.

In another embodiment, an oligonucleotide targets a natural antisense sequence of a Sirtuin (SIRT) polynucleotide, for example, polynucleotides set forth as SEQ ID NO: 9 to 23, 141 to 143, and any variants, alleles, homologs, mutants, derivatives, fragments and complementary sequences thereto. Examples of antisense oligonucleotides are set forth as SEQ ID NOS: 24 to 127.

In one embodiment, the oligonucleotides are complementary to or bind to nucleic acid sequences of a Sirtuin (SIRT) antisense, including without limitation noncoding sense and/or antisense sequences associated with a Sirtuin (SIRT) polynucleotide and modulate expression and/or function of a Sirtuin (SIRT) molecule.

In another embodiment, the oligonucleotides are complementary to or bind to nucleic acid sequences of a Sirtuin (SIRT) natural antisense, set forth as SEQ ID NO: 9 to 23, 141 to 143 and modulate expression and/or function of a Sirtuin (SIRT) molecule.

In an embodiment, oligonucleotides comprise sequences of at least 5 consecutive nucleotides of SEQ ID NOS: 24 to 127 and modulate expression and/or function of a Sirtuin (SIRT) molecule.

The polynucleotide targets comprise Sirtuin (SIRT), including family members thereof, variants of a Sirtuin (SIRT): mutants of a Sirtuin (SIRT), including SNPs: non-coding sequences of a Sirtuin (SIRT); alleles of a Sirtuin (SIRT); species variants, fragments and the like. Preferably the oligonucleotide is an antisense molecule.

In another embodiment, the oligonucleotide targeting Sirtuin (SIRT) polynucleotides, comprise: antisense RNA, interference RNA (RNAi), short interfering RNA (siRNA); micro interfering RNA (tmRNA); a small, temporal RNA (stRNA); or a short, hairpin RNA (shRNA); small RNA-induced gene activation (RNAa); or, small activating RNA (saRNA).

In another embodiment, targeting of a Sirtuin (SIRT) polynucleotide, e.g. SEQ ID NO: 9 to 23, 141 to 143 modulate the expression or function of these targets. In one embodiment, expression or function is up-regulated as compared to a control. In another embodiment, expression or function is down-regulated as compared to a control.

In another embodiment, antisense compounds comprise sequences set forth as SEQ ID NOS: 24 to 127. These oligonucleotides can comprise one or more modified nucleotides, shorter or longer fragments, modified bonds and the like.

In another embodiment, SEQ ID NOS: 24 to 127 comprise one or more LNA nucleotides.

The modulation of a desired target nucleic acid can be carried out in several ways known in the art, for example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript.

Because of their sequence-specificity, trans-cleaving enzymatic nucleic acid molecules show promise as therapeutic agents for human disease. Enzymatic nucleic acid molecules can be designed to cleave specific RNA targets within the background of cellular RNA. Such a cleavage event raiders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies have been used to evolve new nucleic acid catalysts capable of catalyzing a variety of reactions, such as cleavage and ligation of phosphodiester linkages and amide linkages.

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural, self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987. The RNA catalyst was recovered and reacted with multiple RNA molecules, demonstrating that it was truly catalytic.

Catalytic RNAs designed based on the "hammerhead" motif have been used to cleave specific target sequences by snaking appropriate base changes in the catalytic RNA to maintain necessary base pairing with the target sequences. This has allowed use of the catalytic RNA to cleave specific target sequences and indicates that catalytic RNAs designed according to the "hammerhead" model may possibly cleave specific substrate RNAs in vivo.

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In one embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises front 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34,35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another embodiment, the oligomeric compounds of the present invention also include variants in which a different base is present at one or more of the nucleotide positions in the compound. For example, if the first nucleotide is an adenosine, variants may be produced which contain thymidine, guauosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another embodiment, the antisense oligonucleotides, such as for example, nucleic acid molecules set forth in SEQ ID NOS: 24 to 127 comprise one or more substitutions or modifications. In one embodiment, the nucleotides are substituted with locked nucleic acids (LNA).

In another embodiment, the oligonucleotides target one or more regions of the nucleic acid molecules sense and/or antisense of coding and/or non-coding sequences associated with SIRT and the sequences set forth as SEQ ID NOS: 1 to 23 and 133 to 143. The oligonucleotides are also targeted to overlapping regions of SEQ ID NOS: 1 to 23 and 133 to 143.

Certain oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA/DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such, hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another embodiment, the region of the oligonucleotide which is modified comprises at least one nucleotide modified at the 2' position of the sugar, most preferably a 2'-O-alkyl, 2'-O-alkyl-O-alkyl or 2'-fluoro-modified nucleotide. In other embodiments, RNA modifications include 2'-fluoro, 2'-amino and 2' O-methyl modifications on the ribose of pyrimidines, abasic residues or an inverted base at the 3" end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA:DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another embodiment, the chimeric oligonucleotide is also modified to enhance nuclease resistance. Cells contain a variety of exo and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some eases, oligonucleotide modifications which enhance target binding affinity are also, independently, able to enhance nuclease resistance. Some desirable modifications can be found in De Mesmaeker et al. (1995) *Acc. Chem. Res.,* 28:366-374.

Specific examples of some oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most are oligonucleotides with phosphorothioate backbones and those with heteroatom backbones, particularly CH2—NH—O—CH2, CH, —N(CH3)—O—CH2 [known as a methylene(methylimino) or MMI backbone], CH2—O—N (CH3)—CH2, CH2—N (CH3)—N (CH3)—CH2 and O—N (CH3)—CH2—CH2 backbones, wherein the native phosphodiester backbone is represented as O—P—O—CH). The amide backbones disclosed by De Mesmaeker et al. (1995) Acc. Chem. Res. 28:366-374 are also preferred. Also are oligonucleotides having morpholino backbone structures (Summerton and Weller, U.S. Pat. No. 5,034,506). In other embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties, oligonucleotides comprise one of the following at the 2' position: OH, SH, SCH3, F, OCN, OCH3 OCH3 OCH3 (CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CM; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group: an intercalator; a group for improving the pharmacokinetic properties of an oligonucleotide; or a group for improving the pharmacodynamic properties of an oligonucleotide and other substituents having similar properties. A modification includes 2'-methoxyethoxy [2'-O—CH2 CH2 OCH3, also known as 2'-O-(2-methoxyethyl)]. Other modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytokine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me—C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymetyhluracil, 8-azaguanine, 7-deazaguanine, N6 (6-aminohexyl)adenine and 2,6-diaminopurine. A "universal" base known in the art, e.g., inosine, may be included. 5-Me—C substitutions have been shown to increase nucleic acid duplex stability by 0.6-1.2° C. (Sanghvi, Y, S., in Crooke, S. T. and Lebleu, B., eds., Antisense Research and Applications, CRC Press, Boca Raton, 1993, pp. 276-278) and are presently base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, a thioether, e.g., hexyl-S-trityithiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid. Oligonucleotides comprising lipophilic moieties, and methods for preparing such oligonucleotides are known in the art, for example, U.S. Pat. Nos. 5,138,045, 5,218,105 and 5,459, 255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc. This can be achieved by substituting some of the monomers in the current oligonucleotides by LNA monomers. The LNA modified oligonucleotide may have a size similar to the parent compound or may be larger or preferably smaller. It is that such LNA-modified oligonucleotides contain less than about 70%, more preferably less man about 60%, most preferably less man about 50% LNA monomers and that their sizes are between about 5 and 25 nucleotides, more preferably between about 12 and 20 nucleotides.

Modified oligonucleotide backbones comprise, but are not limited to, phosphorothioates, chiral phosphorothioates, phosphorodithioates, phosphotriesters, aminoalkylphosphotriesters, methyl, and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleotides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds comprise, bat are not limited to, U.S. Pat. Nos. 5,539,082; 5,714,331; and 5,719,262, each of which is herein incorporated by reference. Further teaching of PNA compounds can be found in Nielsen et al. (1991) Science 254, 1497-1500.

In another embodiment of the invention the oligonucleotides with phosphorothioate backbones and oligonucleosides wife heteroatom backbones, and in particular-CH2—NH—O—CH2—,—CH2—N (CH3)—O—CH2-known as a methylene (methylimino) or MMI backbone, —CH2—O—N (CH3)—CH2—,—CH2(CH3)—N(CH3) CH2-and-O—N(CH3)—CH2—CH2— wherein the native phosphodiester backbone is represented as-O—P—O—CH2— of the above referenced U.S. Pat. No. 5,489,677, and the amide backbones of the above referenced U.S. Pat. No. 5,602,240. Also are oligonucleotides having morpholino backbone structures of the above-referenced U.S. Pat. No. 5,034,506.

Modified oligonucleotides may also contain one or more substituted sugar moieties, oligonucleotides comprise one of the following at the 2' position: OH; F; O—, S—, or N-alkyl; O—, or N-alkenyl; O—, S— or N-alkynyl; or O alkyl-O-alkyl, wherein the alkyl, alkenyl and alkynyl may be substituted or unsubstituted C to CO alkyl or C2 to CO alkenyl and alkynyl. Particularly are O (CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other oligonucleotides comprise one of the following at the 2' position; C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocyloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A modification comprises 2'-methoxyethoxy (2'-O-CH2CH2OCH3, also known as 2'—O—(2-methoxyethyl) or 2'-MOE) i.e., an alkoxyalkoxy group. A further modification comprises 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'—O—CH2—O—CH2—N (CH2)2.

Other modifications comprise 2'-methoxy (2'—O CH3), 2'-aminopropoxy (2'—O CH2CH2CH2NH2) and 2'-fluoro (2'—F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (CO, and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Engisch et al., 'Angewandle Chemie, International Edition', 1991, 30, page 613, and those disclosed, by Sanghvi, Y. S., Chapter 15, 'Antisense Research and Applications', pages 289-302, Crooke, S. T. and. Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooks, S. T. and Lebleu. B., eds, 'Antisense Research and Applications', CRC Press, Boca Raton, 1993, pp. 276-278) and are presently base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-t oxycholesterol moiety.

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

Drug discovery: The compounds of the present invention can also be applied in the areas of drug discovery and target validation. The present invention comprehends the use of the compounds and target segments identified herein in drug discovery efforts to elucidate relationships that exist between a Sirtuin (SIRT) polynucleotide and a disease state, phenotype, or condition. These methods include detecting or modulating a Sirtuin (SIRT) polynucleotide comprising contacting a sample, tissue, cell, or organism with the compounds of the present invention, measuring the nucleic acid or protein level of a Sirtuin (SIRT) polynucleotide and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, flourometric methods (e.g. fluorescence spectroscopy, Fluorescence Activated Cell Sorting (FACS), fluorescence microscopy), antibiotic resistance determination.

SIRT1, SIRT3 and SIRT6 proteins and mRNA expression can be assayed using methods known to those of skill in the art and described elsewhere herein. For example, immunoassays such as the ELISA can be used to measure protein levels. Sirtuin (SIRT) antibodies for ELISAs are available commercially, e.g., from R&D Systems (Minneapolis, Minn.), Abcam, Cambridge, Mass.

In embodiments, SIRT1, SIRT3 and SIRT6 expression (e.g., mRNA or protein) in a sample (e.g., cells or tissues in vivo or in vitro) treated using an antisense oligonucleotide of the invention is evaluated by comparison with Sirtuin (SIRT) expression in a control sample. For example, expression of the protein or nucleic acid can be compared using methods known to those of skill in the art with that in a mock-treated or untreated simple. Alternatively, comparison with a sample treated with a control antisense oligonucleotide (e.g., one having an altered or different sequence) can be made depending on the information desired. In another embodiment, a difference in the expression of the Sirtuin (SIRT) protein or nucleic acid in a treated vs. an untreated sample can be compared with the difference in expression of a different nucleic acid (including any standard deemed appropriate by the researcher, e.g., a housekeeping gene) in a treated sample vs. an untreated sample, Observed differences can be expressed as desired, e.g., in the form of a ratio or fraction, for use in a comparison with control. In embodiments, the level of a Sirtuin (SIRT) mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of a Sirtuin (SIRT) mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Regents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or the entire complement of genes expressed within cells and tissues.

As used herein, the term "biological system" or "system" is defined as any organism, cell, cell culture or tissue that expresses, or is made competent to express products of the Sirtuin (SIRT). These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays. SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive clotting, differential display (DD), comparative genomic hybridization, FISH (fluorescent in situ hybridization) techniques and mass spectrometry methods.

The compounds of the invention are useful for research and diagnostics, because these compounds hybridize to nucleic acids encoding a Sirtuin (SIRT). For example, oligonucleotides that hybridize with such efficiency and under such conditions as disclosed herein as to be effective Sirtuin (SIRT) modulator are effective primers or probes under conditions favoring gene amplification or detection, respectively. These primers and probes are useful in methods requiring the specific detection of nucleic acid molecules encoding a Sirtuin (SIRT) and in the amplification of said nucleic acid molecules for detection or for use in further studies of a Sirtuin (SIRT). Hybridization of the antisense oligonucleotides, particularly the primers and probes, of the invention with a nucleic acid encoding a Sirtuin (SIRT) can be detected by means known in the art. Such means may include conjugation of an enzyme to the oligonucleotide, radiolabeling of the oligonucleotide, or any other suitable detection means. Kits using such detection means for detecting the level of a Sirtuin (SIRT) in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a Sirtuin (SIRT) polynucleotide is treated by administering antisense compounds in accordance with this invention. For example, in one non-limiting embodiment, the methods comprise the step of administering to the animal in need of treatment, a therapeutically effective amount of a Sirtuin (SIRT) modulator. The Sirtuin (SIRT) modulators of the present invention effectively modulate the activity of a Sirtuin (SIRT) or modulate the expression of a Sirtuin (SIRT) protein. In one embodiment, the activity or expression of a Sirtuin (SIRT) in an animal is inhibited by about 10% as compared to a control. Preferably, the activity or expression of a Sirtuin (SIRT) in an animal is inhibited by about 30%. More preferably, the activity or expression of a Sirtuin (SIRT) in an animal is inhibited by 50% or more. Thus, the oligomeric compounds modulate expression of a Sirtuin (SIRT) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%. or by 100% as compared to a control.

In one embodiment, the activity or expression of a Sirtuin (SIRT) and/or in an animal is increased by about 10% as compared to a control. Preferably, the activity or expression of a Sirtuin (SIRT) in an animal is increased by about 30%. More preferably, the activity or expression of a Sirtuin (SIRT) in an animal is increased by 50% or more. Thus, the oligomeric compounds modulate expression of a Sirtuin (SIRT) mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In embodiments, Sirtuin modulation is observed by measuring levels of Sirtuin mRNA, antisense RNA, protein, biomarkers for Sirtuins, or combinations thereof, in a biological sample. Sirtuin biomarkers include, e.g., MCP-1, BMP Receptor 1A, Smpd13a, CD14, ApoE, FAS, Transthyretin, FABP1, Acyl-CoA thioesterase 1, Acyl-CoA thioesterase 2, Aquaporin 4, Rrad, CXCL9, CCL8, Pppltr3g, ApoA-I, ApoA-II, and ApoB. Biomarkers for Sirtuin expression and their use in monitoring Sirtuin expression is described, e.g., in U.S. Pat. App. Pub. No. 2010/0215632, "Biomarkers of Sirtuin Activity and Methods of Use Thereof," incorporated herein by reference in its entirety.

Assays for Sirtuin activity include assays for acetyltansferase/deacetylase activity. Such assays have been described in the literature, e.g., in U.S. Pat. App. Pub. No. 2009/0221.020, "Mass Spectrometry Assays for Acetyltransferase/Deacetylase Activity," incorporated herein by reference in its entirety. Any assay for Sirtuin activity known to those of skill in the art is contemplated for use in measuring Sirtuin activity in conjunction with the methods of the present invention.

In certain embodiments, modulation of Sirtuin expression is identified by an increase in (upregulation of) or a decrease in (downregalation of) the Sirtuin mRNA copy number, mRNA concentration, or biomarker mRNA or protein expression or activity, of at least about 10%, at least about 15%, at least about 20%, at least about 25%, at least about 30%, at least about 40%, at least about 50%, at least about 60%, at least about 70%, at least about 75%, at least about 80%, at least about 90%, at least about 100%, at least about 125%, at least about 150%, at least about 200%, at least about 250%, at least about 300%, at least about 3500%, at least about 400%, at least about 450%, or at least about 500%, at least about 600%, at least about 700%, at least about 800%, at least about 900%, or at least about 1000%, in comparison to a control, e.g., an untreated or mock-treated sample. In embodiments, the Sirtuin mRNA copy number, mRNA concentration, or biomarker mRNA or protein expression or activity increases or decreases by about 10% to about 500%. In embodiments, the Sirtuin mRNA copy number, mRNA concentration, or biomarker mRNA or protein expression or activity increases or decreases by about 10% to about 50%, about 10% to about 100%, about 10% to about 150%, about 10% to about 200%, about 10% to about 250%, about 10% to about 300%, about 10% to about 350%, about 10% to about 400%, about 10% to about 450%, about 10% to about 500%, about 10% to about 600%, about 10% to about 700%, about 10% to about 800%, about 10% to about: 900%, about 10% to about 1000%, about 50% to about 100%, about 50% to about 150%, about 50% to about 200%, about 50% to about 250%, about 50% to about 300%, about 50% to about 350%, about 50% to about 400%, about 50% to about 450%, about 50% to about 500%, about 50% to about 600%, about 50% to about 700%, about 50% to about 800%, about 50% to about 900%, about 50% to about 1000%, about 100% to about 150%, about 100% to about 200%, about 100% to about 250%, about 100% to about 300%, about 100% to about 350%, about 100% to about 400%, about 100% to about 450%, about 100% to about 500%, about 100% to about 600%, about 100% to about 700%, about 100% to about 800%, about 100% to about 900%, about 100% to about 1000%, about 150% to about 200%, about 150% to about 250%, about 150% to about 300%, about 150% to about 350%, about 150% to about 400%, about 150% to about 450%, about 150% to about 500%, about 150% to about 600%, about 150% to about 700%, about 150% to about 800%, about 150% to about 900%, about 150% to about 1000%, about 200% to about 250%, about 200% to about 300%, about 200% to about 350%, about 200% to about 400%, about 200% to about 450%, about 200% to about 500%, about 200% to about 600%, about 200% to about 700%, about 200% to about 800%, about 200% to about 900%, or about 200% to about 1000%.

For example, the reduction of the expression of a Sirtuin (SIRT) may be measured in serum, blood, adipose tissue, liver or any other body fluid, tissue or organ of the animal. Preferably, the cells contained within said fluids, tissues or organs being analyzed contain a nucleic acid molecule encoding Sirtuin (SIRT) peptides and/or the Sirtuin (SIRT) protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates: Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typicalconjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941.

Formulations: The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a non-viral vector operably linked to the polynucleotide. Examples of such nonviral vectors include the oligonucleotide alone (e.g. any one or more of SEQ ID NOS: 24 to 127) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector, Adenovirus Vectors and Adeno-associated Virus Vectors).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adeno-viral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier" U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 µm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

Formulations for topical administration include those in which the oligonucleotides of the invention are in admixture with a topical delivery agent such as lipids, liposomes, fatty acids, fatty acid esters, steroids, chelating agents and surfactants. Lipids and liposomes include neutral (e.g. diolcoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable, oral formulations are those in which oligonucleotides of the invention are administered in conjunction with one or more penetration enhancers surfactants and chelators. Surfactants include fatty acids and/or esters or salts thereof, bile acids and/or salts thereof, bile acids/salts and fatty acids and their uses are further described in U.S. Pat. No. 6,287,860, which is incorporated herein by reference. Also are combinations of penetration enhancers, for example, fatty acids/salts in combination with bile acids/salts. A particularly combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds in combination with one or more additional agents. The additional agents can function by a non-antisense mechanism. A second agent is, e.g., an agent currently used for treatment of the Sirtuin-associated disease or disorder. A second agent can alternatively be a non-Sirtuin modulating agent, e.g., a chemotherapeutic agent. For example, in the treatment of a cancer, one or more chemotherapeutic agents useful in treating the particular cancer can be administered in combination with at least one antisense oligonucleotide of the present invention. A combination treatment regimen encompasses treatment regimens in which administration of a SIRT antisense oligonucleotide is initiated prior to, during, or after treatment with a second agent, and continues until any time during treatment with the second agent or after termination of treatment with the second agent. It also includes treatments in which the agents being used in combination are administered simultaneously or at different times and/or at decreasing or increasing intervals during the treatment period. Combination treatment includes periodic treatments that start and stop at various times to assist with the clinical management of the patient. For example, an agent in the combination can be administered weekly at the onset of treatment, decreasing to biweekly, and decreasing further as appropriate.

Other Sirtuin-modulating agents that can be administered to a patient in combination with the antisense oligonucleotides of the present invention have been described in the literature, e.g., in U.S. Pat. App. Pub. No. 2000/0163476, "N-Phenyl Benzamide Derivatives as Sirtuin Modulators," incorporated herein by reference in its entirety. This publication reports the use of certain Sirtuin modulating compounds for treating neurodegenerative diseases, and traumatic or mechanical injury to the central nervous system (CNS), spinal cord or peripheral nervous system (PNS). It also lists additional therapeutic agents that can be used in combination with Sirtuin-modulating agents. Yet other Sirtuin-modulating agents contemplated for administration to patients in combination with the antisense oligonucleotides of the present invention are described in: U.S. Pat. No. 7,855,289 "Sirtuin modulating compounds" and; U.S. Pat. No. 7,829,556 "Sirtuin modulating compounds;" U.S. Pat. App. Pub. No. 2009/0143376, "Fused Heterocyclic Compounds and Their Use as Sirtuin Modulators;" U.S. Pat. App. Pub. No. 2009/0069301, Acridine and Quinoline Derivatives as Sirtuin Modulators;" U.S. Pat. App. Pub. No. 2007/0037865, "Sirtuin modulating compounds;" U.S. Pat. App. Pub. No. 2007/0149466. "Methods and related compositions for treating or preventing obesity, insulin resistance disorders, and mitochondrial-associated disorders;" each incorporated herein by reference in its entirety.

Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense. compounds, particularly oligonucleotides, targeted to a first nucleic acid and one or more additional antisense compounds targeted to a second nucleic acid target. For example, the first target may be a particular antisense sequence of a Sirtuin (SIRT), and the second target may be a region from another nucleotide sequence. Alternatively, compositions of the invention may contain two or more antisense compounds targeted to different regions of the same Sirtuin (SIRT) nucleic acid target. Numerous examples of antisense compounds are illustrated herein and others may be selected from among suitable compounds known in the art. Two or more combined compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least, about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document. Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

Design of Antisense Oligonucleotides Specific for a Nucleic Acid Molecule Antisense to a Sirtuin (SIRT) And/or a Sense Sound of a Sirtuin (SIRT) Polynucleotide As indicated above the term, "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid, sequences under conditions in which specific binding is desired, i.e., under physiological conditions in the case of in vivo assays or therapeutic treatment, and under conditions in which assays are performed in the case of in vitro assays.

The hybridization properties of the oligonucleotides described herein can be determined by one or more in vitro assays as known in the art. for example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecolar interactions, for example, a melting curve assay.

Melting curve assay determines the temperature at which a rapid transition from double-stranded to single-stranded conformation occurs for the natural antisense/Moleoule complex. This temperature is widely accepted as a reliable measure of the interaction strength between the two molecules.

A melting curve assay can be performed using a cDNA copy of Ac actual natural antisense RNA molecule or a synthetic DNA or RNA nucleotide corresponding to the binding site of the Molecule. Multiple kits containing all necessary reagents to perform this assay are available (e.g. Applied Biosystems inc. MeltDoctor kit). These kits include a suitable buffer solution containing one of the double strand DNA (dsDNA) binding dyes (such as ABI HRM dyes, SYBR Green, SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or Light-Typer instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identity the temperature of the rapid transition from dsDNA complex to single strand molecules. This temperature is called Tm and is directly proportional to the strength of interaction between the two molecules. Typically, Tm will exceed 40° C.

Example 2

Modulation of SIRT Polynucleotides

Treatment of HepG2 Cells with Antisense Oligonucleotides

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+ penicillin/streptomycin (Mediatech cat #MT30-002-Cl)) at 37° C. and 5% $CO_2$. One day before the experiment the cells were replated at the density of 1.5× $10^5$/ml into 6 well plates and incubated at 37° C. and 5% $CO_2$. On the day of the experiment the media in the 6 well plates was changed to fresh growth media. All antisense oligonucleotides were diluted to the concentration of 20 µM. Two µl of this solution was incubated with 400 µl of Opti-MEM media (Gibco cat #31985-070) and 4 µl of Lipofectamine 2000 (Invitrogen cat #11668019) at room temperature for 20 min and applied to each well of the 6 well plates with HepG2 cells. A Similar mixture including 2 µl of wafer instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_ml. Hs00202030_ml, Hs00953479_ml, Hs00202033_ml, Hs00978329_ml, Hs00213036_ml and Hs00213029_ml by Applied Biosystems Inc. Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Results

Figure 3:
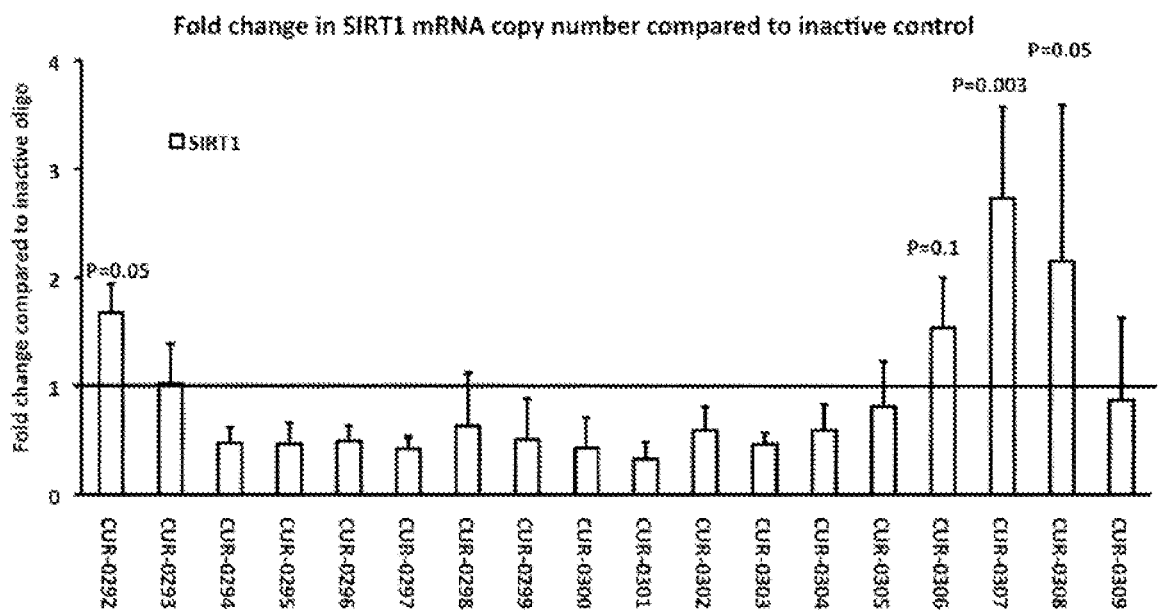
FIG. 3 shows results for the oligonucleotide walk across the SIRT antisense. Real time PCR results show that the levels of the SIRT1 mRNA in HepG2 cells are significantly increased 48 h after treatment with three of the antisense oligonucleotides desired to sirtas (CUR-0292, CUR-0307 and CUR-0308). CUR-0292 to CUR-0309 correspond to SEQ ID NOs: 24 to 41 respectively.
Figure 4:
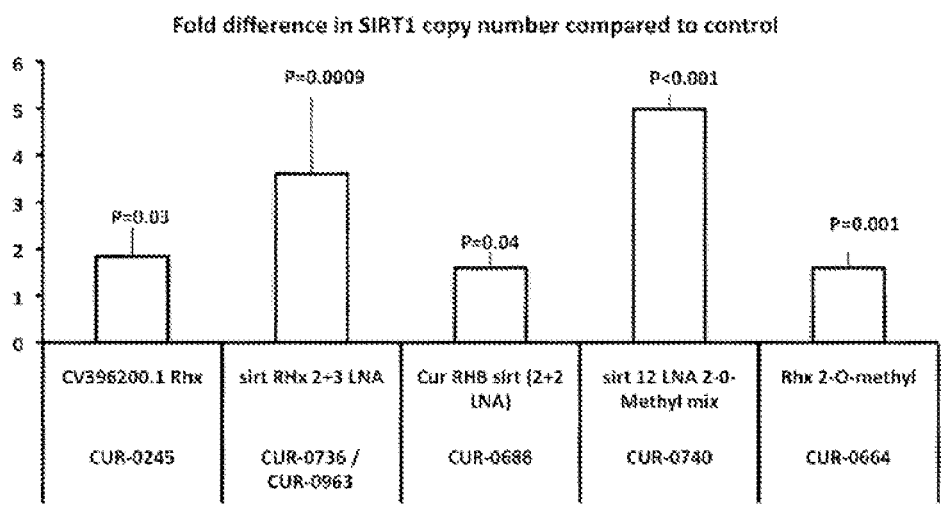
FIGS. 4 and 5 show results for PS, LNA and 2'O Me Modified oligonucleotides in HepG2 (FIG. 4) and Vero76 (FIG. 5) cells. Real time PCR results show that the levels of the SIRT1 mRNA in HepG2 cells are significantly increased 48 h after treatment with PS, LNA, 2'O Me and 2'O Me mixmer designed antisense oligonucleotides to SIRT1 antisense. Levels of SIRT1 mRNA in Vero cells also increased 48 hours after treatment with PS and LNA modified antisense oligonucleotides to SIRT1 antisense. Bars denoted as CUR-0245, CUR-0736, CUR 0688, CUR-0740 and CUR-0664 correspond to SEQ ID NOs: 42 to 46 respectively.

Real time PCR results show that the levels of the SIRT1 mRNA in HepG2 cells significantly increased 48 h after treatment with some antisense oligonucleotides to SIRT1 antisense CV396200 (FIGS. 3,4).

Figure 8:
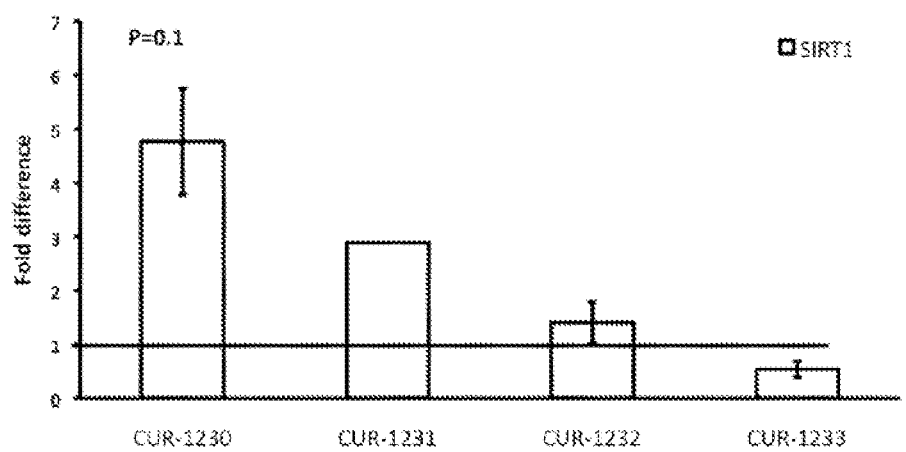
FIG. 8 shows results for oligonucleotides designed to SIRT antisense CV396200. Real Time PCR results show that levels of SIRT1 mRNA in HepG2 cells are significantly increased following treatment with one of the oligonucleotides designed to SIRT1 antisense CV396200. The bars denoted as CUR-1230 to CUR-1233 correspond to SEQ ID NOs: 50 to 53.

Real Time PCR results show that levels of SIRT1 mRNA in HepG2 cells are significantly increased in one of the oligonucleotides designed to SIRT1 antisense CV396200 (FIG. 8).

Figure 9:
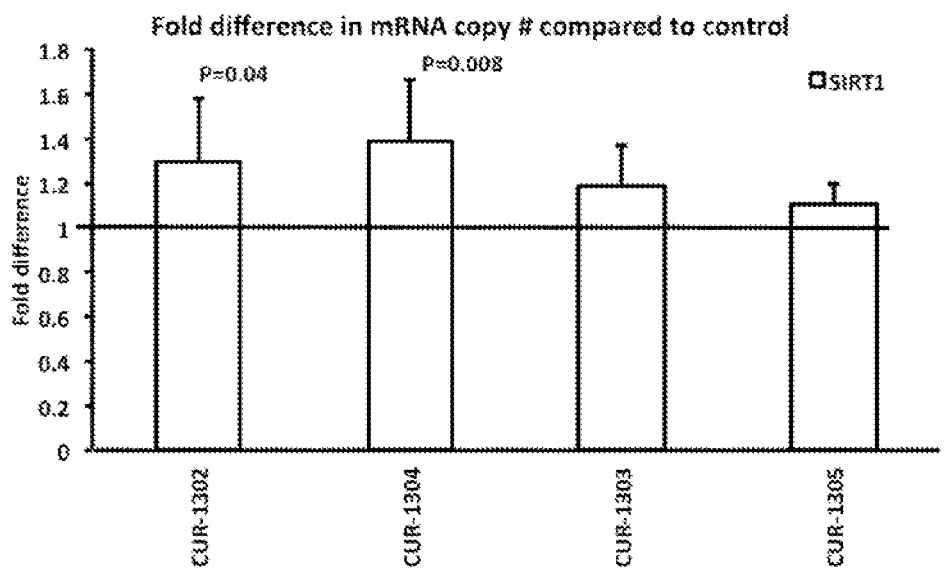
FIG. 9 shows results for oligonucleotides designed to SIRT antisense CV428275. Real Time PCR results show that levels of SIRT1 mRNA in HepG2 cells are significantly increased following treatment with two of the oligonucleotides designed to SIRT1 antisense CV428275. The bars denoted as CUR-1302, CUR-1304, CUR-1303 and CUR-1305 correspond to SEQ ID NOs: 54 to 57.

Real Time PCR results show that levels of SIRT1 mRNA in HepG2 cells are significantly increased in two of the oligonucleotides designed to SIRT1 antisense CV428275 (FIG. 9).

Figure 10:
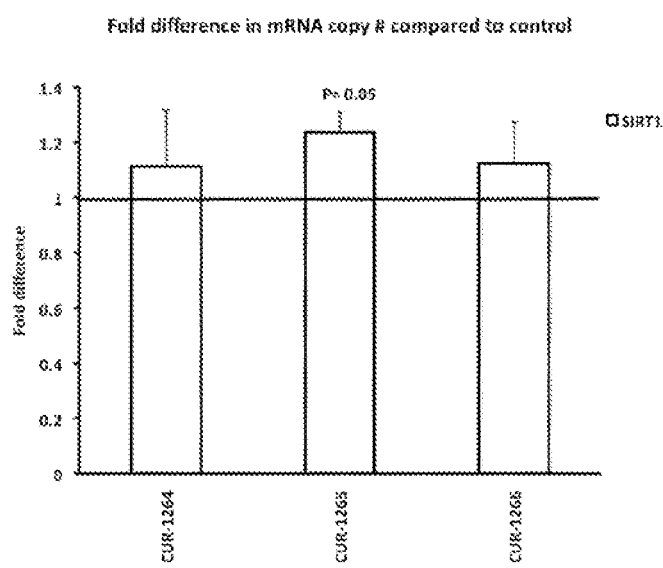
FIG. 10 shows Real time PCR results. The results show that a significant increase in SIRT1 mRNA levels in HepG2 cells 48 hours after treatment with one of the oligonucleotides designed to SIRT antisense BE717453. The bars denoted as CUR-1264 to CUR-1266 correspond to SEQ ID NOs: 58 to 60 respectively.

The results show that a significant increase in SIRT1 mRNA levels in HepG2 cells 48 hours after treatment with one of the oligonucleotides designed to SIRT antisense BE717453. (FIG. 10).

Figure 11:
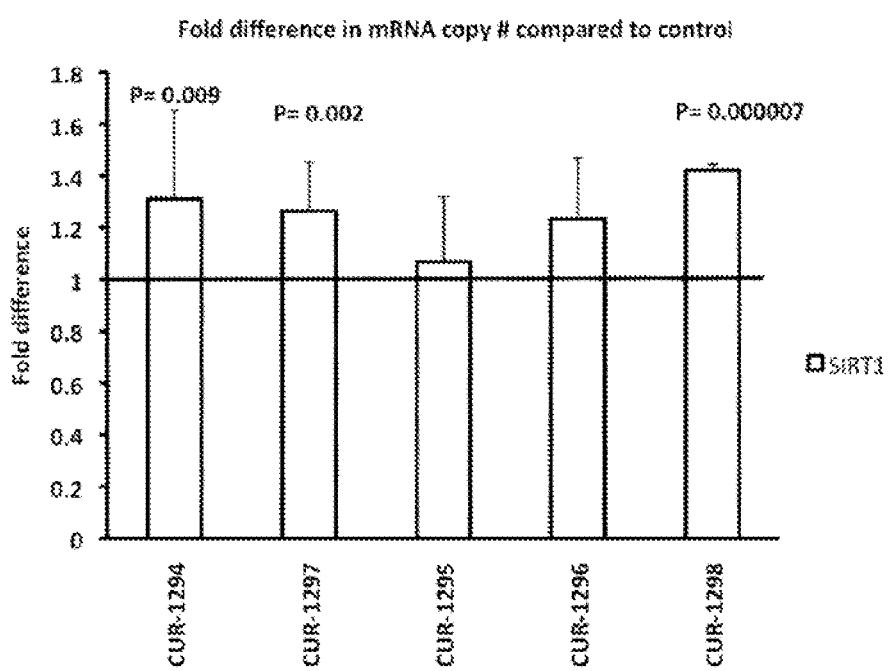
FIG. 11 shows Real time PCR results. The results show that show that the levels of the SIRT1 mRNA in HepG2 cells are significantly increased 48 h after treatment with three of the oligonucleotides designed to SIRT1 antisense AV718812. The bars denoted as CUR-1294, CUR-1297, CUR-1295, CUR-1296 and CUR-1298 correspond to SEQ ID NOs: 61 to 65 respectively.

The results show that show that the levels of the SIRT1 mRNA in HepG2 cells are significantly increased 48 h after treatment with three of the oligonucleotides designed to SIRT1 antisense AV718812 respectively (FIG. 11).

Figure 12:
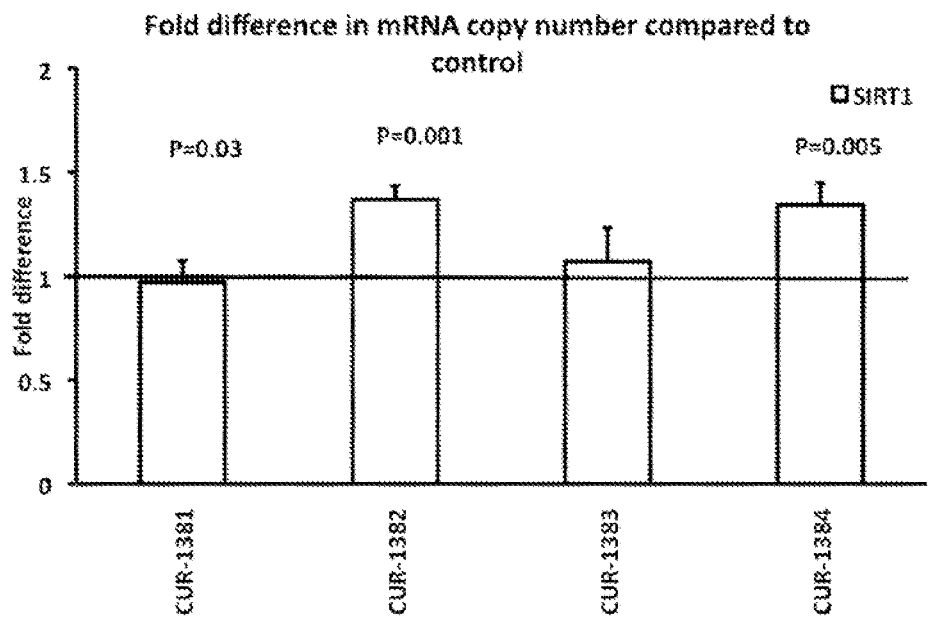
FIG. 12 is a graph of real time PCR results showing the fold change+standard deviation in SIRT1 mRNA after treatment of HepG2 cells with phosphorothioate oligonucleotides introduced using Lipofectamine 2000, as compared to control. Real time PCR results show that the levels of SIRT1 mRNA are significantly increased at HepG2 cells 48 h after treatment with two of the oligos designed to SIRT1 antisense AW169958. Bars denoted as CUR-1381, CUR-1382, CUR-1383 and CUR-1384 correspond to samples treated with SEQ ID NOS: 66 to 69 respectively.

Real time PCR results show that the levels of SIRT1 mRNA in HepG2 cells are significantly increased 48 h after treatment with two of the oligos designed to SIRT1 antisense AW169958 (FIG. 12).

Figure 17:
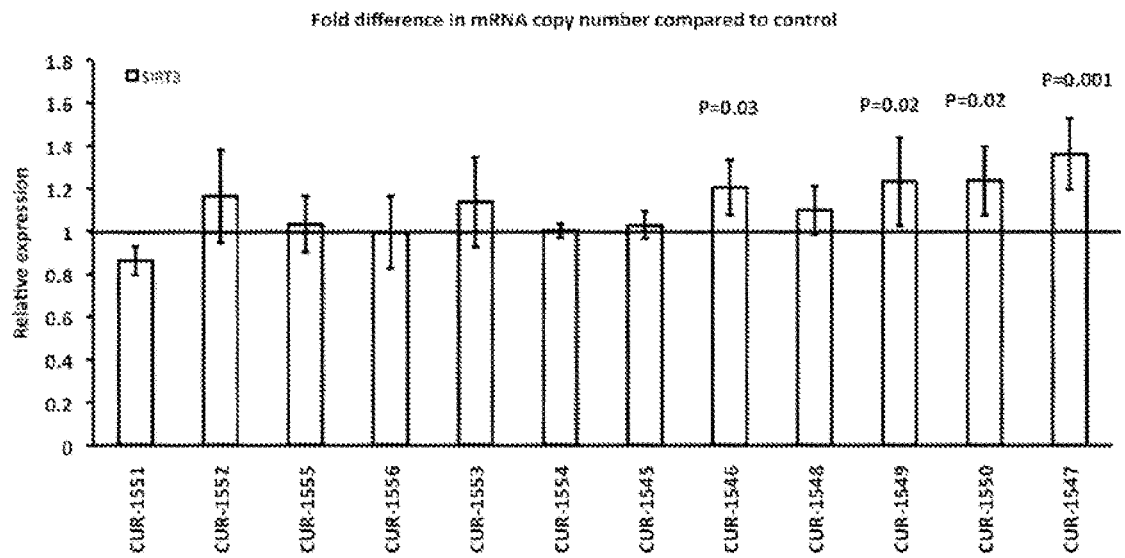
FIG. 17 is a graph of real time PCR results showing the fold change+standard deviation in Sirtuin3 mRNA after treatment of HepG2 cells with phosphorothioate oligonucleotides introduced using Lipofectamine 2000, as compared to control. RT PCR results show that sirt3 levels in HepG2 cells are increased 48 hours after treatment with phosphorothioate antisense oligonucleotides designed to sirt3 antisense Hs.683117. Bars denoted as CUR-0551, CUR-1552, CUR-1555, CUR-1556, CUR-1553, CUR-1554, CUR-1545, CUR-1546, CUR-1548, CUR-1549, CUR-1550 and CUR-1547, correspond to samples treated with SEQ ID NOS: 82 to 93 respectively.

RT PCR results show that sirt3 levels in HepG2 cells are increased 48 hours after treatment with phosphorothioate antisense oligonucleotides designed to sirt3 antisense Hs.683117 (CUR-1545-1550) (FIG. 17).

Figure 18:
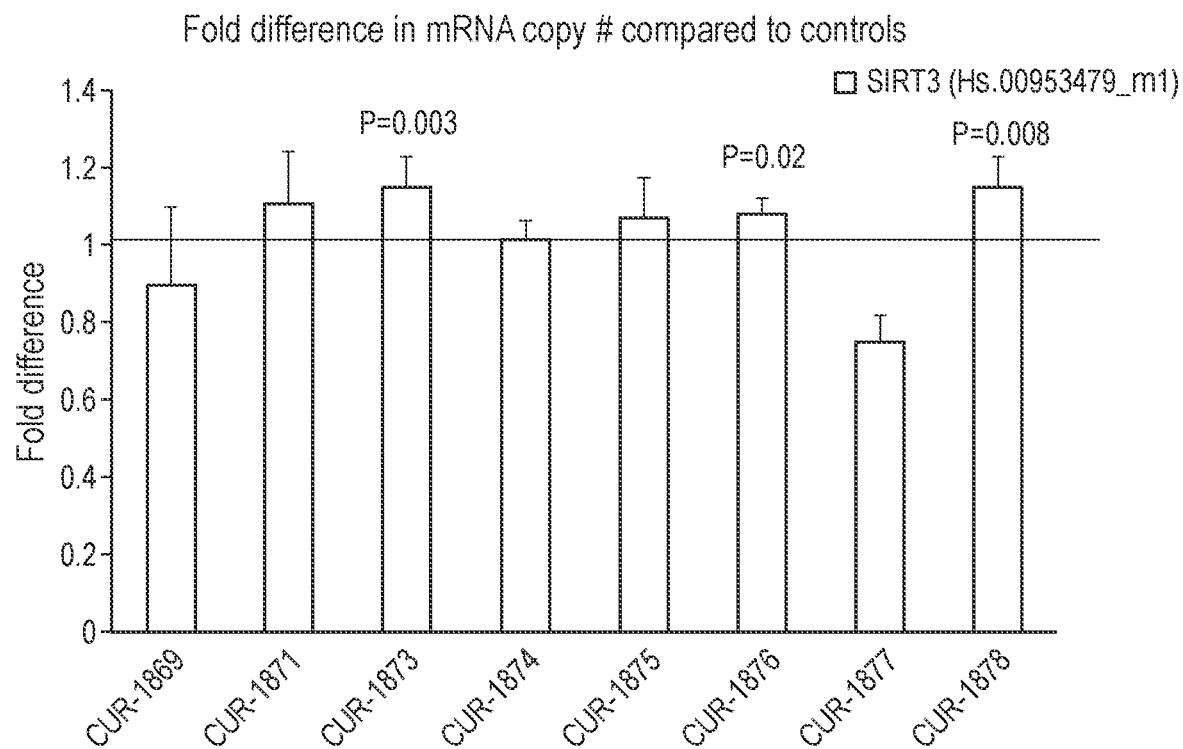
FIG. 18 is a graph of real time PCR results showing the fold change+standard deviation in Sirtuin3 mRNA after treatment of HepG2 cells with phosphorothioate oligonucleotides introduced using Lipofectamine 2000, as compared to control. RT PCR results show that sirt3 levels in HepG2 cells are increased 48 hours after treatment with phosphorothioate antisense oligonucleotides designed to sirt3 antisense BQ024738 and BE164357. Bars denoted as CUR-1869, CUR-1871 and CUR-1873 to CUR-1878 correspond to samples treated with SEQ ID NOS: 94, 95, 96 and 98, 99, 100, 101 and 102 respectively.

RT PCR results show that sirt3 levels in HepG2 cells are increased 48 hours after treatment with phosphorothioate antisense oligonucleotides designed to sirt3 antisense BQ024738 and BE164357 (FIG. 18).

Figure 19:
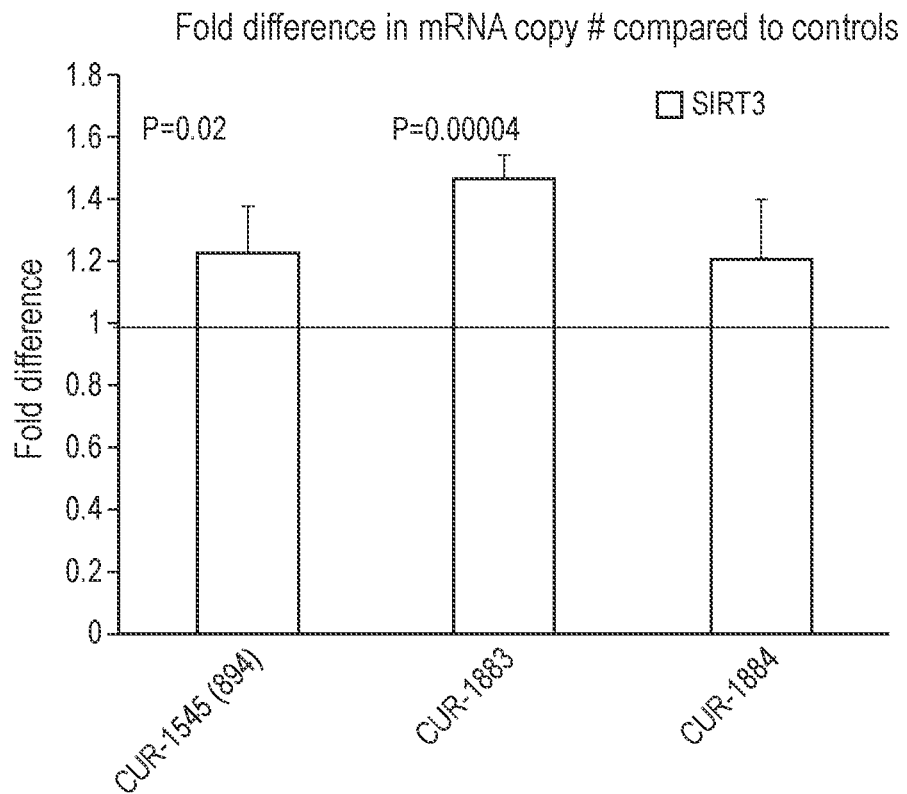
FIG. 19 is a graph of real time PCR results showing the fold change+standard deviation in SIRT3 mRNA after treatment of Hek293 cells with phosphorothioate and siRNA oligonucleotides introduced using Lipofectamine 2000, as compared to control. Bars denoted as CUR-1883 and CUR-1884 correspond to samples treated with SEQ ID NOS: 126 and 127 respectively.

RT PCR results show that sirt3 levels in HepG2 cells are increased 48 hours after treatment with siRNA oligonucleotides designed to sirt3 antisense RIC8A and PMSD13 (FIG. 19)

Figure 22:
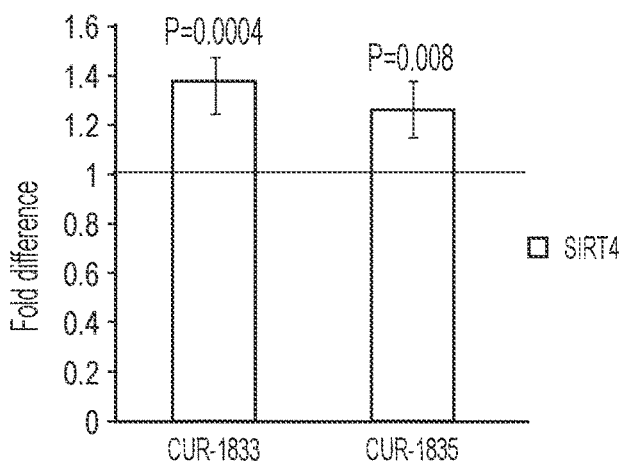
FIG. 22 is a graph of real time PCR results showing the fold change+standard deviation in SIRT4 mRNA after treatment of HepG2 cells with phosphorothioate oligonucleotides introduced using Lipofectamine 2000, as compared to control. Bars denoted as CUR-1833 and CUR-1835 correspond to samples treated with SEQ ID NOS: 104 to 107 respectively.

Real Time PCR results show that levels of SIRT4 mRNA in HepG2 cells are significantly increased 48 h after treatment with one of the antisense oligonucleotides to SIRT4 antisense (FIG. 22).

Figure 23:
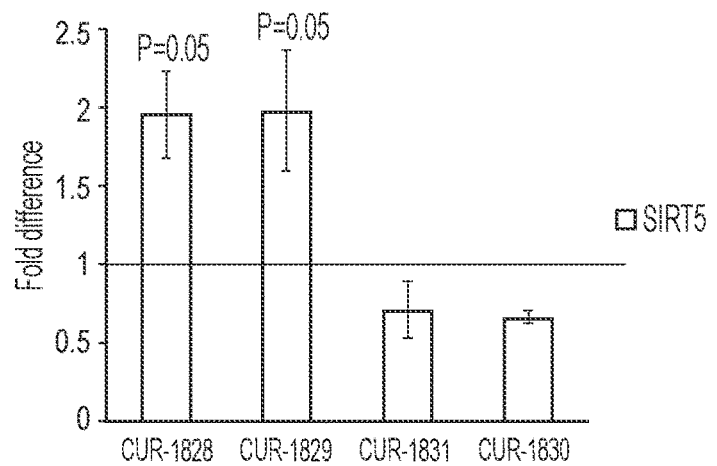
FIG. 23 is a graph of real time PCR results showing the fold change+standard deviation in SIRT5 mRNA after treatment of HepG2 cells with phosphorothioate oligonucleotides introduced using Lipofectamine 2000, as compared to control. Bars denoted as CUR-1828, CUR-1829, CUR-1831 and CUR-1830 correspond to samples treated with SEQ ID NOS: 108, 109, 111 and 110 respectively.

Real Time PCR results show that levels of SIRT5 mRNA in HepG2 cells are significantly increased 48 h after treatment with one of the antisense oligonucleotides to SIRT5 antisense Hs.671550 (FIG. 23).

Figure 24:
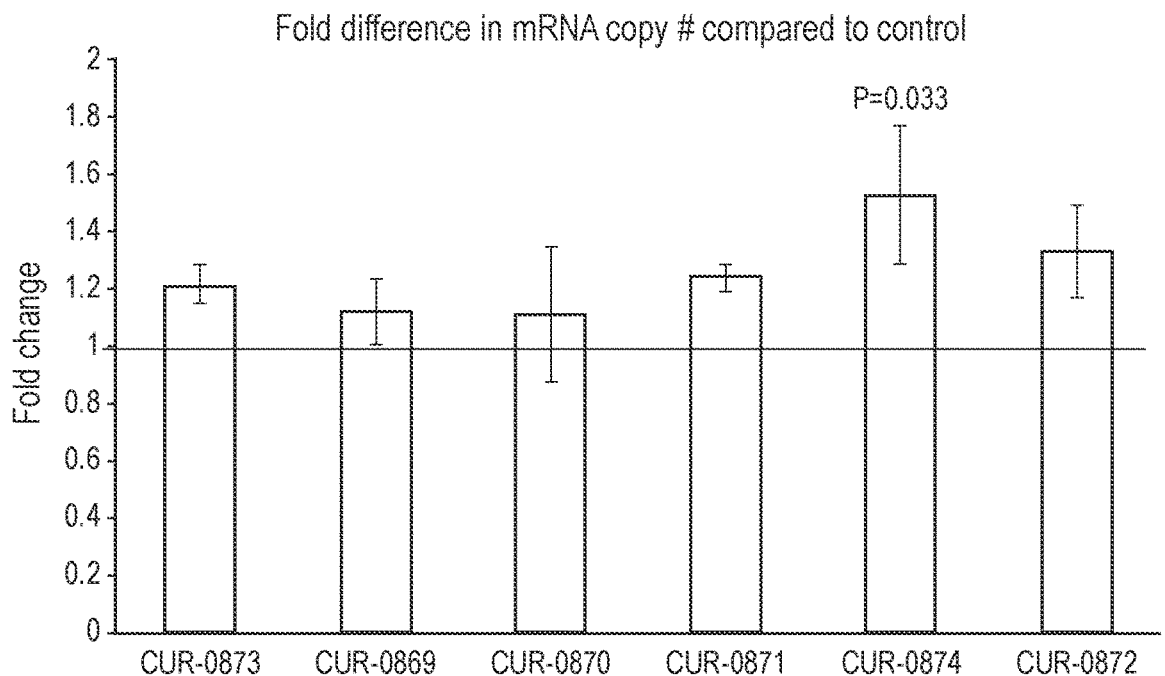
FIG. 24 is a graph of real time PCR results showing the fold change+standard deviation in SIRT6 mRNA after treatment of HepG2 cells with phosphorothioate oligonucleotides introduced using Lipofectamine 2000, as compared to control. Real time PCR results show that the levels of SIRT6 mRNA in HepG2 cells are significantly increased 48 h after treatment with one of the oligos designed to the SIRT6 antisense sequence at accession number NM_133475. Bars denoted as CUR-0873, CUR-0869 to CUR-0871, CUR-0874 and CUR-0872, correspond to samples treated with SEQ ID NOS: 116, 112, 113, 114, 117 and 115 respectively.

Real time PCR results show that the levels of SIRT6 mRNA in HepG2 cells are significantly increased 48 h after treatment with one of the oligos designed to SIRT6 antisense NM_133475 (FIG. 24).

Figure 25:
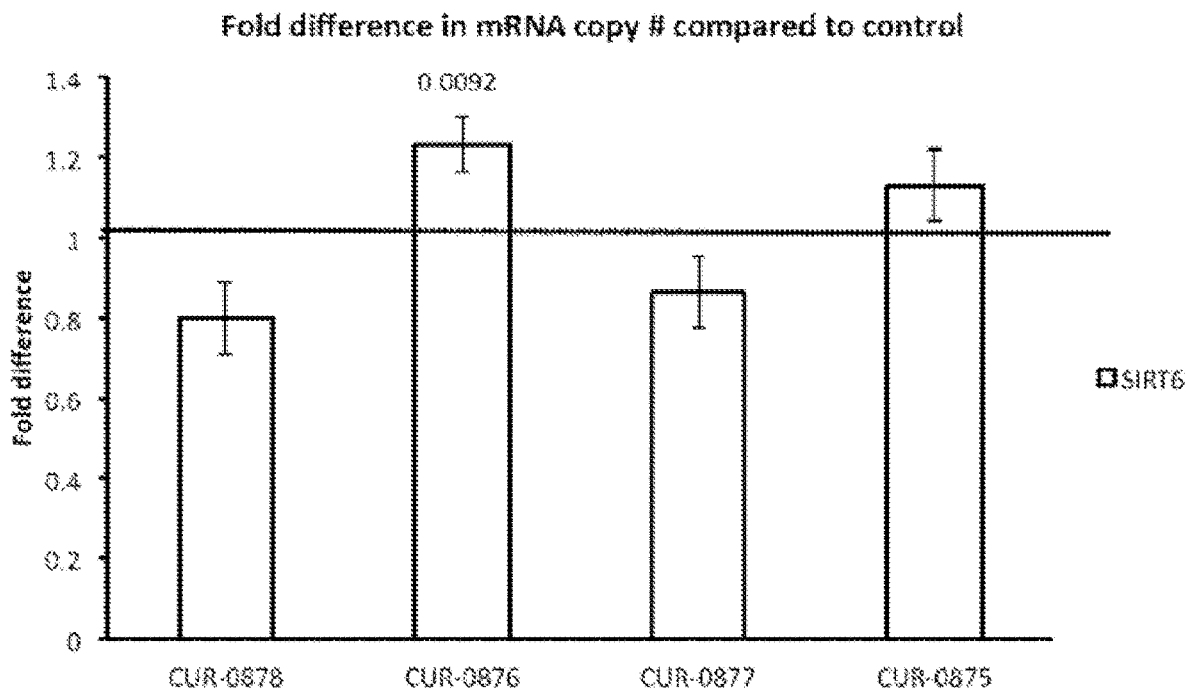
FIG. 25 is a graph of real time PCR results showing the fold change+standard deviation in SIRT6 mRNA after treatment of HepG2 cells with phosphorothioate oligonucleotides introduced using Lipofectamine 2000, as compared to control. Real time PCR results show that the levels of SIRT6 mRNA in HepG2 cells are significantly increased 48 h after treatment with one of the oligo designed to SIRT6 antisense bf772662. Bars denoted as CUR-0878, CUR-0876, CUR-0877 and CUR-0875, correspond to samples treated with SEQ ID NOS: 121, 119, 120, and 118 respectively.

Real time PCR results show that the levels of SIRT6 mRNA in HepG2 cells are significantly increased 48 h after treatment with one of the oligos designed to SIRT6 antisense bf772662 (FIG. 25).

Figure 29:
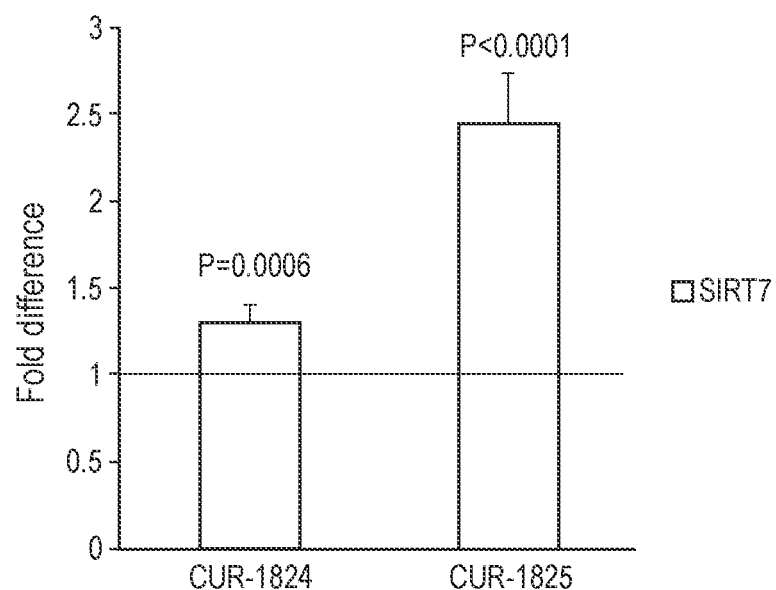
FIG. 29 is a graph of real time PCR results showing the fold change+standard deviation in SIRT7 mRNA after treatment of HepG2 cells with phosphorothioate oligonucleotides introduced using Lipofectamine 2000, as compared to control. Bars denoted as CUR-1824 and CUR-1825 correspond to samples treated with SEQ ID NOS: 122 and 123 respectively.

Real time PCR results show that the levels of SIRT7 mRNA in HepG2 cells are significantly increased 48 h after treatment with one of the oligos designed to SIRT7 antisense (FIG. 29).

Treatment of 3T3 Cells with Antisense Oligonucleotides

3T3 cells from ATCC (cat #CRL-1658) were grown in growth media (MEM/EBSS (Hyclone cat #SH30024, or Mediatech cat #MT-10-010-CV) +10% FBS (Mediatech cat #MT35-011-CV)+ penicillin/streptomycin (Mediatech cat #MT30-002-Cl)) at 37° C. and 5% $CO_2$. One day before the experiment the cells were replated at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with 3T3 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR rising ABI Taqman Gene Expression Mix (cat #4369510) and primers/probes designed by ABI (Applied Biosystems Taqman Gene Expression Assay; Hs00202021_ml by Applied Biosystems Inc., Foster City Calif.). The following PCR cycle was used: 50° C. for 2 min, 95° C. for 10 min, 40 cycles of (95° C. for 15 seconds. 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Results

Figure 13:
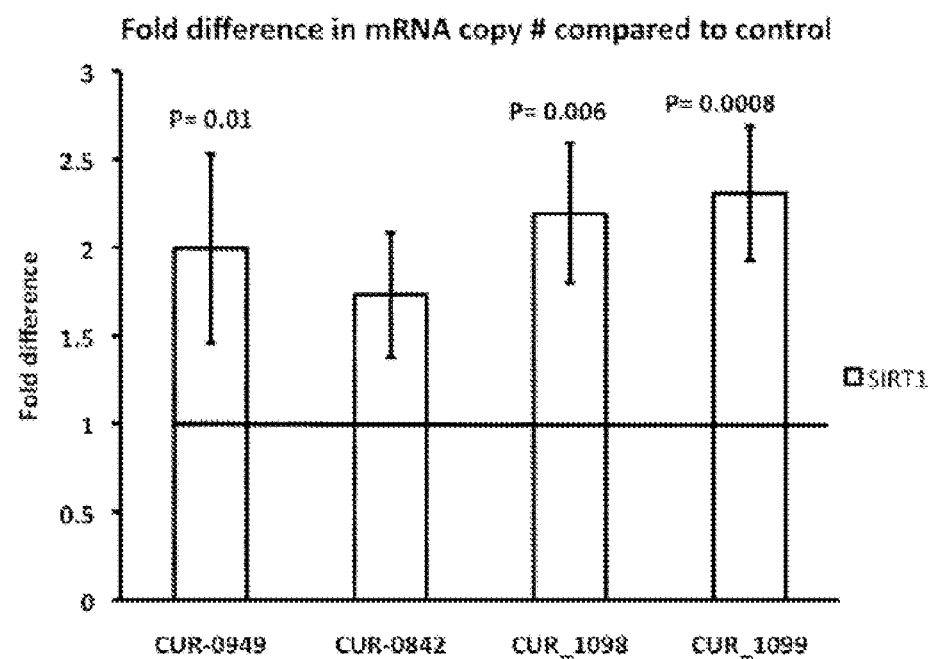
FIG. 13 is a graph of real time PCR results showing the fold change+standard deviation, in SIRT1 mRNA after treatment of 3T3 cells with phosphorothioate oligonucleotides introduced using Lipofectamine 2000, as compared to control. Real time PCR results show that the levels of SIRT1 mRNA are significantly increased in 3T3 cells 48 h after treatment with three of the oligonucleotides designed to SIRT1 mouse antisense AK044604. Bars denoted as CUR-0949, CUR-0842, CUR-1098 and CUR-1099 correspond to samples treated with SEQ ID NOS: 76, 70, 80 and 81 respectively.

Real time PCR results show that the levels of SIRT1mRNA are significantly increased in 3T3 cells 48 h after treatment with three of the oligonucleotides designed to SIRT1mouse antisense AK044604 (FIG. 13).

Figure 14:
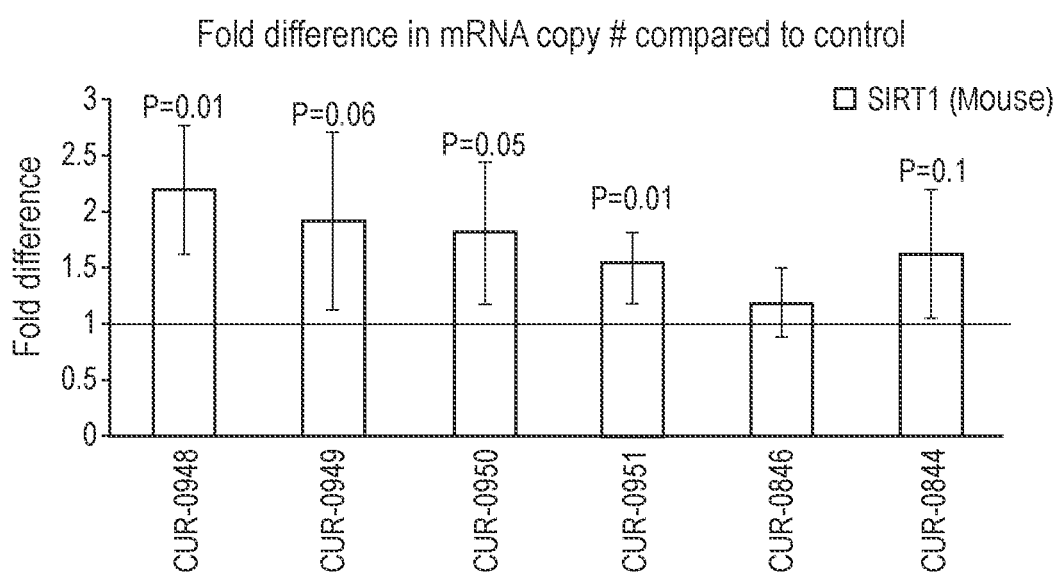
FIG. 14 is a graph of real time PCR results showing the fold change+standard deviation its SIRT1 mRNA after treatment: of 3T3 cells with phosphorothioate oligonucleotides introduced using Lipofectamine 2000, as compared to control. Real time PCR results show that the levels of SIRT1 mRNA are significantly increased in 3T3 cells 48 h after treatment with five of the oligonucleotides designed to SIRT1 mouse antisense AK044604. Bars denoted as CUR-0948 to CUR-0951, CUR-0846, and CUR-0844 correspond to samples treated with SEQ ID NOS: 75 to 78, 74 and 72 respectively.

Real time PCR results show that the levels of SIRT1 mRNA are significantly increased in 3T3 cells 48 h after treatment with five of the oligonucleotides designed to SIRT1mouse antisense AK044604 (FIG. 14).

Figure 15:
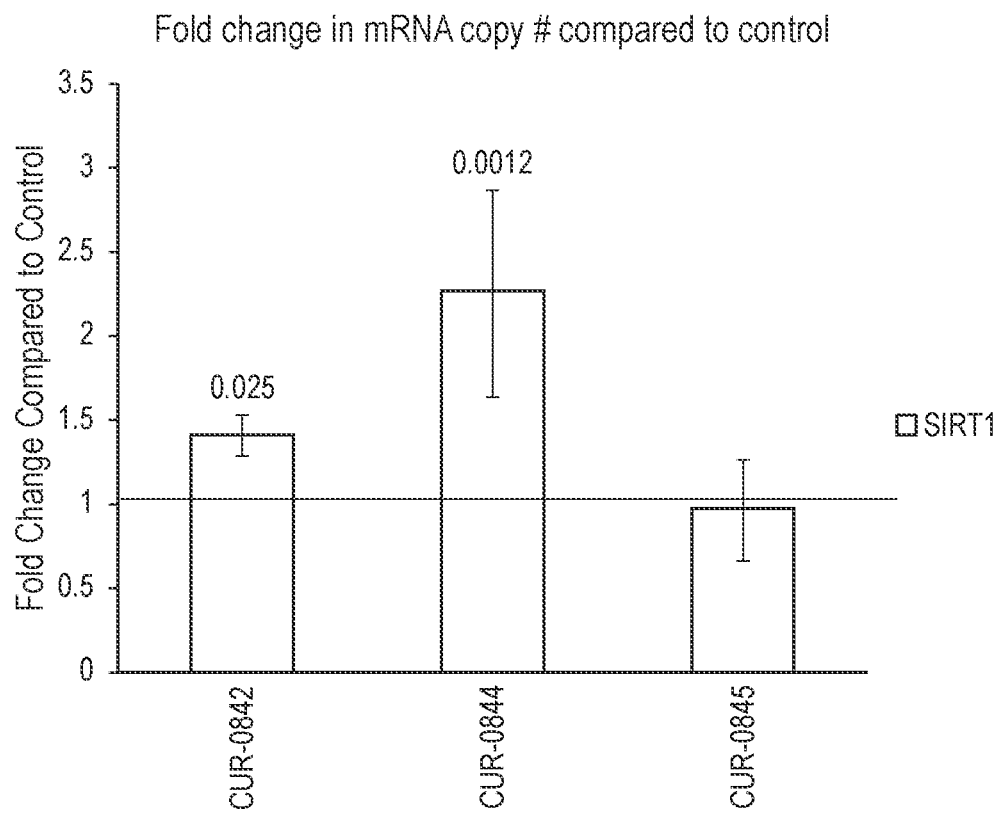
FIG. 15 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in HepG2 cells 48 h after treatment with two of the oligonucleotides designed to SIRT1 mouse antisense AK044604. Bars denoted as CUR-0842, CUR-0844, and CUR-0845 correspond to samples treated with SEQ ID NOS: 70, 72 and 73 respectively.

Real time PCR results show that the levels of SIRT1mRNA are significantly increased in 3T3 cells 48 h after treatment with two of the oligonucleotides designed to SIRT1mouse antisense AK044604 (FIG. 15).

Figure 16:
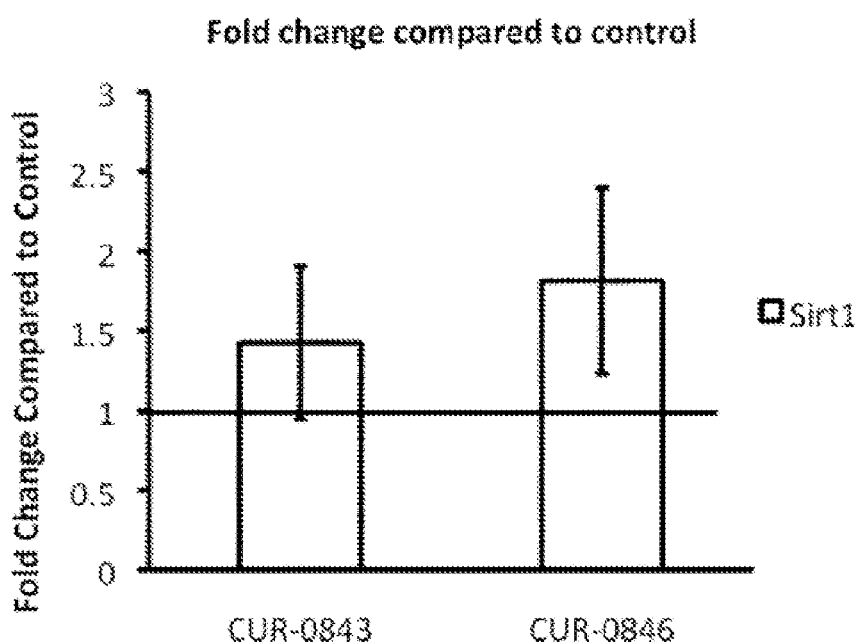
FIG. 16 is a graph of real time PCR results showing the fold change+standard deviation in SIRT1 mRNA after treatment of 3T3 cells with phosphorothioate oligonucleotides introduced using Lipofectamine 2000, as compared to control. Real time PCR results show that the levels of SIRT1 mRNA are significantly increased in HepG2 cells 48 h after treatment with two of the oligonucleotides designed to SIRT1 mouse antisense AK044604. Bars denoted as CUR-0843 and CUR-0846 correspond to samples treated with SEQ ID NOS: 71 and 74 respectively.

Real time PCR results show that the levels of SIRT1mRNA are significantly increased in 3T3 cells 48 h after treatment with two of the oligonucleotides designed to SIRT1mouse antisense AK044604 (FIG. 16).

Treatment of Vero76 Cells with Antisense Oligonucleotides

Vero76 cells from ATCC (cat #CRL-1587) were grown in growth media (MEM/EBSS (Hyclone cat #SH30024, or Mediatech cat #MT-10-10-010-CV)+10% FBS (Mediatech cat #MT35-011-CV)+ penicillin/streptomycin (Mediatech cat #MT30-002-Cl)) at 37° C. and 5% CO2. One day before the experiment the cells were replated at the density of $1.5 \times 10^5$/ml into 6 well plates and incubated at 37° C. and 5% CO2. On the day of the experiment the media in the 6 well plates was changed to fresh growth media. All antisense oligonucleotides were diluted in water to the concentration of 20 μM. 2 μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with Vero76 cells. Similar mixture including 2 μl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181), following the Manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Results

Figure 5:
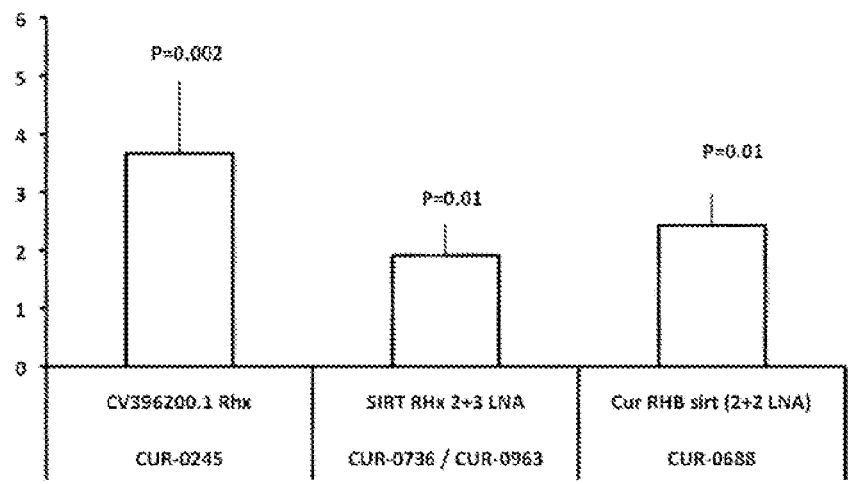

Real time PCR results show that the levels of the SIRT1mRNA in Vero cells significantly increased 48 h after treatment with antisense oligonucleotides to SIRT1antisense CV396200 (FIG. 5).

Figure 20:
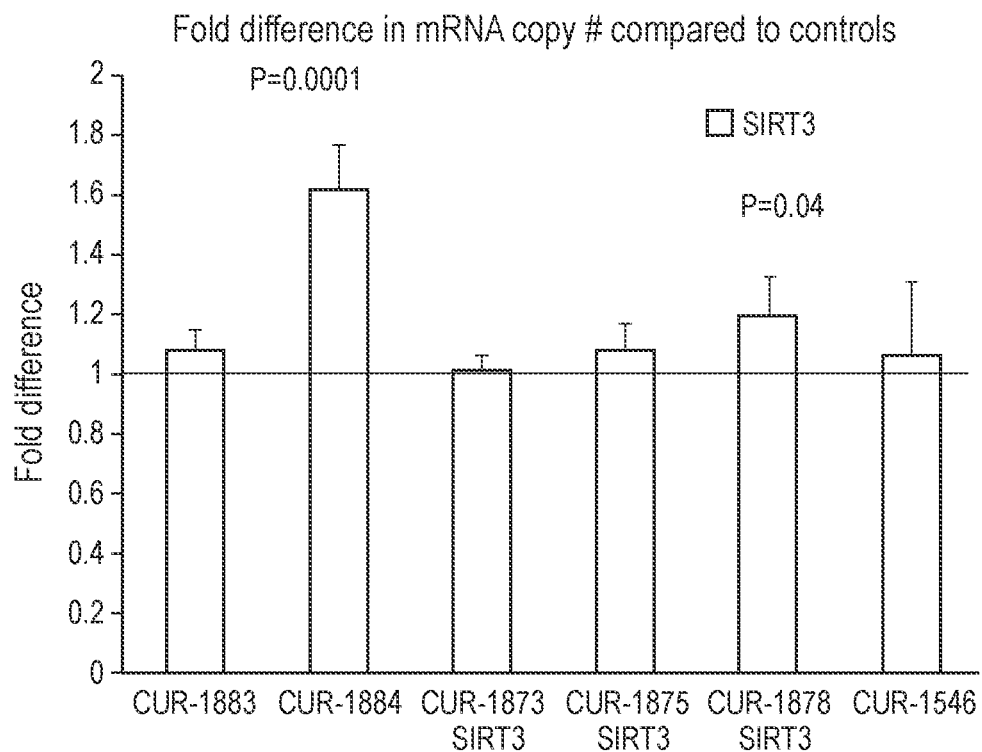
FIG. 20 is a graph of real time PCR results showing the fold change+standard deviation in SIRT3 mRNA after treatment of Vero76 cells with phosphorothioate and siRNA oligonucleotides introduced using Lipofectamine 2000, as compared to control. Bars denoted as CUR-1883 CUR-1884 CUR-1873, CUR-1875, CUR-1878 and CUR-1546 correspond to samples treated with SEQ ID NOS: 126, 127 96, 98, 100, and 92 respectively
Figure 27:
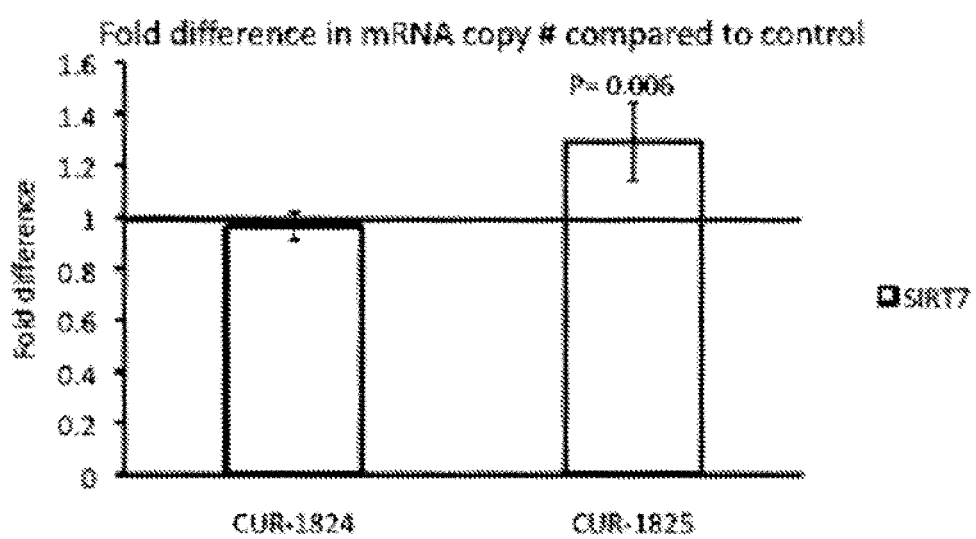
FIG. 27 is a graph of real time PCR results showing the fold change+standard deviation in SIRT7 mRNA after treatment of Vero76 cells with phosphorothioate oligonucleotides introduced using Lipofectamine 2000, as compared to control. Bars denoted as CUR-1824 and CUR-1825 correspond to samples treated with SEQ ID NOS: 122 and 123 respectively.

Real time PCR results show that the levels of the SIRT3 mRNA in Vero cells significantly increased 48 h after treatment with antisense oligonucleotides to SIRT3 antisense PSMD13 (FIG. 20). Real Time PCR results show that levels of SIRT7 mRNA in Vero76 cells are significantly increased 48 h after treatment with one of the antisense oligonucleotides to SIRT7 antisense CA308253 (FIG. 27).

Treatment of HUVEC Cells with Antisense Oligonucleotides

HUVEC cells from ATCC (Promo Cell cat #C-12253) were grown in Epithelial Growth Media (Promo Cell cat #C-22010) at 37° C. and 5% CO2. One day before the experiment the cells were replated using Promo Cell Detach Kit (cat #C-41200) at the density of $1.5 \times 10^5$/ml into 6 well plates and incubated at 37° C. and 5% CO2. On the day of the experiment the media in the 6 well plates was changed to fresh Epithelial Growth Media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with HUVEC cells. Similar mixture including 2 μl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman gene Expression Mix (cat #4369510) and primers/probes designed by ABI (Applied Biosystems Taqman Gene Expression Assay: Hs00202033_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems Inc.) or Mx4000 thermal cycler (Stratagene). Fold change in gene expression after treatment with antisense oligonucleotides was calculated based on the difference in 18S-normalized dCt values between treated and mock-transfected samples.

Figure 21:
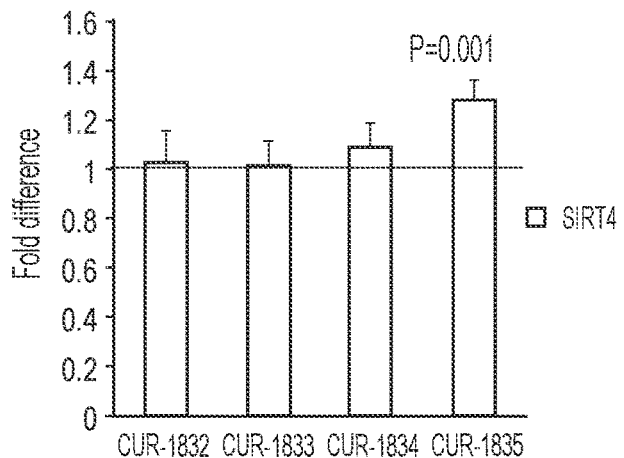
FIG. 21 is a graph of real time PCR results showing the fold change+standard deviation in SIRT4 mRNA after treatment of HUVEC cells with phosphorothioate oligonucleotides introduced using Lipofectamine 2000, as compared to control. Bars denoted as CUR-1832 and CUR-1835 correspond to samples treated with SEQ ID NOS: 105 and 107 respectively.

Results: Real Time PCR results show that levels of SIRT4 mRNA in HUVEC cells are significantly increased 48 h after treatment with one of the antisense oligonucleotides to SIRT4 antisense AA 156947 (FIG. 21).

Treatment of DBS Cells with Antisense Oligonucleotides

DBS cells from ATCC (cat #CCL-161) were grown in growth media (MEM/EBSS (Hyclone cat #SSH30024, or Mediatech cat #MT-010-010-CV)+10% FBS (Mediatech cat #MT35-011-CV)+ penicillin/streptomycin (Mediatech cat #MT30-002-CI)) at 37° C. and 5% $CO_2$. One day before the experiment the cells were replated at the density of $1.5 \times 10^5$/ml into 6 well plates and incubated at 37° C. and 5% $CO_2$. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with 3T3 cells. A Similar mixture including 2 μl of water instead of the oligonucleotide solution was used for the mock-transfected controls. After 3-18 h of incubation at 37° C. and 5% $CO_2$ the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay; Hs00202021_ml Hs00202030_ml, Ms00202033_ml, Hs00978329_ml, Hs00213036_ml and Hs00213029_ml by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Figure 26:
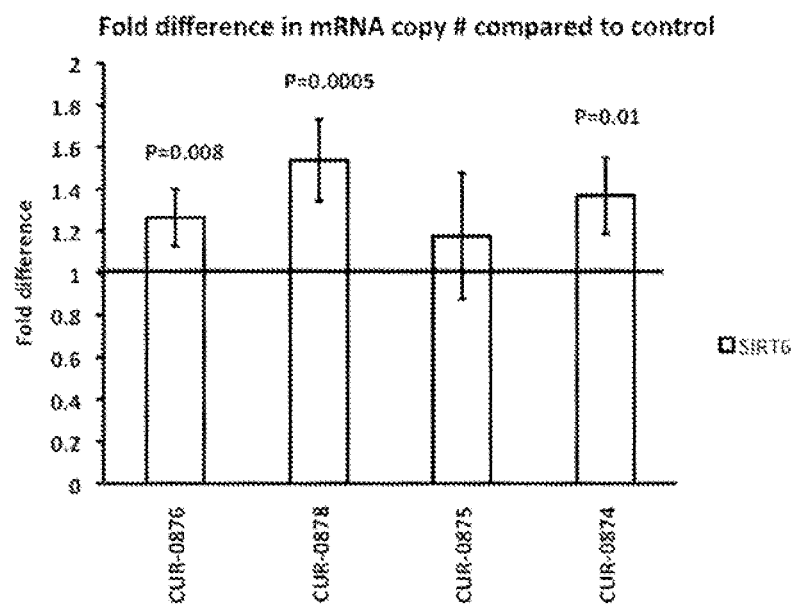
FIG. 26 is a graph of real time PCR results showing the fold change+standard deviation in SIRT6 mRNA after treatment of DBS-FCL-1 cells with phosphorothioate oligonucleotides introduced using Lipofectamine 2000, as compared to control. Real time PCR results show that the levels of SIRT6 mRNA in DBS-FCL-1 cells are significantly increased 48 h after treatment with two of the oligos designed to SIRT6 antisense bf772662 and one oligo designed to the sequence at accession number NM_133475. Bars denoted as CUR-0876, CUR-0878, CUR-0875 and CUR-0874, correspond to samples treated with SEQ ID NOS: 119, 121, 118 and 117 respectively.

Results: Real time PCR results show that the levels of SIRT6 mRNA in DBS cells are significantly increased 48 h after treatment with two of the oligo designed to SIRT6 antisense bf772662 and one oligo designed to NM_133475 (FIG. 26).

Treatment of SK-N-AS Cells with Antisense Oligonucleotides

SK-N-AS cells (neuroblastoma ATCC #CRL-2137) were grown in DMEM (Mediatech cat #10-013-CV)+10% FBS (Mediatech cat #MT35-011-CV)+penicillin/streptomycin (Mediatech cat #MT30-002-CI) at 37° C. and 5% CO2. One day before the experiment the cells were replated at the density of approximately $3 \times 10^5$/well into 6 well plates and incubated at 37° C. and 5% CO2 overnight. At dosing the cells were about 75% confluent. To dose, the media in the 6 well plates was changed to fresh DMEM+10% FBS+penicillin+streptomycin (1.5 ml/well). All antisense oligonucleotides were diluted to the concentration of 20 uM in DNAse/RNAse-free sterile water (working stock). To dose one well, 2 ul of this solution was incubated with 400 ul of Opti-MEM media (Gibco cat #31985-070) and 4 ul of Lipofectamine 2000 (Invitrogen cat #11668019) at room temperature for 20 min, then applied dropwise to one well of a 6 well plate with SK-N-AS cells (final oligo concentration=20 nM). An inactive oligonucleotide at the same concentration was used as control. Additionally one well on each plate was dosed with a mixture of 400 ul of Opti-MEM media, 4 ul of Lipofectamine 2000 and 2 ul of DNAse/RNAse-free sterile water was for the mock-transfected controls. After about 18 h of incubation at 37° C. and 5% CO2 the media was changed to fresh DMEM+10% FBS+penicillin+streptomycin. Approximately 48 h after addition of antisense oligonuclotides the media was removed and RNA was extracted from the cells using SV Total RNA Isolation System from Promega (cat #Z3105) following the manufacturers' instructions. 600 ng of RNA was added to the reverse transcription reaction performed using High Capacity cDNA kit from Applied Biosystems (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (assay ID #Hs00213029_m1 for SIRT7). The following PCR cycle was used: 50° C. for 2 min, 95° C. for 10 min, 40 cycles of (95° C. for 15 seconds, 60° C. for 1 min) on the StepOne Plus Real Time PCR system (Applied Biosystems). The assay for 18S was manufactured by ABI (cat #4319413E). Fold change in gene expression after treatment with antisense oligonuclotides was calculated based on the difference in 18S-normalized dCt values between treated and mock-transfected samples.

Figure 28:
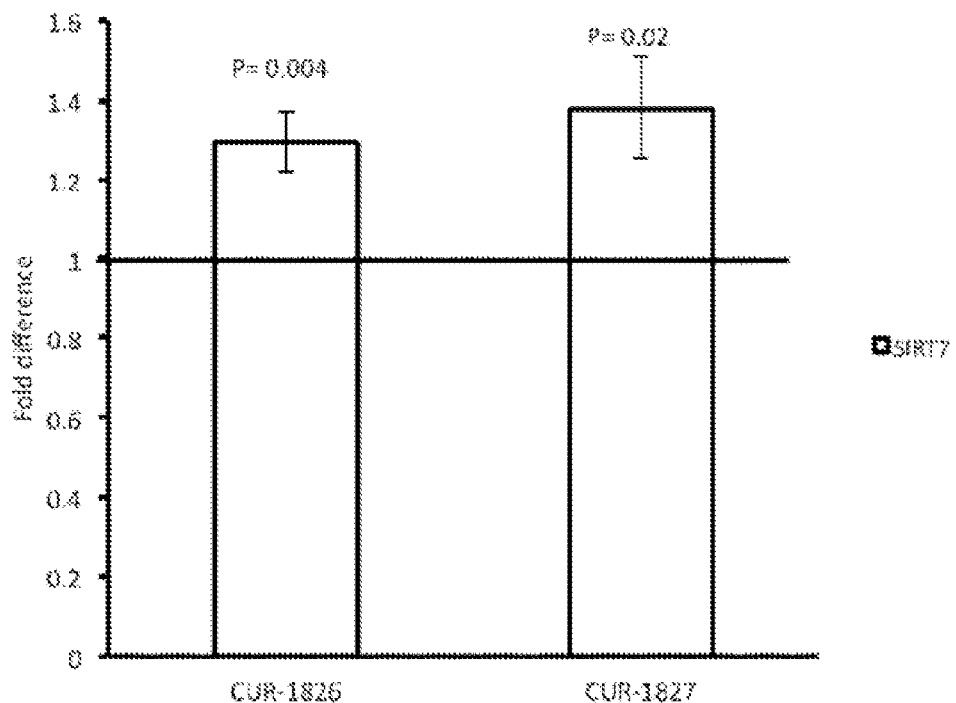
FIG. 28 is a graph of real time PCR results showing the fold change+standard deviation in SIRT7 mRNA after treatment of SR-N-AS cells with phosphorothioate oligonucleotides introduced using Lipofectamine 2000, as compared to control. Bars denoted as CUR-1824 and CUR-1825 correspond to samples treated with SEQ ID NOS: 124 and 125 respectively.

Results: Real time PCR results show that the levels of SIRT7 mRNA in SK-N-AS cells are significantly increased 48 h after treatment with oligos designed to SIRT7 antisense (FIG. 28).

Example 3

Modulation of SIRT Gene Expression

Materials and Methods

Treatment of HepG2 Cells with Naked Antisense Oligonucleotides

HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-Cl)) at 37° C. and 5% CO2. One day before the experiment the cells were replated at the density of 0.5× 10$^5$/ml into 6 well plates and incubated at 37° C. and 5% CO2. On the day of the experiment the media in the 6 well plates was replaced with 1.5 ml/well of fresh growth media. All antisense oligonucleotides were diluted in water to the concentration of 20 μM. 2 μl of this solution was incubated with 400 μl of Opti-MEM media (Gibco cat #31985-070) and 4 ul of Lipofectamine 2000 (Invitrogen cat #11668019) at room temperature for 20 min and applied to each well of the 6 well plates with HepG2 cells. Similar mixture including 2 μl of water instead of the oligonucleotide solution was used for the mock-transfected controls. After 3-18 h of incubation at 37° C. and 5% CO2 the media was changed to fresh growth media. 72 h after addition of antisense oligonucleotides the cells were redosed as described above, 48 h after the second dosing of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_m1, Hs00202030_m1, Hs00202033_m1, Hs00978329_m1, Hs00213036_m1 and Hs00213029_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Primers and probe for the custom designed Taqman assay for exon 4;

```
                                  (SEQ ID NO: 128)
AACTGGAGCTGGGGTGTCTGTTTCA
the SIRT1 natural antisense CV396200.

Forward Primer Seq.
                                  (SEQ ID NO: 129)
CCATCAGACGACATCCCTTAACAAA Reverse Primer Seq.
                                  (SEQ ID NO: 130)
ACATTATATCATAGCTCCTAAAGGAGATGCA Reporter Seq.
                                  (SEQ ID NO: 131)
CAGAGTTTCAATTCCC
```

Figure 2:
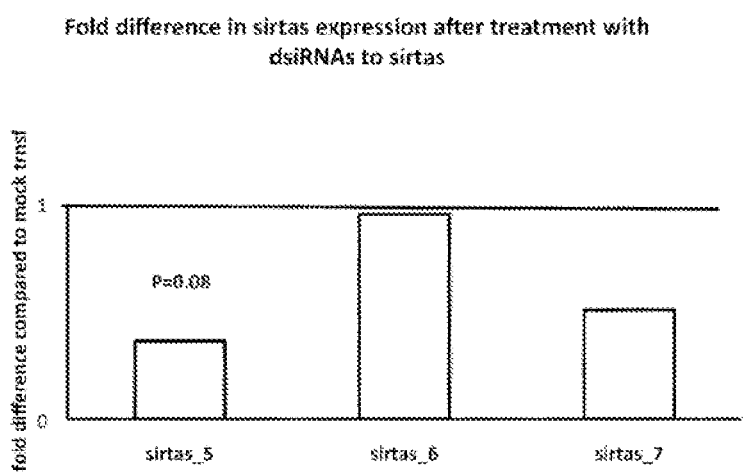

Results: The results show that the levels of the SIRT1mRNA in HepG2 cells are significantly increased 48 h after treatment with one of the siRNAs designed to sirtas (sirtas_5, P=0.01). In the same samples the levels of sirtas RNA were significantly decreased after treatment with sirtas_5, but unchanged after treatment with sirtas_6 and sirtas_7, which also had no effect on the SIRT1mRNA levels (FIG. 2). sirtas_5, sirtas_6 and sirtas_7 SEQ ID NOs: 47.48 and 49 respectively.

Treatment of Primary Monkey Hepatocytes

Primary monkey hepatocytes were introduced into culture by RxGen Inc. and plated in 6 well plates. They were treated with oligonucleotides as follows. The media in the 6 well plates was changed to fresh growth media consisting of William's Medium E (Sigma cat #W4128) supplemented with 5% FBS, 50 U/ml penicillin and 50 ug/ml streptomycin, 4 ug/ml insulin, 1 uM dexamethasone, 10 ug/ml Fungin (InVivogen, San Diego Calif.). All antisense oligonucleotides were diluted to the concentration of 20 μM, 2 μl of this solution was incubated with 400 μl of Opti-MEM media (Gibco cat #1985-070) and 4 μl of Lipofectamine 2000 (Invitrogen cat #11668019) at room temperature for 20 min and applied to each well of the 6 well plates with cells. Similar mixture including 2 μl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ug of RNA was added to the reverse transcription reaction performed using Verso cDNA kit from Thermo Scientific (cat #AB1453B) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00202021_m1, Hs00202030_m1, Hs00202033_m1, Hs00978329_m1, Hs00213036_m1 and Hs00213029_m1 by Applied Biosystems Inc., Foster City Calif.). The following PCR cycle was used: 50° C. for 2 min, 95° C. or 10 min, 40 cycles of (95° C. for 15 seconds, 60° C. for 1 min) using Mx4000 thermal cycler (Stratagene).

Fold change in gene expression after treatment with antisense oligonucleotides was calculated based on the difference in 18S-normalized dCt values between treated and mock-transfected samples.

Figure 7:
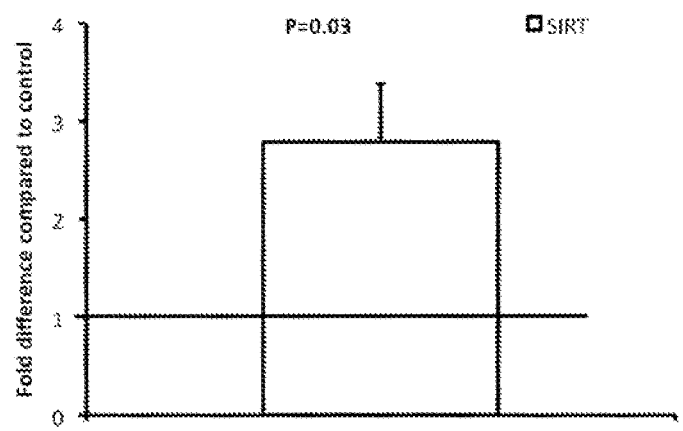
FIG. 7 shows PCR results of primary monkey liver hepatocytes. Real time PCR results show an increase in SIRT1 mRNA levels after treatment with an oligonucleotide against SIRT1 antisense. Bar denoted as CUR-0245 corresponds to SEQ ID NO: 42.

Results: The results are shown in FIG. 7. Real time PCR results show an increase in SIRT1 mRNA levels after treatment with an oligonucleotide against SIRT1 antisense.

Example 4

Efficacy and Duration of Action Study of CUR 963 in the African Green Monkey

The objective of this study was to assess and compare the effect of antisense knockdown of the discordant noncoding antisense sequences that regulate the SIRT1 genes following intravenous administration in a nonhuman primate model. The antisense oligonucleotide test articles designed to inhibit the SIRT1 regulatory sequences were designated as CUR 963.

```
CUR 963:
                                    (SEQ ID NO: 43)
+G*+T*C*T*G*A*T*G*G*+A*+G*+A.

CUR 962 (control):
                                    (SEQ ID NO: 132)
+G*+C*T*A*G*T*C*T*G*+T*+T*+G.
```

Regulatory Test Guidelines

This study was designed in accordance with accepted toxicological principles and to comply with International Conference of Harmonization (ICH) Harmonized Tripartite Guidelines (Non-Clinical Safety Studies for the Conduct of Human Clinical Trials for Pharmaceuticals ICH M3(m), 2000 Nov. 9), and generally accepted procedures for the testing of therapeutic agents.

Test And Control Articles

Test Article Identity and Preparation

The test article, CUR-963, is a chemically stabilized antisense oligonucleotide. The vehicle for intravenous delivery is phosphate-buffered saline (PBS).

Vehicle Characterization

For the PBS vehicle, the composition, batch number, expiry date and storage conditions (temperature and Light/dark) was obtained from the supplier.

Test Article Storage and Handling

The test substance and vehicle were stored according to the received storage conditions supplied by the Sponsor and manufacturer, accordingly.

Analysis of the Test Article Formulations

Samples of the test article formulation will be cryopreserved for analysis of the concentration, stability and homogeneity of the test substance formulations.

Test System Rationale

The primate is a suitable non rodent species, acceptable to regulatory authorities as an indicator of potential hazards, and for which extensive background data are available. The African green monkey specifically is a highly clinically relevant model of multiple human physiologic and disease states.

The intravenous route of administration corresponds to a possible human therapeutic route. The dose of the test articles was based on the results of the dose finding studies of analogous compounds previously performed in the African green monkey.

African green monkeys were chosen as the primate of choice as the test substances' target sequences are conserved across species with 100% homology in primates. Additionally, the test substance is a synthetic oligonucleotide. Consequently, dosing in primates allows for a superior assessment of the efficacy of these compounds that would be more reflective of the uptake likely to be seen in humans than in any other species.

Animals

Species *Chorocebus sabaeus*, non-human primate
Breed: African green monkey indigenous to St. Kitts.
Source: RxGen, Lower Bourryeau, Si, Kitts, West Indies.
Expected Age: The test animals were adults.
Expected Body Weight: The monkeys weigh approximately 3-4 kg. The actual range may vary but will be documented in the data.
Sex: The test animals were adult females.
Number of Animals: Ten animals were screened to ensure identification of 8 animals appropriate for enrollment in the study.
Number on Study: Females: 8
Justification for Number on Study: This study was designed to use the fewest number of animals possible, consistent with the primary objective of evaluating the therapeutic efficacy of the test article in the African green monkey and prior studies of the systemic administration of this type of oligonucleotide in this Species.
Animal Specification: Ten adult African Green monkeys in the weight range of 3 to 4 kg, were employed in the study. The monkeys were drug-naïve adult animals humanely trapped from the feral population that inhabits the island. Trapped monkeys were treated with antihelminthics to eliminate any possible intestinal parasite burden and were observed in quarantine for a minimum of 4 weeks prior to screening for study enrollment. The age of trapped monkeys were estimated by size and dentation, with the exclusion of older animals from the study. Prior to study enrollment, a clinical exam was performed on each monkey, including evaluation of locomotion and dexterity. Blood samples were taken and sent to Antech Diagnostics (Memphis, Tenn.) for comprehensive clinical chemistries and a complete blood count and lipid profiles (see sections 9.2 and 319507928 for specifications). Monkeys with abnormal lab values, as determined by comparison to the established normal range for monkeys in the St. Kitts colony, were excluded from the study. In order to identify 8 monkeys that satisfy this criterion, 10 monkeys were screened, with the screening of additional animals as needed. Before study initiation, the selected monkeys will be transferred to individual cages to acclimate to individual housing for a one-week period. Only animals deemed suitable for experimentation will be enrolled in the study. The actual (or estimated) age and weight ranges at the start of the study will be detailed in the raw data and final report.

Animals Health and Welfare: The highest standards of animal welfare were followed and adhered to guidelines stipulated by the St. Kitts Department of Agriculture and the U.S. Department of Health and Human Services. All studies will be conducted in accordance with these requirements and all applicable codes of practice for the care and housing of laboratory animals. All applicable standards for veterinary care, operation, and review as contained in the NIH Guide for the Care and Use of Animals. The St. Kitts facility maintains an animal research committee that reviews the protocols and inspects the facilities as required by the Guide. The Foundation has an approved assurance filed with the Office of Laboratory Animal Welfare, as required by the Guide, #A4384-01 (Axion Research Foundation/St. Kitts Biomedical Foundation). There are no special nonhuman primate veterinary care issues and biohazard issues raised by the research specified in this study.

Housing and Environment: To allow detection of any treatment-related clinical signs, the animals were housed individually prior to surgery and postoperatively until sacrifice. The primate building in which the individual cages were situated were illuminated entirely by ambient light, which at 17 degrees north latitude approximates a 12 hr:12 hr light-dark cycle as recommended in the U.S. D.H.H.S guidelines. The RxGen primate building was completely ventilated to the outside. Additional air movement was assured by ceiling fans to maintain a constant target temperature of 23-35° C., as is typical of St. Kitts throughout the year. Twenty-four hour extremes of temperature and relative humidity (which also will not be controlled) were measured daily. During the study, the cages were cleaned at regular intervals, Diet and Water: Bach animal was offered approximately 90 grams per day of a standard monkey chow diet (TekLad, Madison, Wis.). The specific nutritional composition of the diet was recorded. The water was periodically analyzed for microbiological purity. The criteria for acceptable levels of contaminants in stock diet and water supply were within the analytical specifications established by the diet manufacturer and the periodic facility water evaluations, respectively. The water met all criteria necessary for certification as acceptable for human consumption.

Experimental Design

Animal Identification and Randomization: Allocation was done by means of a stratified randomization procedure based on bodyweight and plasma cholesterol profiles. Prior to and after allocation to a group, each animal was identified by a tattoo on the abdomen. Tattoos are placed on all colony animals as a means of identification in the course of routine health inspections. A cage plan was drawn up to identify the individuals housed within, and individual monkeys were further identified by a labeled tag attached to their respective cage.

Group sizes, doses and identification numbers: The animals were assigned to 2 treatment groups, comprised of 4 monkeys in each group. Specific animal identification numbers were provided to each monkey according to the facility numbering system. This system uniquely identifies each monkey by a letter followed by a three digit number, e.g. Y032.

Route and Frequency of Administration: Animals were dosed once daily on Days 1, 3, and 5 delivered intravenously by manual infusion over-10 min. The infusion rate will be 24 mL/kg/h. The animals were sedated with ketamine and xylazinc prior to and during the dosing procedure. A venous catheter (Terumo mini vein infusion set, 20 gauge needle, or similar appropriate infusion set) was inserted into the saphenous vein. Dosing took place in each monkey between 8:00 and 10:00 a.m. shortly after the animals wake and prior to feeding. A blood sample to assess plasma cholesterol and other lipid levels as described in Blood Chemistry section below, was collected just prior to each infusion. Blood collection preceded feeding at both sampling intervals to minimize dietary effects on cholesterol measurements.

Clinical Observations: All visible signs of reaction to treatment were recorded on each day of dosing. In addition, the animals were examined at least once each week for physical attributes such as appearance and general condition.

Body Weights: Body weights were recorded at weekly intervals during the treatment and post-treatment periods.

Food Consumption: Individual food consumption was not quantified. Feeding patterns were however monitored and a note made of any major changes.

Mortality and Morbidity: Mortality and morbidity will be recorded. Any decision regarding premature sacrifice will be made after consultation with the Study Director and wish the Sponsor's Monitoring Scientist, if possible. Animals that are found dead or killed prematurely will be subjected to necropsy with collection of liver, kidney, heart and spleen lung tissues for histopathology. In the event of premature sacrifice a blood sample will also be taken (if possible) and the parameters determined. Animals that are found dead after regular working hours will be refrigerated overnight and necropsies performed at the start of the next working day. If the condition of an animal requires premature sacrifice, it will be euthanized by intravenous overdose of sodium pentobarbital. All research is governed by the Principles for Use of Animals. RxGen is required by law to comply with the U.S. Department of Health and Human Services standards for primate facility, which dictates the levels of severity that the procedures within this study, specified as mild, must abide.

Clinical Laboratory Studies

Fat Biopsies: A subcutaneous fat biopsy was performed on all study monkeys except Y775 on study days 26 by tissue extraction through a 1 cm midline incision inferior to the umbilicus. Biopsies were immediately immersed in a labeled cryotube containing 2 mls of RNAlater (Qiagen) and incubated at 4° C. overnight, after which the RNAlater was aspirated and the sample tube flash frozen in liquid nitrogen. Following transportation in liquid nitrogen total RNA was isolated for real-time qPCR of target genes.

Figure 6:
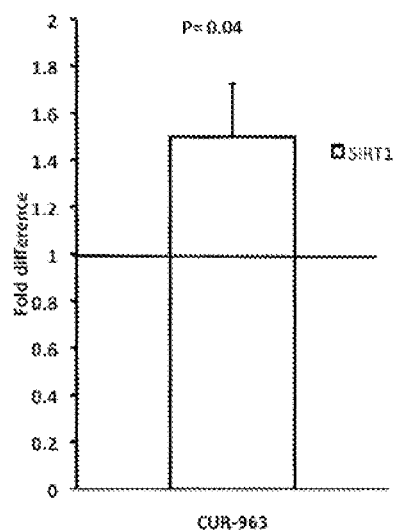
FIG. 6 shows PCR results of Monkey Fat Biopsies. Real time PCR results show an increase in SIRT1 mRNA levels in fat biopsies from monkeys dosed with CUR-963, an oligonucleotide designed to SIRT1 antisense CV396200.1. CUR-963 corresponds to SEQ ID NO: 43.

Results. Real time PCR results show an increase in SIRT1mRNA levels in fat biopsies from monkeys dosed with CUR-963, an oligonucleotide designed to SIRT1 antisense CV396200.1, compared to monkeys dosed with CUR-962 (SEQ ID NO.: 132), an oligonucleotide which had no effect on SIRT1 expression in vivo (designed to ApoA1 antisense DA327409, data not shown). mRNA levels were determined by real time PCR (FIG. 6).

Example 5

In Vivo Modulation of Sirtuin (SIRT) by Antisense DNA Oligonucleotides

Treatment with Antisense DNA Oligonucleotides (ASO); Antisense oligonucleotides (ASO) specific for SIRT1 AS are administered to C57Bl/6J mice which are fed a high fat diet for 12 weeks to induce obesity and diabetes. The treatment of the mice with ASO will start at the time of the implementation of the high fat diet. Mice are injected IP once a week with ASO prepared in normal saline, at a concentration of 5 mg/kg.

Measurements of body weight and food intake: Body weight and food intake of mice are measured twice per week, prior to IP injection of the ASO.

Blood glucose measurements: Fed and fasted blood glucose concentrations are measured each week by taking a sample of blood from the tail vein.

Glucose Tolerance Tests (GTT): The GTT will be done totally twice per mouse, halfway through the diet (at week 4) and near the end (at week 10) of the high fat diet. The GTT will inform us about the glucose tolerance of the mice that is the capacity to rapidly clear a glucose bolus from the blood stream. This is a measure for diabetes. Mice are fasted overnight for 16 hours. Mice are injected IP glucose 2 g/kg. This translates into a final volume of 0.2 ml 30% (w/v) glucose solution for a mouse of 30 g weight. Glucose measurements are taken prior to glucose injection and at 5, 15, 30, 60, 90 and 120 min post-injection. Glucose is measured by cutting the tail tip 1 mm from the end of the tail under isoflurane anesthesia prior to IP glucose injection. The blood droplet is aspirated into a strip and glucose concentration is measured with a glucometer. The GTT will be done totally twice per mouse, halfway through the diet (at week 4) and near the end (at week 10) of the high fat diet. The GTT will inform us about the glucose tolerance of the mice that is the capacity to rapidly clear a glucose bolus from the blood stream. This is a measure for diabetes.

Insulin Tolerance Test (ITT): Mice are fasted for 6 hours from 9 am till 3 pm. Mice are then injected IP 0.5-1U Insulin/kg. The insulin concentration will be adjusted such that the final injected volume is 0.1-0.15 ml. Blood, glucose measurements are taken prior to injection and at 5, 15, 30,45, and 60 minutes post-injection. Blood is collected exactly as described under GTT. In addition to monitoring the glucose levels, the behavior of the mice is constantly observed during the ITT. Hypoglycemia can manifest as a change in behavior with the animals becoming very quiet and showing discomfort. To prevent hypoglycemia, glucose (1 g/kg) is injected IP in a final volume of 0.1-0.15 ml as soon as the blood glucose concentration falls below 50 mg/ml or signs of discomfort are observed.

Blood Collection by Facial Vein Puncture: Mice are restrained by the scruff of the neck and base of the tail, slightly compressing the blood vessels of the neck through the tautness of the grip on the neck skin. The sampling site is on the jaw slightly in front of the angle of the mandible. The skin at the sampling site is punctured with an 18 G needle or a lancet at a 90° angle until the tip of the needle/lancer just passes through the skin. Blood samples are collected using microhematocrit tubes. After blood has been collected, the grip on the neck is loosened and pressure is applied at the insertion site with a gauze sponge to ensure hemostasis. 0.05-0.2 ml of blood will be collected by this method. This procedure will be performed only once in week 5 of the high fat diet and eventually in week 12 if the intracardiac puncture is not working (see below). Blood hormones which regulate the metabolism of glucose and lipids (such as insulin, adiponectin and leptin) are measured using commercially available ELISA kits. (e.g., R&D Systems, Minneapolis, Minn., Assay Pro St. Charles, Mo., Mabtech, Mariemont, Ohio)

Intracardiac Puncture: At the end of the 12 week high fat diet, mice will be anesthetized by continuous isoflurane inhalation. Anesthesia is induced by placing the mice in an induction box, which is supplied with isoflurane and oxygen. Mice will be restrained on their back. The heart is punctured with a 27 G needle. Following exsanguineation, the head is decapitated to ensure death. Tissues (liver, pancreas, white and brown adipose tissue, and skeletal muscle) are collected for further investigations (RNA and protein measurements and histology). Around 0.5-1 ml of blood will be obtained and used to determine several critical parameters of glucose and lipid metabolism (glucose, insulin, cholesterol, triglycerides, free fatty acids, leptin, adipokines, corticosteroids, thyroid hormones). If difficulties occur in this method, we will collect blood by facial vein puncture under isoflurane anesthesia instead (see above).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A synthetic, modified, single-stranded oligonucleotide of 18 to 30 nucleotides in length comprising at least one modification wherein the at least one modification is selected from: at least one modified sugar moiety; at least one modified internucleotide linkage; at least one modified nucleotide, and combinations thereof; wherein said oligonucleotide is an antisense compound which is 100% complementary to and specifically hybridizes to a natural antisense polynucleotide of a Sirtuin (SIRT) 2, 3, 4, 5 or 7 gene and upregulates the function and/or expression of a Sirtuin (SIRT) in vivo or in vitro as compared to a normal control, wherein the natural antisense polynucleotide is selected from the group consisting of SEQ ID NOs: 17, 18, 19, 20 or 23, wherein:
(a) the natural antisense polynucleotide is SEQ ID NO: 17 and the synthetic, modified oligonucleotide comprises a nucleotide sequence selected from the group consisting of SEQ ID NO: 96;
(b) the natural antisense polynucleotide is SEQ ID NO: 18 and the synthetic, modified oligonucleotide comprises a nucleotide sequence selected from the group consisting of SEQ ID NOs: 100 and 102;
(c) the natural antisense polynucleotide is SEQ ID NO: 19 and the synthetic, modified oligonucleotide comprises a nucleotide sequence selected from the group consisting of SEQ ID NO: 105;
(d) the natural antisense polynucleotide is SEQ ID NO: 20 and the synthetic, modified oligonucleotide comprises a nucleotide sequence selected from the group consisting of SEQ ID NOs: 108 and 109; or
(e) the natural antisense polynucleotide is SEQ ID NO: 23 and the synthetic, modified oligonucleotide comprises a nucleotide sequence selected from the group consisting of SEQ ID NOs: 122-125.

2. The oligonucleotide of claim 1, wherein the at least one modification comprises an internucleotide linkage selected from the group consisting of: phosphorothioate, alkylphosphonate, phosphorodithioate, alkylphosphonothioate, phosphoramidate, carbamate, carbonate, phosphate triester, acetamidate, carboxymethyl ester, and combinations thereof.

3. The oligonucleotide of claim 1, wherein said oligonucleotide comprises at least one phosphorothioate internucleotide linkage.

4. The oligonucleotide of claim 1, wherein said oligonucleotide comprises a backbone of phosphorothioate internucleotide linkages.

5. The oligonucleotide of claim 1, wherein the oligonucleotide comprises at least one modified nucleotide, said modified nucleotide selected from: a peptide nucleic acid, a locked nucleic acid (LNA), and a combination thereof.

6. The oligonucleotide of claim 1, wherein the oligonucleotide comprises a plurality of modifications, wherein said modifications comprise modified nucleotides selected from: phosphorothioate, alkylphosphonate, phosphorodithioate, alkylphosphonothioate, phosphoramidate, carbamate, carbonate, phosphate triester, acetamidate, carboxymethyl ester, and a combination thereof.

7. The oligonucleotide of claim 1, wherein the oligonucleotide comprises a plurality of modifications, wherein said modifications comprise modified nucleotides selected from: peptide nucleic acids, locked nucleic acids (LNA), and a combination thereof.

8. The oligonucleotide of claim 1, wherein the oligonucleotide comprises at least one modified sugar moiety selected from: a 2'-O-methoxyethyl modified sugar moiety, a 2'-methoxy modified sugar moiety, a 2'-O-alkyl modified sugar moiety, a bicyclic sugar moiety, and a combination thereof.

9. The oligonucleotide of claim 1, wherein the oligonucleotide comprises a plurality of modifications, wherein said modifications comprise modified sugar moieties selected from: a 2'-O-methoxyethyl modified sugar moiety, a 2'-methoxy modified sugar moiety, a 2'-O-alkyl modified sugar moiety, a bicyclic sugar moiety, and a combination thereof.

10. A modified oligonucleotide of 19-21 nucleotides in length, wherein the modified oligonucleotide comprises a nucleotide sequence selected from the group consisting of SEQ ID NOs: 96, 100, 102, 104-109 and 122 to 125.

11. A pharmaceutical composition comprising one or more modified oligonucleotides according to claim 10 and a pharmaceutically acceptable excipient.

12. The pharmaceutical composition of claim 11, wherein the one or more modified oligonucleotides comprises one or more modifications or substitutions selected from phosphorothioates, modified sugar moieties, methylphosphonate, peptide nucleic acid, locked nucleic acid (LNA) molecules, and combinations thereof.

13. The modified oligonucleotide of claim 10, wherein the modified oligonucleotide comprises one or more modifications or substitutions selected from phosphorothioate, locked nucleic acid (LNA) molecules, and combinations thereof.

14. A modified oligonucleotide of 14-27 nucleotides in length, wherein the modified oligonucleotide comprises a nucleotide sequence selected from the group consisting of SEQ ID NOs: 126 or 127.

15. The modified oligonucleotide according to claim 14, wherein the modified oligonucleotide comprises one or more modifications selected from the group consisting of a phosphorothioate, methylphosphonate, peptide nucleic acid, locked nucleic acid (LNA) molecules, and combinations thereof.

16. A pharmaceutical composition comprising the modified oligonucleotide according to claim 14.

17. A pharmaceutical composition comprising one or more modified oligonucleotides according to claim 1 and a pharmaceutically acceptable excipient.

\* \* \* \* \*